(12) United States Patent
Sahin

(10) Patent No.: US 12,270,813 B2
(45) Date of Patent: Apr. 8, 2025

(54) METHODS FOR PREDICTING THE USEFULNESS OF DISEASE SPECIFIC AMINO ACID MODIFICATIONS FOR IMMUNOTHERAPY

(71) Applicant: BioNTech SE, Mainz (DE)

(72) Inventor: Ugur Sahin, Mainz (DE)

(73) Assignee: BioNTech SE, Mainz (DE)

( * ) Notice: Subject to any disclaimer, the term of this patent is extended or adjusted under 35 U.S.C. 154(b) by 709 days.

(21) Appl. No.: 16/620,459

(22) PCT Filed: Jun. 1, 2018

(86) PCT No.: PCT/EP2018/064468
§ 371 (c)(1),
(2) Date: Dec. 6, 2019

(87) PCT Pub. No.: WO2018/224405
PCT Pub. Date: Dec. 13, 2018

(65) Prior Publication Data
US 2020/0209251 A1   Jul. 2, 2020

(30) Foreign Application Priority Data

Jun. 9, 2017   (WO) ............... PCT/EP2017/064140

(51) Int. Cl.
*G01N 33/68*  (2006.01)
*A61K 39/00*  (2006.01)

(52) U.S. Cl.
CPC ......... *G01N 33/68* (2013.01); *A61K 39/0011* (2013.01); *A61K 39/001156* (2018.08); *A61K 39/001188* (2018.08); *A61K 2039/53* (2013.01); *A61K 2039/876* (2018.08); *G01N 2333/70514* (2013.01); *G01N 2333/70517* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. | |
| 5,264,618 A | 11/1993 | Felgner et al. | |
| 5,703,055 A | 12/1997 | Felgner et al. | |
| 6,251,399 B1 | 6/2001 | Diamond et al. | |
| 6,472,176 B2 | 10/2002 | Kovesdi et al. | |
| 6,500,641 B1 | 12/2002 | Chen et al. | |
| 6,586,410 B1 | 7/2003 | Wheeler et al. | |
| 7,303,881 B2 | 12/2007 | Huang et al. | |
| 7,462,354 B2 | 12/2008 | Sette et al. | |
| 7,790,696 B2 | 9/2010 | Gregoriadis | |
| 8,140,270 B2 | 3/2012 | Kingsmore et al. | |
| 8,217,016 B2 | 7/2012 | Hoerr et al. | |
| 8,349,558 B2 | 1/2013 | Fatho et al. | |
| 8,703,142 B2 | 4/2014 | Diamond et al. | |
| 8,853,283 B2 | 10/2014 | Platscher et al. | |
| 8,877,206 B2 | 11/2014 | Chen et al. | |
| 9,115,402 B2 | 8/2015 | Hacohen et al. | |
| 10,055,540 B2 | 8/2018 | Yelensky et al. | |
| 10,738,355 B2 | 8/2020 | Sahin et al. | |
| 11,156,617 B2* | 10/2021 | Sahin | G01N 33/505 |
| 11,222,711 B2 | 1/2022 | Sahin et al. | |
| 11,248,264 B2* | 2/2022 | Sahin | G16B 40/00 |
| 2006/0188490 A1 | 8/2006 | Hoerr et al. | |
| 2006/0204523 A1 | 9/2006 | Khromykh et al. | |
| 2007/0025968 A1 | 2/2007 | Van Der Burg et al. | |
| 2008/0171711 A1 | 7/2008 | Hoerr et al. | |
| 2009/0055944 A1 | 2/2009 | Korman et al. | |
| 2009/0217401 A1 | 8/2009 | Korman et al. | |
| 2009/0298056 A1 | 12/2009 | Mautner et al. | |
| 2010/0151492 A1 | 6/2010 | Ahmed et al. | |
| 2010/0304989 A1 | 12/2010 | Von Hoff et al. | |
| 2011/0195090 A1 | 8/2011 | Dimitrov | |
| 2011/0257890 A1 | 10/2011 | Weinschenk et al. | |
| 2012/0237975 A1 | 9/2012 | Schrum et al. | |
| 2013/0115272 A1 | 5/2013 | de Fougerolles et al. | |
| 2013/0123481 A1 | 5/2013 | de Fougerolles et al. | |
| 2013/0156849 A1 | 6/2013 | de Fougerolles et al. | |
| 2013/0203115 A1 | 8/2013 | Schrum et al. | |
| 2013/0237593 A1 | 9/2013 | de Fougerolles et al. | |

(Continued)

FOREIGN PATENT DOCUMENTS

| | | |
|---|---|---|
| CN | 1237909 A | 12/1999 |
| CN | 1440462 A | 9/2003 |

(Continued)

OTHER PUBLICATIONS

Vormehr et al., Current Opinion in Immunology vol. 39, pp. 14-22 (Year: 2016).*
Kreiter, S., et al. Nature 520, 692-696 (Year: 2015).*
Kreiter, S. et al., Mutant MHC class II epitopes drive therapeutic immune responses to cancer, Nature, 520(7549):692-6 (2015).
Vormehr, M. et al., Mutanome directed cancer immunotherapy, Curr Opin Immunol, 39:14-22 (2016).
Castle, J.C. et al., Exploiting the Mutanome for Tumor Vaccination, Amer. Assoc. Canc. Res., 72(5):1081-1091 (2012).

(Continued)

*Primary Examiner* — Shanon A. Foley
*Assistant Examiner* — Myron G Hill
(74) *Attorney, Agent, or Firm* — Choate, Hall & Stewart LLP; Brenda Herschbach Jarrell; Rolando Medina

(57) ABSTRACT

The present invention relates to methods for predicting whether peptides or polypeptides comprising disease specific amino acid modifications, in particular tumor-associated neo-antigens, comprise epitopes, in particular tumor-associated neo-epitopes, which are useful for immunotherapy such as for vaccination. The methods of the invention may be used, in particular, for the provision of vaccines which are specific for a patient's tumor and, thus, in the context of personalized cancer vaccines.

Figure 1:
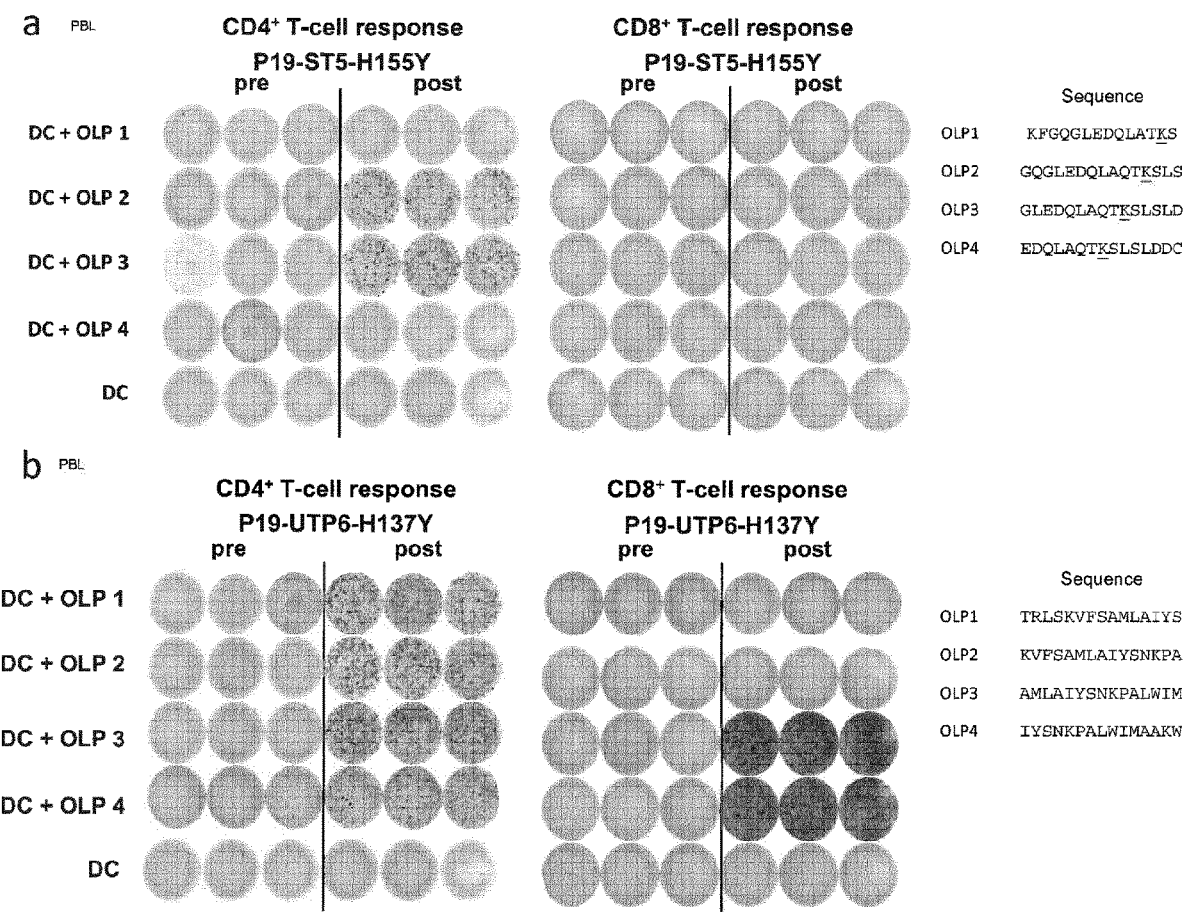
Figure 1:
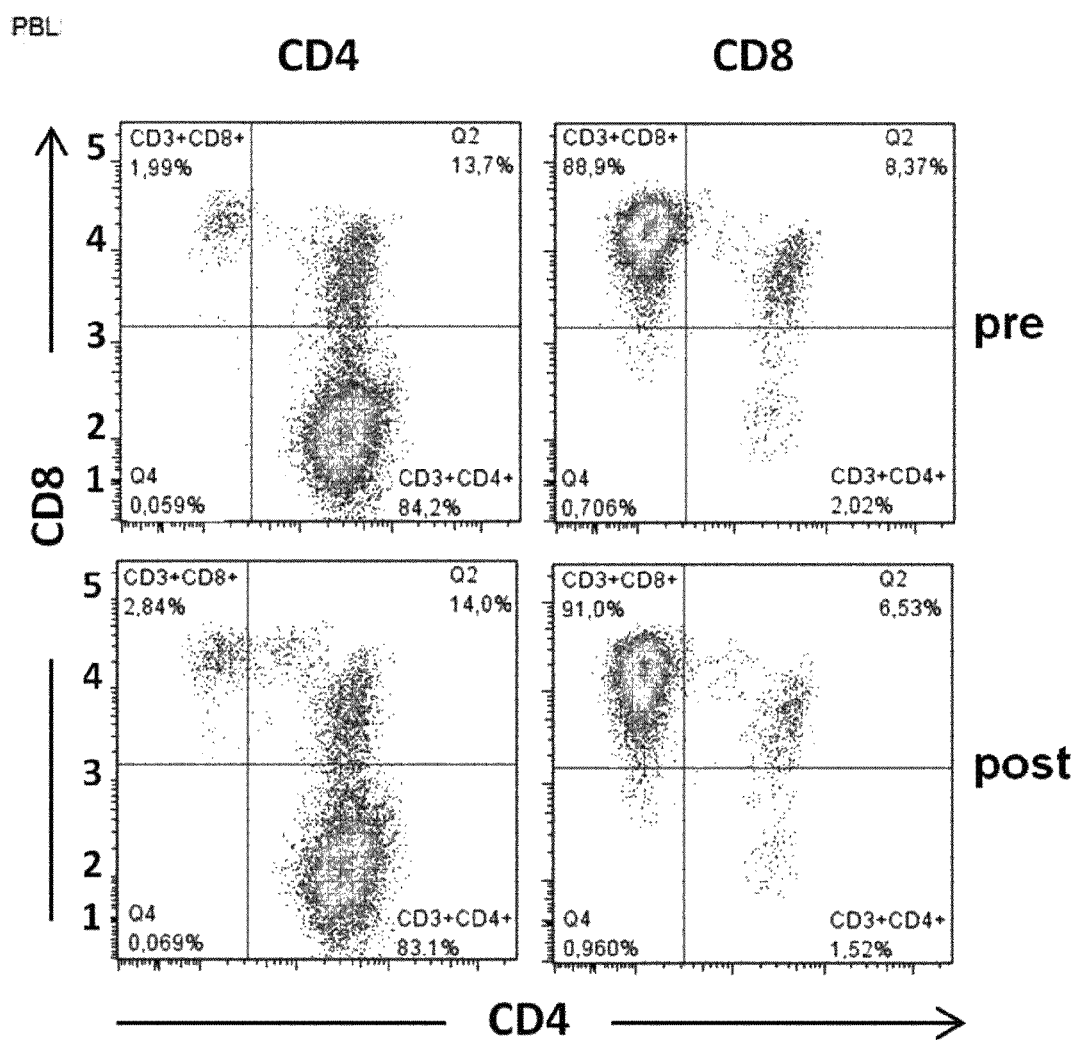

26 Claims, 9 Drawing Sheets
Specification includes a Sequence Listing.

(56) References Cited

U.S. PATENT DOCUMENTS

| | | |
|---|---|---|
| 2013/0237594 A1 | 9/2013 | de Fougerolles et al. |
| 2013/0244278 A1 | 9/2013 | de Fougerolles et al. |
| 2013/0244279 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0255281 A1 | 10/2013 | Bray |
| 2013/0266640 A1 | 10/2013 | de Fougerolles et al. |
| 2014/0010861 A1 | 1/2014 | Bancel et al. |
| 2014/0147454 A1 | 5/2014 | Chakraborty et al. |
| 2014/0178438 A1 | 6/2014 | Sahin et al. |
| 2015/0017211 A1 | 1/2015 | de Fougerolles et al. |
| 2015/0030576 A1 | 1/2015 | Bancel |
| 2015/0167017 A1 | 6/2015 | Roy et al. |
| 2016/0125129 A1 | 5/2016 | Sahin et al. |
| 2017/0016075 A1 | 1/2017 | Velculescu et al. |
| 2019/0250166 A1 | 8/2019 | Sahin et al. |
| 2021/0164034 A1 | 6/2021 | Sahin et al. |
| 2022/0074948 A1 | 3/2022 | Sahin et al. |
| 2022/0093209 A1 | 3/2022 | Sahin et al. |
| 2022/0282322 A1 | 9/2022 | Sahin et al. |

FOREIGN PATENT DOCUMENTS

| | | |
|---|---|---|
| CN | 103180730 A | 6/2013 |
| CN | 103608033 B | 6/2016 |
| EP | 242108 A2 | 10/1987 |
| EP | 0839912 A1 | 5/1998 |
| EP | 1242108 A1 | 9/2002 |
| EP | 1392341 A2 | 3/2004 |
| EP | 2100620 A1 | 9/2009 |
| EP | 2569633 A2 | 3/2013 |
| EP | 3256853 A1 | 12/2017 |
| EP | 3473267 A1 | 4/2019 |
| JP | 2004527213 A | 9/2004 |
| JP | 2006-518982 A | 8/2006 |
| JP | 2007-501200 A | 1/2007 |
| JP | 2010-540672 B | 12/2010 |
| JP | 2011-135874 A | 7/2011 |
| JP | 2014-523406 A | 9/2014 |
| WO | WO-1994/023031 A1 | 10/1994 |
| WO | WO-96/33739 A1 | 10/1996 |
| WO | WO-97/24447 A1 | 7/1997 |
| WO | WO-97/40156 A1 | 10/1997 |
| WO | WO-97/40852 A1 | 11/1997 |
| WO | WO-98/16238 A2 | 4/1998 |
| WO | WO-1998/014464 A1 | 4/1998 |
| WO | WO-1999/024566 A1 | 5/1999 |
| WO | WO-99/34014 A2 | 7/1999 |
| WO | WO-99/34015 A2 | 7/1999 |
| WO | WO-1999/052503 A2 | 10/1999 |
| WO | WO-2000/20029 A1 | 4/2000 |
| WO | WO-2000/067761 A1 | 11/2000 |
| WO | WO-01/19408 A1 | 3/2001 |
| WO | WO-01/29233 A2 | 4/2001 |
| WO | WO-01/047541 A1 | 7/2001 |
| WO | WO-2001/047959 A2 | 7/2001 |
| WO | WO-01/55393 A2 | 8/2001 |
| WO | WO-01/82963 A2 | 11/2001 |
| WO | WO-2001/093902 A2 | 12/2001 |
| WO | WO-02/12281 A2 | 2/2002 |
| WO | WO-2002/048377 A2 | 6/2002 |
| WO | WO-2002/083714 A2 | 10/2002 |
| WO | WO-02/098443 A2 | 12/2002 |
| WO | WO-2003/051401 A2 | 6/2003 |
| WO | WO-03/059381 A2 | 7/2003 |
| WO | WO-03/070162 A2 | 8/2003 |
| WO | WO-2003/068257 A1 | 8/2003 |
| WO | WO-03/078595 A2 | 9/2003 |
| WO | WO-2003/106692 A2 | 12/2003 |
| WO | WO-2004/004743 A1 | 1/2004 |
| WO | WO-2004/031230 A2 | 4/2004 |
| WO | WO 2005/016376 A1 | 2/2005 |
| WO | WO-2005/023295 A2 | 3/2005 |
| WO | WO-2005/028505 A2 | 3/2005 |
| WO | WO-2005/030250 A2 | 4/2005 |
| WO | WO-2005/039533 A1 | 5/2005 |
| WO | WO-2005/040816 A1 | 5/2005 |
| WO | WO-2005/100390 A2 | 10/2005 |
| WO | WO-2005/110338 A2 | 11/2005 |
| WO | WO-2006/121168 A1 | 11/2006 |
| WO | WO-2007/024708 A2 | 3/2007 |
| WO | WO-2007/025760 A2 | 3/2007 |
| WO | WO-2007/031222 A2 | 3/2007 |
| WO | WO-2007/036366 A2 | 4/2007 |
| WO | WO-2007/101227 A2 | 9/2007 |
| WO | WO-2007/106545 A2 | 9/2007 |
| WO | WO-2008/080468 A1 | 7/2008 |
| WO | WO-2008/083174 A2 | 7/2008 |
| WO | WO-2008/085562 A2 | 7/2008 |
| WO | WO-2008/116078 A2 | 9/2008 |
| WO | WO-2008/156712 A1 | 12/2008 |
| WO | WO-2009/046738 A1 | 4/2009 |
| WO | WO-2009/053041 A2 | 4/2009 |
| WO | WO-2009/118296 A2 | 10/2009 |
| WO | WO-2009/129227 A1 | 10/2009 |
| WO | WO-2010/037395 A2 | 4/2010 |
| WO | WO-2010/037539 A2 | 4/2010 |
| WO | WO-2010/066418 A1 | 6/2010 |
| WO | WO-2011/012316 A2 | 2/2011 |
| WO | WO-2011/143656 A2 | 11/2011 |
| WO | WO-2012/045075 A1 | 4/2012 |
| WO | WO-2012/045082 A2 | 4/2012 |
| WO | WO-2012/135805 A2 | 10/2012 |
| WO | WO-2012/159643 A1 | 11/2012 |
| WO | WO-2012/159729 A1 | 11/2012 |
| WO | WO-2012/159754 A1 | 11/2012 |
| WO | WO-2013/040142 A2 | 3/2013 |
| WO | WO-2013/052523 A1 | 4/2013 |
| WO | WO-2013/090648 A1 | 6/2013 |
| WO | WO-2013/124701 A2 | 8/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151672 A2 | 10/2013 |
| WO | WO-2014/012051 A1 | 1/2014 |
| WO | WO-2014/071219 A1 | 5/2014 |
| WO | WO-2014/093924 A1 | 6/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/159813 A1 | 10/2014 |
| WO | WO-2014/160243 A1 | 10/2014 |
| WO | WO-2014/164253 A1 | 10/2014 |
| WO | WO-2014/168874 A2 | 10/2014 |
| WO | WO-2014/180490 A1 | 11/2014 |
| WO | WO-2014/180569 A1 | 11/2014 |
| WO | WO-2015/014375 A1 | 2/2015 |
| WO | WO 2015/014869 A1 | 2/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/043613 A1 | 4/2015 |
| WO | WO-2015/051169 A2 | 4/2015 |
| WO | WO-2015/051173 A2 | 4/2015 |
| WO | WO-2015/058780 A1 | 4/2015 |
| WO | WO-2015/085318 A2 | 6/2015 |
| WO | WO-2015/089511 A2 | 6/2015 |
| WO | WO-2015/117620 A1 | 8/2015 |
| WO | WO-2015/164674 A1 | 10/2015 |
| WO | WO-2015/172843 A1 | 11/2015 |
| WO | WO-2016/062323 A1 | 4/2016 |
| WO | WO-2016/091391 A1 | 6/2016 |
| WO | WO-2016/107877 A1 | 7/2016 |
| WO | WO-2016/128060 A1 | 8/2016 |
| WO | WO 2016/128376 A1 | 8/2016 |
| WO | WO-2016/155809 A1 | 10/2016 |
| WO | WO-2017/106638 A1 | 6/2017 |
| WO | WO-2018/195357 A1 | 10/2018 |
| WO | WO-2018/224166 A1 | 12/2018 |
| WO | WO-2018/224405 A1 | 12/2018 |

(56) References Cited

FOREIGN PATENT DOCUMENTS

| WO | WO-2018/227030 A1 | 12/2018 |
|---|---|---|
| WO | WO-2019/050994 A1 | 3/2019 |
| WO | WO-2019/075112 A1 | 4/2019 |
| WO | WO-2019/104203 A1 | 5/2019 |
| WO | WO-2019/168984 A1 | 9/2019 |

OTHER PUBLICATIONS

International Preliminary Report on Patentability for PCT/EP18/64468 (Methods for Predicting the Usefulness of Disease Specific Amino Acid Modifications for Immunotherapy, filed Jun. 1, 2018), received by ISA/EP, 6 pages (Jul. 6, 2018).
International Preliminary Report on Patentability for PCT/EP2017/064140, (Methods for Predicting the Usefulness of Disease Specific Amino Acid Modifications for Immunotherapy, filed Jun. 9, 2017) received by ISA/EP, 6 pages (Mar. 21, 2018).
International Search Report for PCT/EP18/64468 (Methods for Predicting the Usefulness of Disease Specific Amino Acid Modifications for Immunotherapy, filed Jun. 1, 2018), received by ISA/EP, 5 pages (Jul. 6, 2018).
International Search Report for PCT/EP2017/064140, (Methods for Predicting the Usefulness of Disease Specific Amino Acid Modifications for Immunotherapy, filed Jun. 9, 2017) received by ISA/EP, 5 pages (Mar. 21, 2018).
Jorgensen, L. et al., Recent trends in stabilising peptides and proteins in pharmaceutical formulation—considerations in the choice of excipients, Expert Opin. Drug Deliv., 6(11):1219-1230 (2009).
Muralidhara, B. K. et al., Critical considerations for developing nucleic acid macromolecule based drug products, Drug Discovery Today, 21(3):430-444 (2016).
Written Opinion for PCT/EP18/64468 (Methods for Predicting the Usefulness of Disease Specific Amino Acid Modifications for Immunotherapy, filed Jun. 1, 2018), received by ISA/EP, 5 pages (Jul. 6, 2018).
Written Opinion for PCT/EP2017/064140, (Methods for Predicting the Usefulness of Disease Specific Amino Acid Modifications for Immunotherapy, filed Jun. 9, 2017) received by ISA/EP, 5 pages (Mar. 21, 2018).
Morse, M. et al., An Alphavirus vector overcomes the presence of neutralizing antibodies and elevated numbers of Tregs to induce immune responses in humans with advanced cancer, The Journal of Clinical Investigation, 120(9):3234-3241 (2010).
Abastado, J.P. et al., Differential role of conserved and polymorphic residues of the binding groove of MHC class I molecules in the selection of peptides, J Immunol., 151(7):3569-75 (1993).
Abrams, S. et al., Identification of overlapping epitopes in mutant ras oncogene peptides that activate CD4+ and CD8+ T cell responses, Eur. J. Immunol., 26:435-443 (1996).
Adzhubei, A. et al., A method and server for predicting damaging missense mutations. Nat Methods. 7(4):248-9 (2010).
Ajay, S. et al., Accurate and comprehensive sequencing of personal genomes, Genome Res., 21(9):1498-505 (2011).
Allard, W.J. et al., Tumor cells circulate in the peripheral blood of all major carcinomas but not in healthy subjects or patients with nonmalignant diseases, Clin Cancer Res., 10(20):6897-904 (2004).
Anderson, M. and Schrijver, I., Next generation DNA sequencing and the future of genomic medicine, Genes (Basel), 1(1):38-69 (2010).
Arnold, P.Y. et al., The majority of immunogenic epitopes generate CD4+ T cells that are dependent on MHC class II-bound peptide-flanking residues, J Immunol., 169(2):739-49 (2002).
Bainbridge, M. et al., Whole exome capture in solution with 3 Gbp of data, Genome Biol., 11(6):R62 (2010).
Bentley, D. et al., Accurate whole human genome sequencing using reversible terminator chemistry, Nature, 456(7218):53-59 (2008). (Author Manuscript).
Berensmeier, Sonja, Magnetic particles for the separation and purification of nucleic acids, Appl Microbiol Biotechnol., 73(3):495-504 (2006).
Berger, M. et al., Integrative analysis of the melanoma transcriptome, Genome Res., 20(4):413-27 (2010).
Bijker, M. et al., CD8+ CTL priming by exact peptide epitopes in incomplete Freund's adjuvant induces a vanishing CTL response, whereas long peptides induce sustained CTL reactivity, J Immunol., 179(8):5033-40 (2007).
Bloom, M. et al., Identification of tyrosinase-related protein 2 as a tumor rejection antigen for the B16 melanoma, J Exp Med., 185(3):453-9 (1997).
Bobisse, S. et al., Neoantigen-based cancer immunotherapy, Ann Transl Med., 4(14):262 (2016).
Boczkowski, D. et al., Dendritic cells pulsed with RNA are potent antigen-presenting cells in vitro and in vivo, J Exp. Med., 184:465-472 (1996).
Bogojeska et al. Rtreemix: an R package for estimating evolutionary pathways and genetic progression scores Bioinformatics, 24(20);2391-2392 (2008).
Boisguérin, V. et al., Translation of genomics-guided RNA-based personalised cancer vaccines: towards the bedside, Br J Cancer, 111(8):1469-75 (2014).
Bowerman, N. et al., Engineering the binding properties of the T cell receptor: peptide: MHC ternary complex that governs T cell activity, Mol. Immun., 46:3000-3008 (2009).
Brennick et al., Neoepitopes as cancer immunotherapy targets: key challenges and opportunities, Immunotherapy, 9(4):361-371 (2017).
Brickner, A. et al., The immunogenicity of a new human minor histocompatibility antigen results from differential antigen processing, J Exp Med., 193(2):195-206 (2001).
Brinckerhoff, L. et al., Melanoma vaccines, Current Opinion Oncology, 12(2):163-173 (2000).
Brochet, X. et al., IMGT/V-QUEST: the highly customized and integrated system for IG and TR standardized V-J and V-D-J sequence analysis, Nucleic Acids Res., 36:W503-8 (2008).
Buckwalter, M. and Srivastava, P., It is the antigen(s), stupid and other lessons from over a decade of vaccitherapy of human cancer, Semin Immunol, 20(5):296-300 (2008).
Byers, Tim, What can randomized controlled trials tell us about nutrition and cancer prevention?, CA Cancer J Clin., 49(6):353-61 (1999).
Campbell, P. et al., The patterns and dynamics of genomic instability in metastatic pancreatic cancer, Nature, 467(7319):1109-13 (2010).
Carbone, D. et al., Immunization with mutant p53- and K-ras-derived peptides in cancer patients: immune response and clinical outcome, J Clin Oncol., 23(22):5099-107 (2005).
Carralot, J. et al., Production and characterization of amplified tumor-derived cRNA libraries to be used as vaccines against metastatic melanomas, Genetic Vaccines and Therapy, 3(6): 10 pages (2005).
Carreno, B.M. et al., Cancer immunotherapy. A dendritic cell vaccine increases the breadth and diversity of melanoma neoantigen-specific T cells, Science, 348(6236):803-8 (2015).
Carter, P. et al., Identification and validation of cell surface antigens for antibody targeting in oncology, Endocrine-Related Cancer, 11(4):659-687 (2004).
Chang, S. et al., Peptide length-based prediction of peptide-MHC class II binding, Bioinformatics, 22(22):2761-2767 (2006).
Choi, M. et al., Genetic diagnosis by whole exome capture and massively parallel DNA sequencing, Proc Natl Acad Sci USA, 106(45):19096-101 (2009).
Communication (1) of a notice of opposition for EP12723117.3, 34 pages (Apr. 20, 2020).
Communication (2) of a notice of opposition for EP12723117.3, 34 pages (Apr. 20, 2020).
Communication of a notice of opposition for EP12723117.3, 33 pages (Apr. 17, 2020).
Culshaw, S. et al., Assessment of Human Immune Response to Mutans Streptococcal Glucosyltransferase Peptides Selected by MHC Class II Binding Probability, International Journal of Peptide Research and Therapeutics, 13(4):525-531 (2007).
Decision Revoking the European Patent (Art. 101(2) and 101(3)(b) EPC) for EP11781409.5 (EP 2569633B) and associated documents, 39 pages (Nov. 5, 2018).

(56) References Cited

OTHER PUBLICATIONS

Delamarre, L. et al., Cancer immunotherapy. Neo approaches to cancer vaccines, Science, 348(6236):760-1 (2015).
Doctoral Thesis by Marc Günder, 216 pages (2012). [Non-English copy].
Dudley, M.E., et al., Generation of tumor-infiltrating lymphocyte cultures for use in adoptive transfer therapy for melanoma patients, J Immunother., 26(4):332-42 (2003).
Ecke, T. et al., TP53 Gene Mutations in Prostate Cancer Progression, Anticancer Research, 30:1579-1586 (2010).
Greenblatt, M. et al., Detailed computational study of p53 and p16: using evolutionary sequence analysis and disease-associated mutations to predict the functional consequences of allelic variants, Oncongene, 22:1150-1163 (2003).
Grudzien-Nogalska, E. et al., Synthetic mRNAs with superior translation and stability properties, Methods Mol Biol., 969:55-72 (2013).
Gubin, M.M. et al., Checkpoint blockade cancer immunotherapy targets tumour-specific mutant antigens, Nature, 515(7528):577-81 (2014).
Hacohen, N. et al., Getting Personal with Neoantigen-Based Therapeutic Cancer Vaccines, Cancer Immunol Res, 1:11-15 (2013). (Author Manuscript).
Hirano, J. et al., Hepatitis C virus modulates signal peptide peptidase to alter host protein processing, Proc Natl Acad Sci USA, 118(22):e2026184118, 12 pages (2021).
Hodges, E. et al., Genome-wide in situ exon capture for selective resequencing, Nat Genet., 39(12):1522-7 (2007).
Hodis, E. et al., A landscape of driver mutations in melanoma, Cell, 150(2):251-63 (2012).
Holtkamp, S. et al., Modification of antigen-encoding RNA increases stability, translational efficacy, and T-cell stimulatory capacity of dendritic cells, Blood, 108(13):4009-17 (2006).
Hoyt, M.A. et al., Glycine-alanine repeats impair proper substrate unfolding by the proteasome, EMBO J., 25(8):1720-9 (2006).
International Search Report for PCT/EP2015/053021, 6 pages (Aug. 18, 2016).
International Search Report for PCT/EP2016/052684, 6 pages (Aug. 18, 2016).
Jordan, K. et al., Peptide vaccines prevent tumor growth by activating T cells that respond to native tumor antigens, PNAS, 107(10):4652-4657 (2010).
Kartikasari, A. et al., Therapeutic Cancer Vaccines—T Cell Responses and Epigenetic Modulation, Frontiers in Immunology, 9:1-15 (2019).
Katsnelson, Alla, Mutations as munitions: Neoantigen vaccines get a closer look as cancer treatment, Nat Med., 22(2):122-4 (2016).
Kawakami, Y. et al., Identification of human tumor antigens and its implications for diagnosis and treatment of cancer, Cancer Sci, 95(10):784-791 (2004).
Kent, James W., BLAT—the BLAST-like alignment tool, Genome Res., 12(4):656-64 (2002).
Kim, Y. et al., Immune epitope database analysis resource, Nucleic Acids Res., 40:W525-30 (2012).
Koido, S. et al., Treatment with Chemotherapy and Dendritic Cells Pulsed with Multiple Wilms' Tumor 1 (WT1)-Specific MHC Class I/II-Restricted Epitopes for Pancreatic Cancer, Clinical Cancer Research, 20(16):4228-4239 (2014).
Koressaar, T. and Remm, M., Enhancements and modifications of primer design program Primer3, Bioinformatics, 23(10):1289-91 (2007).
Kranz, L.M. et al., Systemic RNA delivery to dendritic cells exploits antiviral defence for cancer immunotherapy, Nature, 534(7607):396-401 (2016).
Kreiter, S. et al., Increased antigen presentation efficiency by coupling antigens to MHC class I trafficking signals, J Immunol., 180(1):309-18 (2008).
Kronenberger, K. et al., A polyvalent cellular vaccine induces T-cell responses against specific self-antigens overexpressed in chronic lymphocytic B-cell leukemia, J Immunother, 31(8):723-730 (2008).
Kuhn, A.N. et al., Phosphorothioate cap analogs increase stability and translational efficiency of RNA vaccines in immature dendritic cells and induce superior immune responses in vivo, Gene Ther., 17(8):961-71 (2010).
Langmead, B. et al., Ultrafast and memory-efficient alignment of short DNA sequences to the human genome, Genome Biol., 10(3):R25 (2009).
Lawrence, M.S. et al., Mutational heterogeneity in cancer and the search for new cancer-associated genes, Nature, 499(7457):214-218 (2013).
Le Calvez-Kelm, F. et al., Rare, evolutionarily unlikely missense substitutions in CHEK2 contribute to breast cancer susceptibility: results from a breast cancer family registry case-control mutation-screening study, Breast Cancer Research, 13:R6, 12 pages (2011).
Le, D.T et al., PD-1 Blockade in Tumors with Mismatch-Repair Deficiency, N Engl J Med., 372(26):2509-20 (2015).
Li, H. and Durbin, R., Fast and accurate short read alignment with Burrows-Wheeler transform, Bioinformatics, 25(14):1754-60 (2009).
Linard, B. et al., A ras-mutated peptide targeted by CTL infiltrating a human melanoma lesion, J Immunol., 168(9):4802-4808 (2002).
Lundegaard, C. et al., NetMHC-3.0: accurate web accessible predictions of human, mouse and monkey MHC class I affinities for peptides of length 8-11, Nucleic Acids Research, 36:w509-w512, (2008).
Lundegaard, C. et al., State of the art and challenges in sequence based T-cell epitope prediction, Immunome Res., 6 Suppl 2(Suppl 2):S3 (2010).
Malcikova, J. et al., Identification of somatic hypermutations in the TP53 gene in B-cell chronic lymphocytic leukemia, Mol Immunol., 45(5):1525-1529 (2008).
Maloy, K.J. et al., Intralymphatic immunization enhances DNA vaccination, Proc Natl Acad Sci USA, 98(6):3299-303 (2001).
Mardis, E. and Wilson, R., Cancer genome sequencing: a review, Hum Mal Gen, 18:R163-R168 (2009).
Margulies, M., Genome Sequencing in Open Microfabricated High Density Picoliter Reactors, Nature, 437:376-380 (2005).
Mcgranahan, N. et al., Clonal neoantigens elicit T cell immunoreactivity and sensitivity to immune checkpoint blockade, Science, 351(6280):1463-9 (2016).
Meleif, C. and Van Der Burg, S., Immunotherapy of established (pre)malignant disease by synthetic long peptide vaccines, Nature Reviews, 8:351-360 (2008).
Men, Y. et al., Assessment of Immunogenicity of Human Melan-A Peptide Analogues in HLA-A*0201/Kb Transgenic Mice, The Journal of Immunology, 162(6):3566-3573 (1999).
Mortazavi, A. et al., Mapping and quantifying mammalian transcriptomes by RNA-Seq, Nat Methods., 5(7):621-8 (2008).
Nagrath, S. et al., Isolation of rare circulating tumour cells in cancer patients by microchip technology, Nature, 450(7173):1235-9 (2007).
NG, P. et al., Genetic Variation in an Individual Human Exome, PLoS Gen., 4(8): 1-15, 2008.
Notice of Opposition to EP 2569633 B (Application No. EP11781409.5) and associated documents (Agenus Inc.), 20 pages (Nov. 9, 2016).
Notice of Opposition to EP 2569633 B (Application No. EP11781409.5) and associated documents (Dr. Christian Muller), 49 pages (Nov. 9, 2016).
Notice of Opposition to EP 2569633 B (Application No. EP11781409.5) and associated documents (Gritstone Oncology, Inc.), 53 pages (Nov. 7, 2016).
Notice of Opposition to EP 2569633 B (Application No. EP11781409.5) and associated documents (James Poole Limited), 35 pages (Nov. 9, 2016).
Notice of Opposition to EP 2569633 B (Application No. EP11781409.5) and associated documents (Strawman Limited), 39 pages (Nov. 10, 2016).
Novellino et al., A listing of human tumor antigens recognized by T cells: Mar. 2004 update, Cancer Immunol Immunother, 2005, 54: 187-207.
Omokoko, T.A., et al., Luciferase mRNA Transfection of Antigen Presenting Cells Permits Sensitive Nonradioactive Measurement of Cellular and Humoral Cytotoxicity, J Immunol Res., 9540975, 13 pages (2016).

(56) References Cited

OTHER PUBLICATIONS

Otrashewvskaya, E.V. et al., Progress in the Development of Vaccines for the Prevention of Chikungunya Disease and Outlooks for Market Appearance, BIOproducts, Prevention, Diagnostics, Treatment, 23 pages English Abstract (2023).
Ott, P. et al., Vaccines and melanoma, Hematol Oncol Clin North Am, 28(3):559-569 (2014).
Overwijk, W. et al., Mining the mutanome: developing highly personalized Immunotherapies based on mutational analysis of tumors, J Immunother Cancer, 1:11, 4 pages (2013).
Pascolo, S., Messenger RNA-based vaccines, Expert Opin. Biol. Ther., 4(8):1285-1294 (2004).
Pleasance, E. et al. A small-cell lung cancer genome with complex signatures of tobacco exposure. Nature, 463: 184-190, 2010.
Pleasance, E.D. et al., A comprehensive catalogue of somatic mutations from a human cancer genome, Nature, 463(7278):191-6 (2010).
Rajasagi, M. et al., Systematic identification of personal tumor-specific neoantigens in chronic lymphocytic leukemia, Blood, 124(3):453-462 (2014).
Rizvi, N. et al. Mutational landscape determines sensitivity to PD-1 blockade in non-small cell lung cancer, Cancer Immunology, 348(6230):124-128 (2014).
Rizvi, N.A. et al., Cancer immunology. Mutational landscape determines sensitivity to PD-1 blockade in non-small cell lung cancer, Science, 348(6230):124-8 (2015).
Robbins, P. et al., A mutated ß-catenin gene encodes a melanoma-specific antigen recognized by tumor infiltrating lymphocytes, J Exp Med., 183(3):1185-1192 (1996).
Robbins, P.F. et al., Mining exomic sequencing data to identify mutated antigens recognized by adoptively transferred tumor-reactive T cells, Nat Med., 19(6):747-52 (2013).
Ronaghi, M. et al., A sequencing method based on real-time pyrophosphate, Science, 281(5375):363, 365 (1998).
Saeterdal, I. et al., Frameshift-mutation-derived peptides as tumor-specific antigens in inherited and spontaneous colorectal cancer, Proc Natl Acad Sci USA, 98(23):13255-13260 (2001).
Sahin, U. and Tureci, O., Personalized vaccines for cancer immunotherapy, Science, 359:1355-1360 (2018).
Sallman, D. and Padron, E., Integrating mutation variant allele frequency into clinical practice in myeloid malignancies, Hematol Oncol Stem Cell Ther., 9:89-95 (2016).
Sampson, J. et al., An epidermal growth factor receptor variant III-targeted vaccine is safe and immunogenic in patients with glioblastoma multiforme, Mol Cancer Ther., 8(10):2773-2779 (2009).
Schaffner, C. et al., Somatic ATM mutations indicate a pathogenic role of ATM in B-cell chronic lymphocytic leukemia, Blood, 94(2):748-753 (1999).
Scheibenbogen, C. et al., Analysis of the T cell response to tumor and viral peptide antigens by an IFNγ-ELISPOT assay, Int. J. Cancer, 71:932-936 (1997).
Schietinger et al., Specificity in cancer immunotherapy, Semin Immunol., 2008, 20(5):276-285, Oct. 2008.
Schlessinger, A. and Rost, B., Protein flexibility and rigidity predicted from sequence, Proteins, 61(1):115-26 (2005).
Schoenberger, S.P. et al., T-cell help for cytotoxic T lymphocytes is mediated by CD40-CD40L interactions, Nature, 393(6684):480-3 (1998).
Schumacher, T. et al., A vaccine targeting mutant IDH1 induces antitumour immunity, Nature, 512:324-327 (2014).
Schumacher, T. N. and Schreiber, R. D., Neoantigens in cancer immunotherapy, Science, 348(6230): 69-74 (2015).
Schwitalle, Y. et al., Immunogenic peptides generated by frameshift mutations in DNA mismatch repair-deficient cancer cells, Cancer Immun., 4:14, 10 pages (2004).
Shirai, M. et al., Helper-cytotoxic T lymphocyte (CTL) determinant linkage required for priming of anti-HIV CD8+ CTL in vivo with peptide vaccine constructs, J Immunol., 152(2):549-56 (1994).
Simon, P. et al., Functional TCR retrieval from single antigen-specific human T cells reveals multiple novel epitopes, Cancer Immunol Res., 2(12):1230-44 (2014).
Singh-Jasuja, H. et al., The Tubingen approach: identification, selection, and validation of tumor-associated HLA peptides for cancer therapy, Cancer Immunol Immunother., 53:187-195 (2004).
Snyder, A. et al., Genetic basis for clinical response to CTLA-4 blockade in melanoma, N. Engl. J. Med., 371(23):2189-2199 (2014).
Srivastava, N. and Srivastava, P., Modeling the Repertoire of True Tumor-Specific MHC I Epitopes in a Human Tumor, Plos One, 4:1-7 (2009).
Stratton, M. et al., The cancer genome, Nature, 458(7239):719-724 (2009).
Suhrbier, Andreas, Multi-epitope DNA vaccines, Immunology and Cell Biology, 75:402-408 (1997).
Suhrbier, Andreas, Polytope vaccines for the codelivery of multiple CD8 T-cell epitopes, Expert Rev. Vaccines, 1(2):207-213 (2002).
Teer, J.K. and Mullikin, J.C., Exome sequencing: the sweet spot before whole genomes, Hum Mol Genet., 19(R2):R145-51 (2010).
Tong, J. C. et al., Methods and protocols for prediction of immunogenic Briefings in Bioinformatics, 8(2):96-108 (2006).
Tourdot, S. et al., A general strategy to enhance immunogenicity of low-affinity HLA-A2.1-associated peptides: implication in the identification of cryptic tumor epitopes, Eur. J. Immunol., 30(12):3411-3421 (2000).
Tran, E. et al., Cancer immunotherapy based on mutation-specific CD4+ T cells in a patient with epithelial cancer, Science, 344(6184):641-5 (2014).
Tran, E. et al., T-Cell Transfer Therapy Targeting Mutant KRAS in Cancer, N Engl J Med., 375(23):2255-2262 (2016).
Tureci, O. et al., Targeting the Heterogeneity of Cancer with Individualized Neoepitope Vaccines, Clin Cancer Res., 22(8):1885-96 (2016).
Untergasser, A., et al., Primer3—new capabilities and interfaces, Nucleic Acids Res., 40(15):e115 (2012).
Van Allen, E.M. et al., Genomic correlates of response to CTLA-4 blockade in metastatic melanoma, Science, 350(6257):207-211 (2015).
Van Rooji, N. et al., Tumor exome analysis reveals neoantigen-specific T-cell reactivity in an ipilimumab-responsive melanoma, J Clin Oncol., 31(32):e439-e442 (2013).
Voelkerding, K.V. et al., Next-generation sequencing: from basic research to diagnostics, Clin Chem., 55(4):641-58 (2009).
Volpe, G. et al., Alternative BCR/ABL splice variants in Philadelphia chromosome-positive leukemias result in novel tumor-specific fusion proteins that may represent potential targets for immunotherapy approaches, Cancer Res., 67(11):5300-5307 (2007).
Vormehr, M. et al., Mutanome Engineered RNA Immunotherapy: Towards Patient-Centered Tumor Vaccination, J. Immunol. Res., Article ID 595363, 6 pages (2015).
Wang, Rong-Fu, Tumor antigens discovery: perspectives for cancer therapy, Mol Med, 3(11):716-731 (1997).
Weinschenk, T. et al., Integrated Functional Genomics Approach for the Design of Patient-individual Antitumor Vaccines, Cancer Research, 62(20):5818-5827 (2002).
Wick, DA. et al., Surveillance of the tumor mutanome by T cells during progression from primary to recurrent ovarian cancer, Clin Cancer Res, 20(5):1125-34 (2014).
Wolchok, J.D., et al., Guidelines for the evaluation of immune therapy activity in solid tumors: immune-related response criteria, Clin Cancer Res., 15(23):7412-20 (2009).
Wood, L. et al., The Genome Landscapes of Human Breast and Colorectal Cancers, Science, 318(5853):1108-1113 (2007).
Written Opinion for PCT/EP2015/053021, 6 pages (Aug. 18, 2016).
Written Opinion for PCT/EP2016/052684, 5 pages (Aug. 18, 2016).
Yadav, M. et al., Predicting immunogenic tumour mutations by combining mass spectrometry and exome sequencing, Nature, 515(7528):572-6 (2014).
Yokoyama, Y, et al., Matrilysin (MMP-7) is a novel broadly expressed tumor antigen recognized by antigen-specific T cells, Clin Cancer Res, 14(17):5503-5511 (2008).
Zhang, J. et al., The impact of next-generation sequencing on genomics, J. Genet. Genomics, 38(3):95-109 (2011).

(56) References Cited

OTHER PUBLICATIONS

Zhang, M. and Coffino, P., Repeat sequence of Epstein-Barr virus-encoded nuclear antigen 1 protein interrupts proteasome substrate processing, J Biol Chem., 279(10):8635-41 (2004).
Zhu, S. et al., Improving MHC binding peptide prediction by incorporating binding data of auxiliary MHC molecules, Bioinformatics, 22(13):1648-55 (2006).
Agrawal, S., Antisense oligonucleotides: towards clinical trials, Trends Biotechnol., 14(10):376-87 (1996).
Aly, Hamdy A.A., Cancer Therapy and Vaccination, Journal of Immunological Methods, 382(1):1-23 (2012).
Azuma, M. et al., B70 antigen is a second ligand for CTLA-4 and CD28, Nature, 366(6450):76-9 (1993).
B16 Melanoma, https://en.wikipedia.org/wiki/B16_Melanoma, retrieved from the internet on Sep. 23, 2016, 3 pages.
Bansal, Vikas, A statistical method for the detection of variants from next-generation resequencing of DNA pools, Bioinformatics 26, 318-324 (2010).
Bei, R. and Scardino, A., TAA Polyepitope DNA-Based Vaccines: A Potential Tool for Cancer Therapy, Journal of Biomedicine and Biotechnology, 2010, 12 pages (2010).
Bei, R., et al., The use of a cationic liposome formulation (DOTAP) mixed with a recombinant tumor-associated antigen to induce immune responses and protective immunity in mice, J Immunother., 21(3):159-69 (1998).
Bocchia, M. et al., Antitumor Vaccination: Where We Stand, Haematologica, 85(11):1172-1206 (2000).
Breiman, Leo, Statistical Modeling: The Two Cultures, Statistical Science, 16(3):199-231 (2001).
Buonaguro, L. et al., Translating Tumor Antigens into Cancer Vaccines, Clinical and Vaccine Immunology, 18(1):23-34 (2011).
Cai, A. et al., Peptides Derived from Mutated BCR-ABL Elicit T Cell Immunity in CML Patients, Blood, 116(21):388-388 (2010).
Chang, H. et al., Exome Sequencing Reveals Comprehensive Genomic Alterations across Eight Cancer Cell Lines, PLOS ONE, 6(6): e21097, 9 pages (2011).
Chapman, M. et al., Applications of Next-Generation Sequencing to Blood and Marrow Transplantation, Biology of Blood and Marrow Transplantation, 18(1):S151-S160 (2012).
Chenchik, A. et al., Generation and use of high quality cDNA from small amounts of total RNA by SMART PCR, Gene Cloning and Analysis by RT-PCR, pp. 305-319 (1998).
Chmielecki, J. et al., Targeted next-generation sequencing of DNA regions proximal to a conserved GXGXXG signaling motif enables systematic discovery of tyrosine kinase fusions in cancer, Nucleic Acids Research, pp. 1-12 (2020).
Conry, R. et al., Characterization of a messenger RNA polynucleotide vaccine vector, Cancer Res,. 55:1397-1400 (1995).
Conry, R. et al., Immune response to a carcinoembryonic antigen polynucleotide vaccine, Cancer Res., 54:1164-1168 (1994).
Coulie, P. et al., A mutated intron sequence codes for an antigenic peptide recognized by cytolytic T lymphocytes on a human melanoma, Proc. Natl. Acad. Sci. USA, 92:7976-7980 (1995).
Dahl, F. et al., Multigene amplification and massively parallel sequencing for cancer mutation discovery, PNAS, 104:9387-9392 (2007).
Dang, C. et al., Replacement Matrix: a web server for maximum-likelihood estimation of amino acid replacement rate matrices, Bioinformatics, 27(19):2758-2760 (2011).
Datta, S. et al., A Subset of Toll-Like Receptor Ligands Induces Cross-presentation by Bone Marrow-Derived Dendritic Cells, J Immunol, 170:4102-10 (2003).
De Groot A. and Moise L., Prediction of immunogenicity for therapeutic proteins: state of the art, Curr Opin Drug Discov Devel., 10(03):332-340 (2007).
Del Val, M. et al., Efficient Processing of an Antigenic Sequence for Presentation by MHC Class I Molecules Depends on Its Neighboring Residues in the Protein, Cell, 66(6,):1145-1153 (1991).
Dengjel, J et al., Glycan side chains on naturally presented MHC class II ligands, J Mass Spectrom, 40:100-104 (2005).
Dennis, Carina, Off by a whisker, Nature, 442:739-741 (2006).
Depristo, M. et al., A framework for variation discovery and genotyping using next-generation DNA sequencing data, Nature Genetics 43, 491-498 (2011).
Dey, N. et al., The Protein Phosphatase Activity of PTEN Regulates Src Family Kinases and Controls Glioma Migration, Cancer Res., 68:1862-71 (2008).
Ding, F. et al., Multiepitope Peptide-Loaded Virus-Like Particles as a Vaccine Against Hepatitis B Virus-Related Hepatocellular Carcinoma, Hepatology, 49(5):1492-1502 (2009).
Ding, L. et al., Analysis of next-generation genomic data in cancer: accomplishments and challenges, Human Molecular Genetics, 19(2):R188-R196 (2010).
Ding, L. et al., Genome remodeling in a basal-like breast cancer metastasis and xenograft, Nature, 464:999-1005 (2010).
Dolgin, Elie, The Billion-Dollar Biotech, Nature, 522:26-28 (2015).
Druley, T.E. et al., Quantification of rare allelic variants from pooled genomic DNA, Nature Methods, 6(4):263-265 (2009).
Echchakir, H. et al., A Point Mutation in the α-Actinin-4 Gene Generates an Antigenic Peptide Recognized by Autologous Cytolytic T Lymphocytes on a Human Lung Carcinoma, Cancer Res, 61:4078-83 (2001).
Ewen, K. et al., Identification and Analysis of Error Types in High-Throughput Genotyping, Am. J. Hum. Genet., 67:727-736 (2000).
Fawcett, Tom, An introduction to ROG analysis, Pattern Recognition Letters, 27(8):861-874 (2006).
Feng, D.F. et al., Aligning amino acid sequences: comparison of commonly used methods, J Mol. Evol., 21(2):112-125 (1985).
Florea et al., Proceedings of Computational System Bioinformatics, 2:1-10 (2003).
Fotin-Mleczek, M. et al., Messenger RNA-based Vaccines With Dual Activity Induce Balanced TLR-7 Dependent Adaptive Immune Responses and Provide Antitumor Activity, J. Immunotherapy; 34(1):1-15 (2011).
Fritsch, E. et al., HLA-Binding Properties of Tumor Neoepitopes in Humans, Cancer Immunology Research, 2:522-529 (2014).
Frumkin, D. et al., Cell Lineage Analysis of a Mouse Tumor, Cancer Research 68:5924-5931 (2008).
Fujita, P. et at., The UCSC Genome Browser database: update 2011, Nucleic Acids Research, 39:876-882 (2011).
Gjertsen, Marianne K., Mutated ras peptides as vaccines in immunotherapy of cancer, Vox Sanguinis, 74(2):489-495 (1998).
Gnirke, A. et al., Solution hybrid selection with ultra-long oligo-nucleotides for massively parallel targeted sequencing, Nat. Biotechnol, 27:182-9 (2009).
Goya, R. et al., SNVMix: predicting single nucleotide variants from next-generation sequencing of tumors, Bioinformatics, 26:730-736 (2010).
Gryaznov, Sergei M., Oligonucleotide N3' → P5' phosphoramidates as potential therapeutic agents, Biochimica Biophysica Acta, 1489:131-140 (1999).
Gura, Trisha, Systems for Identifying New Drugs Are Often Faulty, Science, 278:1041-1042 (1997).
Guyre, P. et al., Increased potency of Fc-receptor-targeted antigens, Cancer Immuno. Immunother, 45:146-148 (1997).
Hacohen Declaration dated Feb. 16, 2014 filed in U.S. Appl. No. 13/108,610, 10 pages.
Hajra, K. M. and Liu, J.R., Apoptosome dysfunction in human cancer, Apoptosis, 9:691-704 (2004).
Hall, S.S., IL-12 at the crossroads, Science, 268:1432-1434 (1995).
Hansen, K. et al., Biases in Illumina transcriptome sequencing caused by random hexamer priming, Nucleic Acids. Research, 38(12):, e131, 7 pages (2010).
Hart, C. et al., Single-Molecule Sequencing: Sequence Methods to Enable Accurate Quantitation, Methods in Enzymology, 472:407-430 (2010).
Hoerr, I. et al., In vivo application of RNA leads to induction of specific cytotoxic T lymphocytes and antibodies, Eur. J. Immunol., 30:1-7 (2000).
International Preliminary Report for Patentability for PCT/EP2014/001232, 7 pages (May 7, 2014).

(56) References Cited

OTHER PUBLICATIONS

International Preliminary Report on Patentability for PCT/EP2011/002576, 7 pages (May 24, 2011).
International Preliminary Report on Patentability for PCT/EP2012/002209, 14 pages (May 23, 2012).
International Preliminary Report on Patentability for PCT/EP2012/002209, 14 pages (Nov. 26, 2013).
International Preliminary Report on Patentability for PCT/EP2013/001400, 7 pages (May 10, 2013).
International Preliminary Report on Patentability for PCT/EP2016/052684, 6 pages (Aug. 24, 2017).
International Search Report for PCT/EP2011/002576, 5 pages (Apr. 5, 2012).
International Search Report for PCT/EP2012/002209, 14 pages (May 8, 2013).
International Search Report for PCT/EP2013/001400, 5 pages (May 10, 2013).
International Search Report for PCT/EP2013/003559, 5 pages, (Feb. 4, 2014).
International Search Report for PCT/EP2014/001232, 5 pages (May 7, 2014).
International Search Report for PCT/US2015/049491, 5 pages (Dec. 23, 2015).
Jia, J. et al., Genome-scale search of tumor-specific antigens by collective analysis of mutations, expressions and T-cell recognition, Molecular Immunology, 46(8-9):1824-1829 (2009).
Jiang, F. et al. Construction of Evolutionary Tree Models for Renal Cell Carcinoma from Comparative Genomic Hybridization Data Cancer Research; 60:6503-6509 (2000).
Johanning, F.W. et al., A sindbis virus mRNA polynucleotide vector achieves prolonged and high level heterologous gene expression in vivo, Nucleic Acids Res., 23(9):1495-1501 (1995).
Kenter, G.G. et al., Phase I Immunotherapeutic Trial with Long Peptides Spanning the E6 and E7 sequences of High-risk human papillomavirus 16 in End-stage cervical cancer patients shows low toxicity and robust immunogenicity, Clinical Cancer Research, 14:169-177 (2008).
Keogh, E. et al., Identification of New Epitopes from Four Different Tumor-Associated Antigens: Recognition of Naturally Processed Epitopes Correlates with HLA-A*0201-Binding Affinity, J. Immunol., 167:787-796 (2001).
Kessler, JH and Melief, CJM, Identification of T-cell epitopes for cancer immunotherapy, Leukemia, 21:1859-1874 (2007).
Khalili, J. et al., In silico prediction of tumor antigens derived from functional missense mutations of the cancer gene census, Oncolmmunology, 1(8):1281-1289 (2012).
Kircher, M. et al., Improved base calling for the Illumina Genome Analyzer using maching learning strategies, Genome Biology, 10:R83, 9 pages (2009).
Kreiter, S. et al., Intranodal Vaccination with Naked Antigen-Encoding RNA Elicits Potent Prophylactic and Therapeutic Antitumoral Immunity, Microenvironment and Immunology, 70(22):9031-9039 (2010).
Kreiter, S. et al., Simultaneous ex vivo quantification of antigen-specific CD4+ and CD8+ T cell responses using in vitro transcribed RNA, Cancer Immunol Immunother, 56:1577-87 (2007).
Kreiter, S. et al., Targeting the tumor mutanome for personalized vaccination therapy, Oncolmmunology, 5:768-769 (2012).
Kreiter, S. et al., Tumor vaccination using messenger RNA: prospects of a future therapy. Current Opinion in Immunology, 23(3):399-406 (2011).
Krieg, A. et al., CpG motifs in bacterial DNA trigger direct B-cell activation, Nature, 374:546-549 (1995).
Kumar, P. et al., Predicting the effects of coding non-synonymous variants on protein function using the SIFT algorithm, Nature Protocols, 4:1073-81 (2009).
Lafuente E. and Reche, P., Prediction Of MHC-Peptide Binding: A Systematic And Comprehensive Overview, Current Pharmaceutical Design, 15(28):3209-3220 (2009).
Lassmann, T. et al., SAMStat: monitoring biases in next generation sequencing data, Bioinformatics 27(1):130-131 (2011).
Ledford, Heidi, Cancer mutations often misidentified in the clinic, Nature News, 3 pages (2015).
Lee. Y. et al., Cell cycle-regulated expression and subcellular localization of a kinesin-8 member human KIF18B, Gene, 466:16-25 (2010).
Lemmel, C. et al., Differential quantitative analysis of MHC ligands by mass spectrometry using stable isotope labeling, Nature Biotechnology, 22(4):450-454 (2004).
Lennerz, V. et al., The response of autologous T cells to a human melanoma is dominated by mutated heoantigens, PNAS, 102:16013-16018 (2005).
Ley, T. et al., DNA sequencing of a cytogenetically normal acute myeloid leukemia genome, Nature, 456:66-72 (2008).
Li, H. et al., The Sequence Alignment/Map format and SAMtools, Bioinformatics, 25(16):2078-2079 (2009).
Li, Heng, Improving SNP discovery by base alignment quality, BioInformatics, 27:1157-1158 (2011).
Li, L. et al., Cancer Genome Sequencing and Its Implications for Personalized Cancer Vaccines, Cancers, 3:4191-4211 (2011).
Löwer, M. et al., Confidence-Based Somatic Mutation of Evaluation and Prioritization. PLOS Computational Biology, 8(9): 11 pages (2012).
Lutz, M. et al., An advanced culture method for generating large quantities of highly pure dentritic cells from mouse bone marrow, J Immunol Methods, 223:77-92 (1999).
Mahvi, D. et al., DNA cancer vaccines: A gene gun approach, Immunology and Cell Biology, 75:456-460 (1997).
Maksyutov, A.Z. and Zagrebelnaya, E.S., ADEPT: a computer program for prediction of protein antigenic determinants, Comput. Appl. Biosci., 9(3):291-297 (1993).
Mandelboim, O. et al., Regression of established murine carcinoma metastases following vaccination with tumour-associated antigen peptides, Nature Medicine, 1(11):1179-1183 (1995).
Mardis, E. et al., Recurring Mutations Found by Sequencing an Acute Myeloid Leukemia Genome, New England J. Med., 361:1058-1066 (2009).
Martinon, F. et al., Induction of virus-specific cytotoxic T lymphocytes in vivo by liposome-entrapped mRNA, Eur. J. Immunol, 23:1719-1722 (1993).
Mateo, L. et al., An HLA-A2 polyepitope vaccine for melanoma immunotherapy, The Journal of Immunology, 163(7):4058-4063 (1999).
Mayer, A. et al., Liposomal transfection of squamous carcinoma cells of the head and neck with IL-2 and B7 plasmids inducing an autologous immune response in vitro, Anticancer Research, 25(6B):3917-3924 (2005).
McKenna, A. et al., The Genome Analysis Toolkit: A MapReduce framework for analyzing next-generation DNA sequencing data, Genome Research, 20:1297-303 (2010).
Meyerson, M. et al., Advances in understanding cancer genomes through second-generation sequencing, Nature Reviews, 11:685-695 (2010).
Michielin, O. and Karplus, M., Binding Free Energy Differences In A TRC-Peptide-MHC Complex Induced By A Peptide Mutation: A Simulation Analysis, Journal of Molecular Biology, 324(3):547-569 (2002).
Monach, P. et al., A unique tumor antigen produced by a single amino acid substitution, Immunity, 2:45-59 (1995).
Nakamura, K. et al., Sequence-specific error profile of Illumina sequencers, Nucleic Acids Research, 39(13):e90, 13 pages (2011).
Navin, N. et al., Tumour evolution inferred by single-cell sequencing, Nature, 472:90-95 (2011).
Nielsen, J. et al., An in vitro-transcribed-mRNA polyepitope construct encoding 32 distinct HLA class I-restricted epitopes from CMV, EBV, and Influenza for use as a functional control in human immune monitoring studies, Journal of Immunological Methods, 360:149-156 (2010).
Nielsen, M. et al., NetMHCpan, a Method for Quantitative Predictions of Peptide Binding to Any HLA-A and -B Locus Protein of Known Sequence, PLoS ONE, 2(8), 8 pages (2007).

(56) References Cited

OTHER PUBLICATIONS

No Author Listed, The problem with neoantigen prediction, Nat Biotechnol, 35(2):97 (2017).
Nothnagel, M. et al., Technology-specific error signatures in the 1000 Genomes Project data, Hum Genet., 130:505-516 (2011).
Pantel, K. et al., Circulating tumour cells in cancer patients: challenges and perspectives, Trends in Molecular Medicine, 16(9):398-406 (2010).
Parker, K.C. et al., Scheme for ranking potential HLA-A2 binding peptides based on independent binding of individual peptide side-chains, J. Immunol., 152:163-175 (1994).
Parkhurst, M.R. et al., Improved Induction of Melanoma-reactive CTL with peptides from the melanoma antigen gp100 modified at HLA-A*0201-binding residues, J Immunol., 157:2549-2548 (1996).
Parmiana, G. et al., Unique Human Tumor Antigens: Immunobiology and Use in Clinical Trials, The Journal of Immunology, 178:1975-1979 (2007).
Perissi, I. et al., Electron Spin Resonance and Differential Scanning Calorimetry as Combined Tools for the Study of Liposomes in the Presence of Long Chain Nitroxides, J. Phys. Chem. B, 106:10468-10473 (2002).
Pfohl, T. et al., Biological Polyelectrolyte Complexes in Solution and Confined on Patterned Surfaces, Colloids and Surfaces A: Physicochemical and Engineering Aspects, 198-200:613-623 (2002).
Pilla, L. et al., Multipeptide vaccination in cancer patients, Expert Opinion on Biological Therapy, 9:1043-1055 (2009).
Pokrovskaya, I. and Gurevich, V., In Vitro Transcription: Preparative RNA Yields in Analytical Scale Reactions, Analytical Biochemistry, 220:420-423 (1994).
Pruitt, K. et al., NCBI reference sequences (RefSeq): a curated non-redundant sequence database of genomes, transcripts and proteins, Nucleic Acids Research, 35:D61-D65 (2007).
Qin, H. et al., Enhancement of antitumour immunity by a novel chemotactic antigen DNA vaccine encoding chemokines and multiepitopes of prostate-tumour-associated antigens, Immunology, 117:419-430 (2006).
Rahma, O. et al., A pilot clinical trial testing mutant van Hippel-Lindau peptide as a novel immune therapy in metastatic renal Cell Carcinoma, Journal of Translational Medicine, 8(1), 9 pages (2010).
Rammansee, Chapter 50: Cancer Vaccines: Some Basic Considerations, Genomic and Personalized Medicine, Hungtington and Ginsburg. E-published on Nov. 11, 2008, 17 pages.
Rammensee et al. (2008). Cancer Vaccines: Some Basic Considerations, In Genomic and Personalized Medicine, vol. 1 (Eds.: Willard et al.), Elsevier, 573-589.
Rammensee, H. et al., SYFPEITHI: database for MHC ligands and peptide motifs, Immunogenentics, 50:213-219 (1999).
Rammensee, H. et al., Toward patient-specific tumor antigen selection for vaccination, Immunol. Rev. 188:164-176 (2002).
Rammensee, Hans-Georg, Some considerations on the use of peptides and mRNA for therapeutic vaccination against cancer, Immunol Cell Biol. 84(3):290-4 (2006).
Rao, C. et al., Expression of epithelial cell adhesion molecule in carcinoma cells present in blood and primary and metastatic tumors, International Journal of Oncology, 27:49-57 (2005).
Rao, Kanury V.S., Epitope-based vaccines: One Step at a Time, Proc. Indian natn. Sci. Acad., B60(5):419-424 (1994).
Reagan-Shaw, S. et al., Dose translation from animal to human studies revisited, The FASEB Journal, 22:659-661 (2007).
Ressing, M.E. et al., Human CTL epitopes encoded by human papillomavirus types 16 E6 and E7 identified through in vivo and in vitro immunogenicity studies of HLA-A*0201-binding peptides, The Journal of Immunology, 154:5934-5943 (1995).
Saenz-Badillos, J. et al., RNA as a tumor vaccine: a review of the literature, Exp Dermatol., 10(3):143-54 (2001).
Sahin, U. et al., Personalized RNA mutanome vaccines mobilize poly-specific therapeutic immunity against cancer, Nature, 547:222-226 (2017).
Schietinger, A. et al., Specificity in cancer immunotherapy, Semin Immunol., 20(5):276-285 (2008).
Schreurs, M. et al., Dentritic Cells Break Tolerance and Induce Protective Immunity against a Melanocyte Differentiation Antigen in an Autologous Melanoma Model, Cancer Research, 60:6995-7001 (2000).
Schulz, O. et al., Toll-like receptor 3 promotes cross-priming to virus-infected cells, Nature, 433:887-92 (2005).
Segal, N. et al., Epitope landscape in breast and colorectal cancer, Cancer Research, 68:889-892 (2008).
Sensi, M. and Anichini, A., Unique Tumor Antigens: Evidence for Immune Control of Genome Integrity and Immunogenic Targets for T Cell-Mediated Patient-Specific Immunotherapy, Clinical Cancer Research, 12(17):5023-5032 (2006).
Sette, A. et al. Peptide Binding to the Most Frequent HLA-A Class I Alleles Measured by Quantitative Molecular Binding Assays, Mol. Immunol., 31:813-822 (1994).
Sette, A. et al., The Relationship Between Class I Binding Affinity and Immunogenicity of Potential Cytotoxic T cell Epitopes, J Immunol., 153:5586-5592 (1994).
Shah, S. et al., Mutation of FOXL2 in granulosa-cell tumors of the ovary, N. Eng. J. Med., 360:2719-2729 (2009).
Sherry, S.T. et al., dbSNP: the NCBI database of genetic variation, Nucleic Acids Research, 29(1):308-311 (2001).
Sjöblom, T. et al., The Consensus Coding Sequences of Human Breast and Colorectal Cancers, Science, 314:268-274 (2006).
Smith, S. et al., Human Dendritic Cells Genetically Engineered to Express a Melanoma Polyepitope DNA Vaccine Induce Multiple Cytotoxic T-Cell Responses, Clinical Cancer Research, 7:4253-4261 (2001).
So, H. et al., Effect of a Novel Saponin Adjuvant Derived from Quillaja saponaria on the Immune Response to Recombinant Hepatitus B Surface Antigen, Mol. Cells, 7(2):178-186 (1997).
Srinivasan, R. and Wolchok, J., Tumor Antigens for Cancer Immunotherapy: Therapeutic Potential of Xenogeneic DNA Vaccines, Journal of Translational Medicine, 2(1), 12 pages (2004).
Stephens, P. et al., A screen of the complete protein kinase gene family identifies diverse patterns of somatic mutations in human breast cancer, Nature Genetics, 37:590-592 (2005).
Storey, John D., A direct approach to false discovery rates, J. R. Statist. Soc. B, 64(3):479-498 (2002).
Su, M.W. et al., Cognate peptide-induced destruction of CD8+ cytotoxic T lymphocytes is due to fratricide, The Journal of Immunology, 151:658-67 (1993).
Sun, et al., Therapeutic Effects of Tumor Antigen-Pulsed IL-2 Gene-Modified Dendritic Cells Combined with Low-Dose Cyclophosphamide on Matastatic Lung Carcinoma, Chinese Journal of Cancer Biotherapy, 1:45-49 (1999) English Abstract.
Suzuki, M. and Tarin, D., Gene expression profiling of human lymph node metastases and matched primary breast carcinomas: Clinical implications, Molecular Oncology, 1:172-180 (2007).
Taub, M. et al., Overcoming bias and systematic errors in next generation sequencing data, Genome Medicine, 2(87), 5 pages (2010).
Thomson, S. et al., Targeting a Polyepitope Protein Incorporating Multiple Class II-Restricted Viral Epitopes to the Secretary/Endocytic Pathway Faciliates Immune Recognition by CD4+ Cytotoxic T Lymphocytes: a Novel Approach to Vaccine Design, Journal of Virology, 72(3):2246-2252 (1998).
Toes, R. et al., Protective anti-tumor immunity induced by vaccination with recombinant adenoviruses encoding 9 multiple tumor-associated cytotoxic T lymphocyte epitopes in a string-of-beads fashion, Proc. Natl. Acad. Sci. USA, 94:14660-14665 (1997).
Toes, R.E. et al., Enhanced tumor outgrowth after peptide vaccination. Functional deletion of tumor-specific CTL induced by peptide vaccination can lead to the inability to reject tumors, The Journal of Immunology, 156:3911-8 (1996).
UniProtKB—P36888 (FLT3_HUMAN), last sequence update: Aug. 21, 2007, 10 pages.
UniProtKB—Q5SW79 (CE170_HUMAN), last sequence update: Dec. 21, 2004, 9 pages.
UniProtKB—Q9NVD7 (PARVA_HUMAN), last sequence update: Oct. 1, 2000, 25 pages.

(56) References Cited

OTHER PUBLICATIONS

Van Der Bruggen, P. et al., A gene encoding an antigen recognized by cytolytic T lymphocytes on a human melanoma, Science, 254:1643-1647 (1991).

Van Laere, A. et al. A regulatory mutation in IGF2 causes a major QTL effect on muscle growth in the pig, Nature, 425(6960):832-836 (2003).

Van Tassell, C. et al., SNP discovery and allele frequency estimation by deep sequencing of reduced representation libraries, Nature Methods 5(3):247-252 (2008).

Verhaak, R. et al., Integrated Genomic Analysis Identifies Clinically Relevant Subtypes of Bioblastoma Characterized by Abnormalities in PDGFRA, IDH1, EGFR, and NF1, Cancer Cell, 17:98-110 (2010).

Wan, S. et al., Large-Scale Molecular Dynamics Simulations of HLA-A*0201 Complexed with a Tumor-Specific Antigenic Peptide: Can the a3 and B2m Domains be Neglected?, Journal of Computational Chemistry, 25(15):1803-13 (2004).

Wan, S. et at., Molecular Basis Of Peptide Recognition By The TRC: Affinity Differences Calculated Using Large Scale Computing, Journal of Immunology, 175(3):1715-1723 (2005).

Warren, R. and Holt, R., A census of predicted mutational epitopes suitable for immunologic cancer control, Human Immunology, 71(3):245-254 (2010).

Waterston, R. et al., Initial sequencing and comparative analysis of the mouse genome, Nature, 420:520-562 (2002).

Wei, X et al., Exome sequencing identifies GRIN2A as frequently mutated in melanoma, Nat Genet,43:442-6 (2011).

Wolff, J. et al., Direct gene transfer into mouse muscle in vivo, Science 247:1465-1468 (1990).

Weide, B. et al., Results of the First Phase I/II Clinical Vaccination Trial With Direct Injection of mRNA, J. Immunother., 31(2):180-188 (2005).

Wortzel, R. et al., Multiple tumour-specific antigens expressed on a single tumour cell, Nature, 304:165-167 (1983).

Written Opinion of PCT/EP2011/002576, 6 pages (May 24, 2011).
Written Opinion of PCT/EP2012/002209, 13 pages (May 23, 2012).
Written Opinion of PCT/EP2013/001400, 6 pages (May 10, 2013).
Written Opinion of PCT/EP2014/001232, 6 pages (May 7, 2014).

Ya, Z. et al., Mouse Model for Pre-Clinical Study of Human Cancer Immunotherapy, Curr Protoc Immunol, 108, 53 pages (2016).

Zhang, Z and Gerstein, M., Patterns of nucleotide substitution, insertion and deletion in the human genome inferred from pseudogenes, Nucleic Acids Research, 31(18):5338-5348 (2003).

Zhao, B. et al., MHC-Peptide binding prediction for epitope based vaccine design, International Journal of Integrative Biology, 1(2):127-40 (2007).

Zhou, W. et al., RNA Melanoma Vaccine: Induction of Antitumor Immunity by Human Glycoprotein 100 mRNA Immunization, Human Gene Therapy, 10(16):2719-24 (1999).

Zilfou, J. and Lowe, S., Tumor Suppressive Functions of p53, Cold Spring Harbor Laboratory Press, 13 pages (2009).

Zwaveling, S. et al., Antitumor efficacy of wild-type p53-specific CD4(+) T-helper cells, Cancer Res., 62(21):6187-93 (2002).

Bergmann-Leitner, E. et al., Identification of a Human CD8+ T Lymphocyte Neo-epitope Created by a ras Codon 12 Mutation Which is Restricted by the HLA-A2 Allele, Cellular Immunology, 187:103-116 (1998).

\* cited by examiner

METHODS FOR PREDICTING THE USEFULNESS OF DISEASE SPECIFIC AMINO ACID MODIFICATIONS FOR IMMUNOTHERAPY

CROSS-REFERENCE TO RELATED APPLICATIONS

This application is a national stage filing under U.S.C. § 371 of PCT International Application No. PCT/EP2018/064468 filed Jun. 1, 2018, which claims foreign priority to PCT International Application No. PCT/EP2017/064140 filed Jun. 9, 2017, the contents of each of which are hereby incorporated by reference in their entirety.

TECHNICAL FIELD OF THE INVENTION

The present invention relates to methods for predicting whether peptides or polypeptides comprising disease specific amino acid modifications, in particular tumor-associated neo-antigens, comprise epitopes, in particular tumor-associated neo-epitopes, which are useful for immunotherapy such as for vaccination. The methods of the invention may be used, in particular, for the provision of vaccines which are specific for a patient's tumor and, thus, in the context of personalized cancer vaccines.

BACKGROUND OF THE INVENTION

The evolution of the immune system resulted in vertebrates in a highly effective network based on two types of defense: the innate and the adaptive immunity. In contrast to the evolutionary ancient innate immune system that relies on invariant receptors recognizing common molecular patterns associated with pathogens, the adaptive immunity is based on highly specific antigen receptors on B cells (B lymphocytes) and T cells (T lymphocytes) and clonal selection. While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors expressed on the surface of T cells. The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. To be able to target a vast variety of antigens, the T cell receptors need to have a great diversity.

Antigen-specific immunotherapy aims to enhance or induce specific immune responses in patients to control infectious or malignant diseases. The identification of a growing number of pathogen- and tumor-associated antigens led to a broad collection of suitable targets for immunotherapy. Cells presenting immunogenic peptides (epitopes) derived from these antigens can be specifically targeted by either active or passive immunization strategies. Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy; ACT).

Tumor vaccines aim to induce endogenous tumor specific immune responses by active immunization. Different antigen formats can be used for tumor vaccination including whole diseased cells, proteins, peptides or immunizing vectors such as RNA, DNA or viral vectors that can be applied either directly in vivo or in vitro by pulsing of dendritic cells (DCs) following transfer into the patient.

Somatic mutations in cancer are ideal targets for therapeutic vaccine approaches (Castle, J. C. et al. Cancer Res. 72, 1081-1091 (2012); Schumacher, T. N. & Schreiber, R. D. Science 348, 69-74 (2015); Türeci, O. et al. Clin. Cancer Res. 22, 1885-1896 (2016)). They can be processed into peptides, presented on the surface of tumor cells and recognized by T cells as neo-epitopes. Neo-epitopes are exempt from central immune tolerance and absent from healthy tissue, thus combining potentially strong immunogenicity with a lower likelihood of autoimmunity. Emerging data indicate that favorable clinical outcomes of clinical immunotherapies such as checkpoint blockade (Rizvi, N. A. et al. Science 348, 124-128 (2015); Snyder, A. et al. N. Engl. J. Med. 371, 2189-2199 (2014); Van Allen, E. M. et al. Science 350, 207-211 (2015); Le, D. T. et al. N. Engl. J. Med. 372, 2509-2520 (2015); Mcgranahan, N. et al. Science 351, 1463-1469 (2016)) and adoptive T-cell therapy (Tran, E. et al. Science 344, 641-645 (2014); Robbins, P. F. et al. Nat. Med. 19, 747-752 (2013); Tran, E. et al. N. Engl. J. Med. 375, 2255-2262 (2016)) are associated with neo-epitope immune recognition. We demonstrated in mouse tumor models, that a substantial fraction of the mutanome (i.e. the entirety of somatic mutations identified by next generation sequencing) is immunogenic and that these neo-epitopes are preferably recognized by $CD4^+$ T cells. Vaccines composed of neo-epitopes predicted in silica from mutanome data showed strong anti-tumor activity and induced complete rejection of established, aggressively growing mouse tumors (Kreiter, S. et al. Nature 520, 692-696 (2015)). Likewise, MHC class I neo-epitopes identified in mouse tumor models by exome and transcriptome analysis either alone or combined with mass spectrometry, appear to be suitable vaccine targets and tumor rejection antigens (Yadav, M. et al. Nature 515, 572-576 (2014); Gubin, M. M. et al. Nature 515, 577-581 (2014)). Altogether, these studies have created enthusiasm for neo-epitope vaccines (Carreno, B. M. et al. Science 348, 803-808 (2015); Bobisse, S., Foukas, P. G., Coukos, G. & Harari, A. Ann. Transl. Med. 4, 262 (2016); Katsnelson, A. Nat. Med. 22, 122-124 (2016); Delamarre, L., Mellman, I. & Yadav, M. Science 348, 760-1 (2015)).

In human cancer the vast majority of cancer mutations are unique to the individual patient, and therefore personalized treatment strategies are required. For each patient, the personal cancer mutation profile needs to be determined by deep sequencing to inform the composition of the individually tailored vaccine to be manufactured on demand.

Here, we report the first-in-human application of this personalized immunotherapy in patients with stage III and IV melanoma. We set up a process compliant with clinical development guidelines, which includes next generation sequencing for comprehensive identification of individual mutations from routine tumor biopsies, computational prediction of potentially relevant HLA class I and class II neo-epitopes, as well as design and manufacturing of a poly-neo-epitope RNA vaccine unique for each patient. Eligible patients started with a shared tumor antigen vaccine composed of NY-ESO-1 and Tyrosinase RNA until release of their personalized RNA vaccine. In total, 13 patients completed treatment, which was shown to be feasible, safe and well tolerated. The immunogenicity rate was surprisingly high. 60% of neo-epitopes were specifically recognized by vaccine-induced T cells. Each patient responded to at least three of their ten individual neo-antigens and a broad and diversified TCR repertoire was mobilized. Frequencies of neo-epitope specific T cells in the blood two to four weeks after start of vaccination ranged from low numbers requiring in vitro expansion to be detected, up to a high single-digit percentage. Brisk infiltrates with vaccine-induced neo-epitope reactive T cells and neo-epitope specific killing of autologous tumor cells were shown in the two patients with post-vaccination resected melanoma metastases.

Clinical evaluation of cumulative recurrent metastatic events in all patients revealed a highly significant decrease upon neo-epitope RNA vaccination as compared to the patients' prior disease history giving rise to a highly favorable clinical outcome with sustained progression free survival. One patient with multiple metastases treated only shortly with the neo-epitope vaccine due to fast tumor progression responded nearly instantly to subsequent PD-1 blockade and experienced complete response. Direct neo-epitope vaccine treatment related objective tumor regression was documented in two patients. One of these patients had a complete response of a progressive metastasis and continuing sustained disease control for 26 months. A second patient experienced an objective tumor response but despite the presence of poly-specific, fully functional neo-antigen reactive T cells had a late relapse.

The definition of suitable epitopes for immunotherapy remains a challenge. Thus, there is a need for a model to predict whether an epitope, in particular a neo-epitope, will be useful in immunotherapy.

Subtyping of the neo-epitope specific responses not only confirmed our previous finding of the high frequency of $CD4^+$ T-cell mediated recognition of immunogenic neo-epitopes (Kreiter, S. et al. Nature 520, 692-696 (2015)), but also showed $CD8^+$ T-cell responses against a quarter of the neo-epitopes used for the vaccines. The dominance of $CD4^+$ responses against mutations may be explained by the high promiscuity of the HLA class II molecule with respect to composition and length of the peptide ligand, whereas the highly specific HLA class I molecule binds a limited set of peptides of a narrow length distribution (Arnold, P. Y. et al. J. Immunol. 169, 739-49 (2002)). About two thirds of the observed CTL responses were directed against mutations that were concomitantly recognized by $CD4^+$ T cells reacting against a different position of the respective neo-epitope. As 50% of all neo-epitopes included into the vaccine exhibited a $CD4^+$ T-cell response, the observed linkage is most likely not a pure co-incidence of $CD4^+$ and CD8 neo-epitope immune responses. CTL epitopes that are covalently linked to helper epitopes are known to be more immunogenic (Shirai, M. et al. J. Immunol. 152, 549-556 (1994)). Mutations harboring HLA class I as well as class II neo-epitopes provide mechanistically favorable conditions for CTL priming, as $CD4^+$ T cells recognize their ligand on the DC that cross-presents the $CD8^+$ T cell neo-epitope and provide cognate T cell help by CD40L mediated DC activation (Schoenberger, S. P., Toes, R. E., van der Voort, E. I., Offringa, R. & Melief, C. J. Nature 393, 480-3 (1998)). On a related note, we also found that one and the same mutation may give rise to neo-epitopes presented on different HLA class I restriction elements and recognized by independent $CD8^+$ T cells (FIG. 3b). Likewise, we found that one and the same epitope/restriction element complex is recognized by neo-epitope specific T cells with different TCR clonotypes. These findings illustrate that an unexpectedly broad repertoire of mutation specific T cells may be recruited by neo-epitope vaccination and each single mutation leverages a diversity of T-cell specificities.

In summary, the findings presented herein demonstrate that the definition of suitable personalized neo-epitope vaccines, in particular personalized RNA neo-epitope vaccines may unfold a broad neo-antigen specific T-cell repertoire in cancer patients enabling an effective targeting of their mutanome.

DESCRIPTION OF INVENTION

Summary of the Invention

An aspect of the invention relates to a method for assessing the usefulness of a disease specific amino acid modification within a peptide or polypeptide expressed in a diseased cell for immunotherapy, the method comprising ascertaining whether the same or different fragments of the peptide or polypeptide comprising the disease specific amino acid modification are presented in the context of MHC molecules of different classes and/or when presented in the context of MHC molecules, preferably MHC molecules of different classes, are reactive with T cells restricted to different MHC classes.

In one embodiment, the MHC molecules of different classes are MHC class I molecules and MHC class II molecules and/or the T cells restricted to different MHC classes are CD4+ and CD8+ T cells. In one embodiment, presentation of the same or different fragments of the peptide or polypeptide comprising the disease specific amino acid modification in the context of MHC molecules of different classes and/or reactivity of the same or different fragments of the peptide or polypeptide comprising the disease specific amino acid modification when presented in the context of MHC molecules with T cells restricted to different MHC classes indicates that the disease specific amino acid modification is useful for immunotherapy.

Another aspect of the invention relates to a method for assessing the usefulness of a disease specific amino acid modification within a peptide or polypeptide expressed in a diseased cell for immunotherapy, the method comprising ascertaining whether a fragment of the peptide or polypeptide comprising the disease specific amino acid modification when presented in the context of the same MHC molecule is reactive with T cells having different T cell receptors.

In one embodiment, the different T cell receptors are of different clonotypes. In one embodiment, reactivity of a fragment of the peptide or polypeptide comprising the disease specific amino acid modification when presented in the context of the same MHC molecule with T cells having different T cell receptors indicates that the disease specific amino acid modification is useful for immunotherapy.

Another aspect of the invention relates to a method for assessing the usefulness of a disease specific amino acid modification within a peptide or polypeptide expressed in a diseased cell for immunotherapy, the method comprising ascertaining whether the same or different fragments of the peptide or polypeptide comprising the disease specific amino acid modification are presented in the context of different MHC molecules of the same class and/or when presented in the context of different MHC molecules of the same class are reactive with different T cells restricted to the same MHC class.

In one embodiment, the different MHC molecules of the same class are different MHC class I molecules and/or the different T cells restricted to the same MHC class are different CD8+ T cells.

In one embodiment, presentation of the same or different fragments of the peptide or polypeptide comprising the disease specific amino acid modification in the context of different MHC molecules of the same class and/or reactivity of the same or different fragments of the peptide or polypeptide comprising the disease specific amino acid modification when presented in the context of different MHC molecules of the same class with different T cells restricted to the same MHC class indicates that the disease specific amino acid modification is useful for immunotherapy.

Another aspect of the invention relates to a method for assessing the usefulness of a disease specific amino acid modification within a peptide or polypeptide expressed in a diseased cell for immunotherapy, the method comprising ascertaining one or more of the following:
 (i) ascertaining whether the same or different fragments of the peptide or polypeptide comprising the disease specific amino acid modification are presented in the context of MHC molecules of different classes and/or when presented in the context of MHC molecules, preferably MHC molecules of different classes, are reactive with T cells restricted to different MHC classes,
 (ii) ascertaining whether a fragment of the peptide or polypeptide comprising the disease specific amino acid modification when presented in the context of the same MHC molecule is reactive with T cells having different T cell receptors, and/or
 (iii) ascertaining whether the same or different fragments of the peptide or polypeptide comprising the disease specific amino acid modification are presented in the context of different MHC molecules of the same class and/or when presented in the context of different MHC molecules of the same class are reactive with different T cells restricted to the same MHC class.

In one embodiment, the MHC molecules of different classes are MHC class I molecules and MHC class II molecules and/or the T cells restricted to different MHC classes are CD4+ and CD8+ T cells. In one embodiment, presentation of the same or different fragments of the peptide or polypeptide comprising the disease specific amino acid modification in the context of MHC molecules of different classes and/or reactivity of the same or different fragments of the peptide or polypeptide comprising the disease specific amino acid modification when presented in the context of MHC molecules with T cells restricted to different MHC classes indicates that the disease specific amino acid modification is useful for immunotherapy. In one embodiment, the different T cell receptors are of different clonotypes. In one embodiment, reactivity of a fragment of the peptide or polypeptide comprising the disease specific amino acid modification when presented in the context of the same MHC molecule with T cells having different T cell receptors indicates that the disease specific amino acid modification is useful for immunotherapy. In one embodiment, the different MHC molecules of the same class are different MHC class I molecules and/or the different T cells restricted to the same MHC class are different CD8+ T cells. In one embodiment, presentation of the same or different fragments of the peptide or polypeptide comprising the disease specific amino acid modification in the context of different MHC molecules of the same class and/or reactivity of the same or different fragments of the peptide or polypeptide comprising the disease specific amino acid modification when presented in the context of different MHC molecules of the same class with different T cells restricted to the same MHC class indicates that the disease specific amino acid modification is useful for immunotherapy.

Another aspect of the invention relates to a method for selecting and/or ranking disease specific amino acid modifications for their usefulness in immunotherapy, the method comprising the steps of:
 (i) identifying peptides and/or polypeptides expressed in diseased cells each peptide and/or polypeptide comprising at least one disease specific amino acid modification, and
 (ii) ascertaining whether the same or different fragments of a peptide or polypeptide comprising the same disease specific amino acid modification are presented in the context of MHC molecules of different classes and/or when presented in the context of MHC molecules, preferably MHC molecules of different classes, are reactive with T cells restricted to different MHC classes, and
 (iii) repeating step (ii) for at least one further amino acid modification identified under (i).

In one embodiment, the MHC molecules of different classes are MHC class I molecules and MHC class II molecules and/or the T cells restricted to different MHC classes are CD4+ and CD8+ T cells. In one embodiment, presentation of the same or different fragments of the peptide or polypeptide comprising the disease specific amino acid modification in the context of MHC molecules of different classes and/or reactivity of the same or different fragments of the peptide or polypeptide comprising the disease specific amino acid modification when presented in the context of MHC molecules with T cells restricted to different MHC classes indicates that the disease specific amino acid modification is useful for immunotherapy.

Another aspect of the invention relates to a method for selecting and/or ranking disease specific amino acid modifications for their usefulness in immunotherapy, the method comprising the steps of:
 (i) identifying peptides and/or polypeptides expressed in diseased cells each peptide and/or polypeptide comprising at least one disease specific amino acid modification, and
 (ii) ascertaining whether a fragment of a peptide or polypeptide comprising a disease specific amino acid modification when presented in the context of the same MHC molecule is reactive with T cells having different T cell receptors, and
 (iii) repeating step (ii) for at least one further amino acid modification identified under (i).

In one embodiment, the different T cell receptors are of different clonotypes. In one embodiment, reactivity of a fragment of the peptide or polypeptide comprising the disease specific amino acid modification when presented in the context of the same MHC molecule with T cells having different T cell receptors indicates that the disease specific amino acid modification is useful for immunotherapy.

Another aspect of the invention relates to a method for selecting and/or ranking disease specific amino acid modifications for their usefulness in immunotherapy, the method comprising the steps of:
 (i) identifying peptides and/or polypeptides expressed in diseased cells each peptide and/or polypeptide comprising at least one disease specific amino acid modification, and
 (ii) ascertaining whether the same or different fragments of a peptide or polypeptide comprising the same disease specific amino acid modification are presented in the context of different MHC molecules of the same class and/or when presented in the context of different MHC molecules of the same class are reactive with different T cells restricted to the same MHC class, and (iii) repeating step (ii) for at least one further amino acid modification identified under (i).

In one embodiment, the different MHC molecules of the same class are different MHC class I molecules and/or the different T cells restricted to the same MHC class are different CD8+ T cells. In one embodiment, presentation of the same or different fragments of the peptide or polypeptide comprising the disease specific amino acid modification in the context of different MHC molecules of the same class and/or reactivity of the same or different fragments of the peptide or polypeptide comprising the disease specific amino acid modification when presented in the context of different MHC molecules of the same class with different T cells restricted to the same MHC class indicates that the disease specific amino acid modification is useful for immunotherapy.

Another aspect of the invention relates to a method for selecting and/or ranking disease specific amino acid modifications for their usefulness in immunotherapy, the method comprising the steps of:

(i) identifying peptides and/or polypeptides expressed in diseased cells each peptide and/or polypeptide comprising at least one disease specific amino acid modification, and (ii) ascertaining one or more of the following:

(1) ascertaining whether the same or different fragments of a peptide or polypeptide comprising the same disease specific amino acid modification are presented in the context of MHC molecules of different classes and/or when presented in the context of MHC molecules, preferably MHC molecules of different classes, are reactive with T cells restricted to different MHC classes, (2) ascertaining whether a fragment of a peptide or polypeptide comprising a disease specific amino acid modification when presented in the context of the same MHC molecule is reactive with T cells having different T cell receptors, and/or (3) ascertaining whether the same or different fragments of a peptide or polypeptide comprising the same disease specific amino acid modification are presented in the context of different MHC molecules of the same class and/or when presented in the context of different MHC molecules of the same class are reactive with different T cells restricted to the same MHC class, and (iii) repeating step (ii) for at least one further amino acid modification identified under (i).

In one embodiment, the MHC molecules of different classes are MHC class I molecules and MHC class II molecules and/or the T cells restricted to different MHC classes are CD4+ and CD8+ T cells. In one embodiment, presentation of the same or different fragments of the peptide or polypeptide comprising the disease specific amino acid modification in the context of MHC molecules of different classes and/or reactivity of the same or different fragments of the peptide or polypeptide comprising the disease specific amino acid modification when presented in the context of MHC molecules with T cells restricted to different MHC classes indicates that the disease specific amino acid modification is useful for immunotherapy. In one embodiment, the different T cell receptors are of different clonotypes. In one embodiment, reactivity of a fragment of the peptide or polypeptide comprising the disease specific amino acid modification when presented in the context of the same MHC molecule with T cells having different T cell receptors indicates that the disease specific amino acid modification is useful for immunotherapy. In one embodiment, the different MHC molecules of the same class are different MHC class I molecules and/or the different T cells restricted to the same MHC class are different CD8+ T cells. In one embodiment, presentation of the same or different fragments of the peptide or polypeptide comprising the disease specific amino acid modification in the context of different MHC molecules of the same class and/or reactivity of the same or different fragments of the peptide or polypeptide comprising the disease specific amino acid modification when presented in the context of different MHC molecules of the same class with different T cells restricted to the same MHC class indicates that the disease specific amino acid modification is useful for immunotherapy.

In one embodiment, the different amino acid modifications tested in step (ii) are present in the same and/or in different peptides or polypeptides. In one embodiment, the method of the invention comprises comparing the scores obtained for the different amino acid modifications tested in step (ii).

In one embodiment of all aspects of the invention, the disease specific amino acid modification(s) is (are) due to (a) disease specific somatic mutation(s). In one embodiment of all aspects of the invention, the disease is cancer and the immunotherapy is anti-cancer immunotherapy. In one embodiment of all aspects of the invention, the immunotherapy comprises administration of one or more of the following:

(i) a peptide or polypeptide expressed in diseased cells, the peptide or polypeptide comprising at least one disease specific amino acid modification, (ii) a peptide or polypeptide comprising a fragment of the peptide or polypeptide under (i), the fragment comprising at least one disease specific amino acid modification, and (iii) a nucleic acid encoding the peptide or polypeptide under (i) or (ii). In one embodiment of all aspects of the invention, the method of the invention is useful in providing a vaccine.

Another aspect of the invention relates to a method for providing a vaccine comprising the steps: (i) identifying one or more disease specific amino acid modifications which are predicted to be useful for immunotherapy by any of the methods of the invention, (ii) providing a vaccine comprising one or more of the following:

(1) a peptide or polypeptide expressed in diseased cells, the peptide or polypeptide comprising at least one of the disease specific amino acid modifications which are predicted to be useful for immunotherapy, (2) a peptide or polypeptide comprising a fragment of the peptide or polypeptide under (i), the fragment comprising at least one of the disease specific amino acid modifications which are predicted to be useful for immunotherapy, and (3) a nucleic acid encoding the peptide or polypeptide under (i) or (ii).

In one embodiment of all aspects of the invention, the fragment is a MHC binding peptide or a potential MHC binding peptide or can be processed to provide a MHC binding peptide or a potential MHC binding peptide (e.g. MHC binding prediction indicates that the fragment will bind to MHC).

Another aspect of the invention relates to a vaccine produced according to the method of the invention. A vaccine provided according to the invention may comprise a pharmaceutically acceptable carrier and may optionally comprise one or more adjuvants, stabilizers etc. The vaccine may in the form of a therapeutic or prophylactic vaccine.

In one embodiment of all aspects of the invention, indication of a usefulness of a disease specific amino acid modification for immunotherapy indicates that the peptide or polypeptide expressed in a diseased cell comprising the disease specific amino acid modification or a peptide or polypeptide comprising a fragment thereof such as an epitope or vaccine sequence comprising the disease specific amino acid modification upon administration (optionally in the format of the coding nucleic acid) will induce an immune response.

In one embodiment of all aspects of the invention, amino acid modifications in peptides or polypeptides are identified by identifying non-synonymous mutations in one or more coding regions. In one embodiment, amino acid modifications are identified by partially or completely sequencing the genome or transcriptome of one or more cells such as one or more cancer cells and optionally one or more non-cancerous cells and identifying mutations in one or more coding regions. In one embodiment, said mutations are somatic mutations. In one embodiment, said mutations are cancer mutations.

In one embodiment of all aspects of the invention, in particular in order to provide a personalized vaccine for a patient such as a cancer patient, the modification(s) are present in said patient and the methods of the invention are performed for said patient.

Another aspect of the invention relates to a method for inducing an immune response in a patient, comprising administering to the patient a vaccine provided according to the invention.

Another aspect of the invention relates to a method of treating a patient comprising the steps: (a) providing a vaccine using the methods according to the invention; and (b) administering the vaccine to the patient.

Another aspect of the invention relates to a method of treating a patient comprising administering a vaccine as described herein to the patient.

In one embodiment, the patient is a cancer patient and the vaccine is an anti-cancer vaccine such as a vaccine the administration of which provides cancer specific neo-epitopes.

In further aspects, the invention provides a vaccine as described herein for use in the methods of treatment described herein, in particular for use in treating or preventing cancer.

The treatments of cancer described herein can be combined with surgical resection and/or radiation and/or traditional chemotherapy.

The invention also relates to the following:
1. A method for predicting whether a disease-specific amino acid modification within a polypeptide expressed in a diseased cell is useful for immunotherapy, the method comprising determining whether the same or different fragments of the polypeptide comprising the disease-specific amino acid modification are presented in the context of MHC molecules of different classes.
2. The method of item 1, wherein the MHC molecules of different classes are MHC class I molecules and MHC class II molecules.
3. The method of item 1 or 2, wherein presentation of the same or different fragments of the polypeptide comprising the disease-specific amino acid modification in the context of MHC molecules of different classes indicates that the disease-specific amino acid modification is useful for immunotherapy.
4. The method of any one of items 1 to 3 further comprising determining whether the same or different fragments of the polypeptide comprising the disease-specific amino acid modification when presented in the context of MHC molecules are reactive with T cells restricted to different MHC classes.
5. A method for predicting whether a disease-specific amino acid modification within a polypeptide expressed in a diseased cell is useful for immunotherapy, the method comprising determining whether the same or different fragments of the polypeptide comprising the disease-specific amino acid modification when presented in the context of MHC molecules are reactive with T cells restricted to different MHC classes.
6. The method of item 4 or 5, wherein the T cells restricted to different MHC classes are CD4+ and CD8+ T cells.
7. The method of any one of items 4 to 6, wherein T cell reactivity to the same or different fragments of the polypeptide comprising the disease-specific amino acid modification when presented in the context of MHC molecules with T cells restricted to different MHC classes indicates that the disease-specific amino acid modification is useful for immunotherapy.
8. A method for predicting whether a disease-specific amino acid modification within a polypeptide expressed in a diseased cell is useful for immunotherapy, the method comprising determining whether a fragment of the polypeptide comprising the disease-specific amino acid modification when presented in the context of the same MHC molecule is reactive with T cells having different T cell receptors.
9. The method of item 8, wherein the different T cell receptors are of different clonotypes.
10. The method of item 8 or 9, wherein T cell reactivity to a fragment of the polypeptide comprising the disease-specific amino acid modification when presented in the context of the same MHC molecule with T cells having different T cell receptors indicates that the disease-specific amino acid modification is useful for immunotherapy.
11. A method for predicting whether a disease-specific amino acid modification within a polypeptide expressed in a diseased cell is useful for immunotherapy, the method comprising determining whether the same or different fragments of the polypeptide comprising the disease-specific amino acid modification are presented in the context of different MHC molecules of the same class.
12. The method of item 11, wherein the different MHC molecules of the same class are different MHC class I molecules.
13. The method of item 11 or 12, wherein presentation of the same or different fragments of the polypeptide comprising the disease-specific amino acid modification in the context of different MHC molecules of the same class indicates that the disease-specific amino acid modification is useful for immunotherapy.
14. The method of any one of items 11 to 13 further comprising determining whether the same or different fragments of the polypeptide comprising the disease-specific amino acid modification when presented in the context of different MHC molecules of the same class are reactive with different T cells restricted to the same MHC class.
15. A method for predicting whether a disease-specific amino acid modification within a polypeptide expressed in a diseased cell is useful for immunotherapy, the method comprising determining whether the same or different fragments of the polypeptide comprising the disease-specific amino acid modification when presented in the context of different MHC molecules of the same class are reactive with different T cells restricted to the same MHC class.
16. The method of item 14 or 15, wherein the different MHC molecules of the same class are different MHC class I molecules.
17. The method of any one of items 14 to 16, wherein the different T cells restricted to the same MHC class are different CD8+ T cells.
18. The method of any one of items 14 to 17, wherein T cell reactivity to the same or different fragments of the polypeptide comprising the disease-specific amino acid modification when presented in the context of different MHC molecules of the same class with different T cells restricted to the same MHC class indicates that the disease-specific amino acid modification is useful for immunotherapy.
19. A method for predicting whether a disease-specific amino acid modification within a polypeptide expressed in a diseased cell is useful for immunotherapy, the method comprising determining one or more of the following:
(i) determining whether the same or different fragments of the polypeptide comprising the disease-specific amino acid modification are presented in the context of MHC molecules of different classes,
(ii) determining whether the same or different fragments of the polypeptide comprising the disease-specific amino acid modification when presented in the context of MHC molecules are reactive with T cells restricted to different MHC classes,
(iii) determining whether a fragment of the polypeptide comprising the disease-specific amino acid modification when presented in the context of the same MHC molecule is reactive with T cells having different T cell receptors,
(iv) determining whether the same or different fragments of the polypeptide comprising the disease-specific amino acid modification are presented in the context of different MHC molecules of the same class, and
(v) determining whether the same or different fragments of the polypeptide comprising the disease-specific amino acid modification when presented in the context of different MHC molecules of the same class are reactive with different T cells restricted to the same MHC class.
20. The method of item 19 comprising determining whether the same or different fragments of the polypeptide comprising the disease-specific amino acid modification are presented in the context of MHC molecules of different classes and when presented in the context of MHC molecules are reactive with T cells restricted to different MHC classes.
21. The method of item 19 or 20 comprising determining whether the same or different fragments of the polypeptide comprising the disease-specific amino acid modification are presented in the context of different MHC molecules of the same class and when presented in the context of different MHC molecules of the same class are reactive with different T cells restricted to the same MHC class.
22. The method of any one of items 19 to 21, wherein the MHC molecules of different classes are MHC class I molecules and MHC class II molecules.
23. The method of any one of items 19 to 22, wherein the T cells restricted to different MHC classes are CD4+ and CD8+ T cells.
24. The method of any one of items 19 to 23, wherein presentation of the same or different fragments of the polypeptide comprising the disease-specific amino acid modification in the context of MHC molecules of different classes indicates that the disease-specific amino acid modification is useful for immunotherapy.
25. The method of any one of items 19 to 24, wherein T cell reactivity to the same or different fragments of the polypeptide comprising the disease-specific amino acid modification when presented in the context of MHC molecules with T cells restricted to different MHC classes indicates that the disease-specific amino acid modification is useful for immunotherapy.
26. The method of any one of items 19 to 25, wherein the different T cell receptors are of different clonotypes.
27. The method of any one of items 19 to 26, wherein T cell reactivity to a fragment of the polypeptide comprising the disease-specific amino acid modification when presented in the context of the same MHC molecule with T cells having different T cell receptors indicates that the disease-specific amino acid modification is useful for immunotherapy.
28. The method of any one of items 19 to 27, wherein the different MHC molecules of the same class are different MHC class I molecules.
29. The method of any one of items 19 to 28, wherein the different T cells restricted to the same MHC class are different CD8+ T cells.
30. The method of any one of items 19 to 29, wherein presentation of the same or different fragments of the polypeptide comprising the disease-specific amino acid modification in the context of different MHC molecules of the same class indicates that the disease-specific amino acid modification is useful for immunotherapy.
31. The method of any one of items 19 to 30, wherein T cell reactivity to the same or different fragments of the polypeptide comprising the disease-specific amino acid modification when presented in the context of different MHC molecules of the same class with different T cells restricted to the same MHC class indicates that the disease-specific amino acid modification is useful for immunotherapy.
32. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining whether the same or different fragments of a polypeptide comprising the same disease-specific amino acid modification are presented in the context of MHC molecules of different classes, and
(iii) repeating step (ii) for at least one further amino acid modification identified under (i).
33. The method of item 32, wherein the MHC molecules of different classes are MHC class I molecules and MHC class II molecules.

34. The method of item 32 or 33, wherein presentation of the same or different fragments of the polypeptide comprising the disease-specific amino acid modification in the context of MHC molecules of different classes indicates that the disease-specific amino acid modification is useful for immunotherapy.

35. The method of any one of items 32 to 34 wherein step (ii) further comprises determining whether the same or different fragments of the polypeptide comprising the same disease-specific amino acid modification when presented in the context of MHC molecules are reactive with T cells restricted to different MHC classes.

36. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining whether the same or different fragments of a polypeptide comprising the same disease-specific amino acid modification when presented in the context of MHC molecules are reactive with T cells restricted to different MHC classes, and
(iii) repeating step (ii) for at least one further amino acid modification identified under (i).

37. The method of item 35 or 36, wherein the T cells restricted to different MHC classes are CD4+ and CD8+ T cells.

38. The method of any one of items 35 to 37, wherein T cell reactivity to the same or different fragments of the polypeptide comprising the disease-specific amino acid modification when presented in the context of MHC molecules with T cells restricted to different MHC classes indicates that the disease-specific amino acid modification is useful for immunotherapy.

39. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining whether a fragment of a polypeptide comprising a disease-specific amino acid modification when presented in the context of the same MHC molecule is reactive with T cells having different T cell receptors, and
(iii) repeating step (ii) for at least one further amino acid modification identified under (i).

40. The method of item 39, wherein the different T cell receptors are of different clonotypes.

41. The method of item 39 or 40, wherein T cell reactivity to a fragment of the polypeptide comprising the disease-specific amino acid modification when presented in the context of the same MHC molecule with T cells having different T cell receptors indicates that the disease-specific amino acid modification is useful for immunotherapy.

42. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining whether the same or different fragments of a polypeptide comprising the same disease-specific amino acid modification are presented in the context of different MHC molecules of the same class, and
(iii) repeating step (ii) for at least one further amino acid modification identified under (i).

43. The method of item 42, wherein the different MHC molecules of the same class are different MHC class I molecules.

44. The method of item 42 or 43, wherein presentation of the same or different fragments of the polypeptide comprising the disease-specific amino acid modification in the context of different MHC molecules of the same class indicates that the disease-specific amino acid modification is useful for immunotherapy.

45. The method of any one of items 42 to 44 wherein step (ii) further comprises determining whether the same or different fragments of the polypeptide comprising the same disease-specific amino acid modification when presented in the context of different MHC molecules of the same class are reactive with different T cells restricted to the same MHC class.

46. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining whether the same or different fragments of a polypeptide comprising the same disease-specific amino acid modification when presented in the context of different MHC molecules of the same class are reactive with different T cells restricted to the same MHC class, and
(iii) repeating step (ii) for at least one further amino acid modification identified under (i).

47. The method of item 46, wherein the different MHC molecules of the same class are different MHC class I molecules.

48. The method of any one of items 45 to 47, wherein the different T cells restricted to the same MHC class are different CD8+ T cells.

49. The method of any one of items 45 to 48, wherein T cell reactivity to the same or different fragments of the polypeptide comprising the disease-specific amino acid modification when presented in the context of different MHC molecules of the same class with different T cells restricted to the same MHC class indicates that the disease-specific amino acid modification is useful for immunotherapy.

50. A method for selecting and/or ranking disease-specific amino acid modifications for their usefulness in immunotherapy, the method comprising the steps of:
(i) identifying polypeptides expressed in diseased cells each polypeptide comprising at least one disease-specific amino acid modification, and
(ii) determining one or more of the following:
(1) determining whether the same or different fragments of a polypeptide comprising the same disease-specific amino acid modification are presented in the context of MHC molecules of different classes,
(2) determining whether the same or different fragments of a polypeptide comprising the same disease-specific amino acid modification when presented in the context of MHC molecules are reactive with T cells restricted to different MHC classes,
(3) determining whether a fragment of a polypeptide comprising a disease-specific amino acid modification when presented in the context of the same MHC molecule is reactive with T cells having different T cell receptors, (4) determining whether the same or different fragments of a polypeptide comprising the same disease-specific amino acid modification are presented in the context of different MHC molecules of the same class, and
(5) determining whether the same or different fragments of a polypeptide comprising the same disease-specific amino acid modification when presented in the context of different MHC molecules of the same class are reactive with different T cells restricted to the same MHC class, and
(iii) repeating step (ii) for at least one further amino acid modification identified under (i).
51. The method of item 50 wherein step (ii) comprises determining whether the same or different fragments of a polypeptide comprising the same disease-specific amino acid modification are presented in the context of MHC molecules of different classes and when presented in the context of MHC molecules are reactive with T cells restricted to different MHC classes.
52. The method of item 50 or 51 wherein step (ii) comprises determining whether the same or different fragments of a polypeptide comprising the same disease-specific amino acid modification are presented in the context of different MHC molecules of the same class and when presented in the context of different MHC molecules of the same class are reactive with different T cells restricted to the same MHC class.
53. The method of any one of items 50 to 52, wherein the MHC molecules of different classes are MHC class I molecules and MHC class II molecules.
54. The method of any one of items 50 to 53, wherein the T cells restricted to different MHC classes are CD4+ and CD8+ T cells.
55. The method of any one of items 50 to 54, wherein presentation of the same or different fragments of the polypeptide comprising the disease-specific amino acid modification in the context of MHC molecules of different classes indicates that the disease-specific amino acid modification is useful for immunotherapy.
56. The method of any one of items 50 to 55, wherein T cell reactivity to the same or different fragments of the polypeptide comprising the disease-specific amino acid modification when presented in the context of MHC molecules with T cells restricted to different MHC classes indicates that the disease-specific amino acid modification is useful for immunotherapy.
57. The method of any one of items 50 to 56, wherein the different T cell receptors are of different clonotypes.
58. The method of any one of items 50 to 57, wherein T cell reactivity to a fragment of the polypeptide comprising the disease-specific amino acid modification when presented in the context of the same MHC molecule with T cells having different T cell receptors indicates that the disease-specific amino acid modification is useful for immunotherapy.
59. The method of any one of items 50 to 58, wherein the different MHC molecules of the same class are different MHC class I molecules.
60. The method of any one of items 50 to 59, wherein the different T cells restricted to the same MHC class are different CD8+ T cells.
61. The method of any one of items 50 to 60, wherein presentation of the same or different fragments of the polypeptide comprising the disease-specific amino acid modification in the context of different MHC molecules of the same class indicates that the disease-specific amino acid modification is useful for immunotherapy.
62. The method of any one of items 50 to 61, wherein T cell reactivity to the same or different fragments of the polypeptide comprising the disease-specific amino acid modification when presented in the context of different MHC molecules of the same class with different T cells restricted to the same MHC class indicates that the disease-specific amino acid modification is useful for immunotherapy.
63. The method of any one of items 32 to 62, wherein amino acid modifications tested in step (ii) are present in the same polypeptide.
64. The method of any one of items 32 to 63, wherein amino acid modifications tested in step (ii) are present in different polypeptides.
65. The method of any one of items 32 to 64, which comprises comparing the scores obtained for the different amino acid modifications tested in step (ii).
66. The method of any one of items 1 to 65, wherein the disease-specific amino acid modification(s) is (are) due to (a) disease-specific somatic mutation(s).
67. The method of any one of items 1 to 66, wherein the disease is cancer and the immunotherapy is anti-cancer immunotherapy. 68. The method of any one of items 1 to 67, wherein the immunotherapy comprises administration of one or more of the following:
(i) a polypeptide expressed in diseased cells, the polypeptide comprising at least one disease-specific amino acid modification,
(ii) a polypeptide comprising a fragment of the polypeptide under (i), the fragment comprising at least one disease-specific amino acid modification, and
(iii) a nucleic acid encoding the polypeptide under (i) or (ii).
69. The method of any one of items 1 to 68, which is useful in providing a vaccine.
70. A method for providing a vaccine comprising the steps:
(i) identifying one or more disease-specific amino acid modifications which are predicted to be useful for immunotherapy by the method of any one of items 1 to 69,
(ii) providing a vaccine comprising one or more of the following:
(1) a polypeptide expressed in diseased cells, the polypeptide comprising at least one of the disease-specific amino acid modifications which are predicted to be useful for immunotherapy,
(2) a polypeptide comprising a fragment of the polypeptide under (i), the fragment comprising at least one of the disease-specific amino acid modifications which are predicted to be useful for immunotherapy, and
(3) a nucleic acid encoding the polypeptide under (i) or (ii).
71. The method of any one of items 1 to 70, wherein the fragment is a MHC binding peptide or a potential MHC binding peptide or can be processed to provide a MHC binding peptide or a potential MHC binding peptide.
72. A vaccine produced according to the method of any one of items 69 to 71.
73. A method of treating cancer, said method comprising administering an immunogenic composition comprising a polypeptide comprising a disease-specific amino acid modification identified according to the method of any one of items 1 to 68 or a nucleic acid encoding the polypeptide.
74. The method of item 73, wherein said immunogenic composition is a vaccine.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta*, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention The present invention envisions the immunotherapy of diseases, in particular cancer diseases, by utilizing a protein or a protein fragment present in diseased cells as a label for and targeting diseased cells. In particular, the diseased cells may be targeted by targeting a fragment of a protein presented on the surface of the diseased cells in the context of MHC. Specifically, the present invention aims at defining disease specific amino acid modifications in peptides or polypeptides expressed in diseased cells which modifications are located within fragments of the peptides or polypeptides suitable for immunotherapy. Such fragments comprising one or more disease specific amino acid modifications are or comprise neo-epitopes suitable for immunotherapy, in particular for eliciting an efficient cellular immune response against diseased cells expressing peptides or polypeptides comprising the disease specific amino acid modifications and fragments of the peptides or polypeptides. Once a suitable fragment comprising a disease specific amino acid modification has been identified this fragment (optionally as part of a larger polypeptide) or a nucleic acid coding for the fragment (optionally as part of a larger polypeptide) may be used as a vaccine in order to enhance or induce an immune response against cells expressing the modified peptide or polypeptide from which the fragment is derived, in particular by inducing and/or activating appropriate effector cells such as T cells that recognize cells expressing the modified peptide or polypeptide when presented in the context of MHC.

According to the invention, a peptide or polypeptide which comprises one or more disease specific amino acid modifications and which is expressed in diseased cells is also termed "neo-antigen" herein. Furthermore, according to the invention, a fragment of a neo-antigen which comprises one or more disease specific amino acid modifications, is recognized by the immune system, for example, which is recognized by a T cell, in particular when presented in the context of MHC molecules, and which preferably has been determined by the methods of the invention to be useful for immunotherapy (optionally as part of a larger polypeptide, for example as part of the neo-antigen or an artificial peptide or polypeptide, e.g. as part of a multi-epitopic polypeptide comprising, for example, 2 or more of the neo-epitopes which have been determined by the methods of the invention to be useful for immunotherapy) is also termed "neo-epitope" herein.

According to the invention, a disease specific amino acid modification is preferably due to one or more disease specific somatic mutations. In one particularly preferred embodiment, a disease specific amino acid modification is a cancer specific amino acid modification and a disease specific somatic mutation is a cancer specific somatic mutation. Thus, according to the invention, a vaccine preferably features disease specific amino acid modifications/disease specific somatic mutations of a patient and preferably upon administration provides one or more mutation based neo-epitopes. Thus, the vaccine may comprise a peptide or polypeptide comprising one or more mutation based neo-epitopes, or a nucleic acid encoding said peptide or polypeptide. In one embodiment, disease specific amino acid modifications are identified by identifying disease specific somatic mutations, e.g. by sequencing genomic DNA and/or RNA of diseased tissue or one or more diseased cells.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more than 100 amino acid residues, but in general the terms "peptide", "polypeptide" and "protein" are synonyms and are used interchangeably herein.

According to the invention, the term "disease specific amino acid modification" relates to an amino acid modification that is present in the amino acid sequence of a peptide or polypeptide of a diseased cell but absent in the amino acid sequence of a peptide or polypeptide of a corresponding normal, i.e. non-diseased, cell.

According to the invention, the term "tumor specific amino acid modification" or "cancer specific amino acid modification" relates to an amino acid modification that is present in the amino acid sequence of a peptide or polypeptide of a tumor or cancer cell but absent in the amino acid sequence of a peptide or polypeptide of a corresponding normal, i.e. non-tumorous or non-cancerous, cell.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and amino acid substitution variants, preferably amino acid substitution variants. All these sequence changes according to the invention may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

According to the invention, a disease specific amino acid modification or a peptide or polypeptide fragment comprising a disease specific amino acid modification such as an epitope or vaccine sequence may be derived from a peptide or polypeptide comprising the disease specific amino acid modification.

The term "derived" means according to the invention that a particular entity, such as a particular amino acid sequence, is present in the object from which it is derived. In the case of amino acid sequences, especially particular sequence regions, "derived" in particular means that the relevant amino acid sequence is derived from an amino acid sequence in which it is present.

According to the invention, peptides or polypeptides described herein preferably comprise one or more disease specific amino acid modifications. In one embodiment, these one or more disease specific amino acid modifications are located within epitopes or potential epitopes of the peptide or polypeptide. Thus, preferred peptides or polypeptides described herein are neo-antigens preferably comprising one or more neo-epitopes. Similarly, a preferred peptide or polypeptide fragment described herein is a fragment of a peptide or polypeptide comprising one or more disease specific amino acid modifications, wherein one or more disease specific amino acid modifications are located within the fragment. Thus, a preferred peptide or polypeptide fragment described herein is a neo-epitope.

According to the invention, the term "disease specific mutation" relates to a somatic mutation that is present in the nucleic acid of a diseased cell but absent in the nucleic acid of a corresponding normal, i.e. non-diseased, cell.

According to the invention, the term "tumor specific mutation" or "cancer specific mutation" relates to a somatic mutation that is present in the nucleic acid of a tumor or cancer cell but absent in the nucleic acid of a corresponding normal, i.e. non-tumorous or non-cancerous, cell. The terms "tumor specific mutation" and "tumor mutation" and the terms "cancer specific mutation" and "cancer mutation" are used interchangeably herein.

The term "immune response" relates to a reaction of the immune system. The term "immune response" includes the innate immune response and the adaptive immune response. Preferably, the immune response is related to an activation of immune cells and, more preferably, is related to a cellular immune response.

It is preferred that the immune response induced by the compositions described herein comprises the steps of activation of antigen presenting cells, such as dendritic cells and/or macrophages, presentation of an antigen or fragment thereof by said antigen presenting cells and activation of cytotoxic T cells due to this presentation.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill diseased cells such as cancer cells, preventing the production of more diseased cells. In preferred embodiments, the present invention involves the stimulation of an anti-disease CTL response against diseased cells expressing one or more disease-associated antigens and preferably presenting such disease-associated antigens with class I MHC, particularly an anti-tumor CTL response against tumor cells expressing one or more tumor-expressed antigens and preferably presenting such tumor-expressed antigens with class I MHC.

According to the invention, the term "antigen" or "immunogen" covers any substance, preferably a peptide or polypeptide, that is a target of an immune response and/or that will elicit an immune response. In particular, an "antigen" relates to any substance that reacts specifically with antibodies or T-Lymphocytes (T-cells). In one embodiment, the term "antigen" comprises a molecule which comprises at least one epitope such as a T cell epitope. Preferably, an antigen in the context of the present invention is a molecule which, optionally after processing, induces an immune reaction, which is preferably specific for the antigen or cells expressing the antigen. In the context of the embodiments of the present invention, an antigen is preferably presented by a cell, preferably by an antigen presenting cell, in the context of MHC molecules, which results in an immune reaction against the antigen or cells expressing the antigen.

The term "disease-associated antigen" is used in it broadest sense to refer to any antigen associated with a disease. In one embodiment, a disease-associated antigen is a molecule which contains one or more epitopes that will stimulate a host's immune system to make a cellular immune response against diseased cells. The disease-associated antigen may therefore be used for therapeutic purposes. Disease-associated antigens may be associated with cancer, typically tumors.

According to the invention, the term "neo-antigen" relates to a peptide or polypeptide including one or more amino acid modifications compared to the parental peptide or polypeptide. For example, the neo-antigen may be a tumor-associated neo-antigen, wherein the term "tumor-associated neo-antigen" includes a peptide or polypeptide including amino acid modifications due to tumor specific mutations.

The term "epitope" refer to an antigenic determinant in a molecule such as an antigen, i.e., to a part in or fragment of an antigen that is recognized by the immune system, for example, that is recognized by a T cell, in particular when presented in the context of MHC molecules. An epitope of a peptide or polypeptide preferably comprises a continuous or discontinuous portion of said peptide or polypeptide and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope may bind to MHC molecules such as MHC molecules on the surface of a cell and optionally may be recognized by a T cell receptor such as a T cell receptor on the surface of a T cell. Thus, in one embodiment, an epitope is a "MHC binding peptide" and, more preferably, a "T cell epitope".

The term "major histocompatibility complex" and the abbreviation "MHC" include MHC class I and MHC class II molecules and relate to a complex of genes which is present in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and non-self-antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

The MHC is both polygenic (there are several MHC class I and MHC class II genes) and polymorphic (there are multiple alleles of each gene).

As used herein, the term "haplotype" refers to the MHC alleles found on one chromosome and the proteins encoded thereby. Haplotype may also refer to the allele present at any one locus within the MHC. Each class of MHC is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-DQA1, HLA-DQB1, HLA-DPA1, HLA-DPB1, HLA-DMA, HLA-DMB, HLA-DOA, and HLA-DOB for class II. The terms "HLA allele" and "MHC allele" are used interchangeably herein.

The MHCs exhibit extreme polymorphism: within the human population there are, at each genetic locus, a great number of haplotypes comprising distinct alleles. Different polymorphic MHC alleles, of both class I and class II, have different peptide specificities: each allele encodes proteins that bind peptides exhibiting particular sequence patterns.

In one preferred embodiment of all aspects of the invention an MHC molecule is an HLA molecule.

As used herein, a peptide or epitope is said to "be presented in the context of an MHC molecule" if the peptide or epitope binds to the MHC molecule. Such binding may be detected using any assay known in the art. The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective. In one preferred embodiment of all aspects of the invention an MHC molecule is an HLA molecule.

If a peptide or epitope is part of a larger entity comprising additional sequences, e.g. of a vaccine sequence or polypeptide, and is to be presented following processing, in particular following cleavage, the peptide or epitope produced by processing has a length which is suitable for binding to an MHC molecule. Preferably, the sequence of the peptide or epitope which is to be presented following processing is derived from the amino acid sequence of an antigen or polypeptide used for vaccination, i.e., its sequence substantially corresponds and is preferably completely identical to a fragment of the antigen or polypeptide.

Thus, an MHC binding peptide in one embodiment comprises a sequence which substantially corresponds and is preferably completely identical to a fragment of an antigen.

As used herein the term "neo-epitope" includes an epitope that is not present in a reference such as a normal non-diseased (e.g. non-cancerous) or germline cell but is found in diseased cells (e.g. cancer cells). This includes, in particular, situations wherein in a normal non-diseased or germline cell a corresponding epitope is found, however, due to one or more mutations in a diseased cell the sequence of the epitope is changed so as to result in the neo-epitope.

As used herein, the term "T cell epitope" refers to a peptide which binds to a MHC molecule in a configuration recognized by a T cell receptor. Typically, T cell epitopes are presented on the surface of an antigen-presenting cell. A T cell epitope according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, a T cell epitope is capable of stimulating a cellular response against a cell characterized by presentation of an antigen with class I MHC and preferably is capable of stimulating an antigen-responsive cytotoxic T-lymphocyte (CTL).

In one embodiment, a vaccine according to the present invention provides one or more neo-epitopes suitable for vaccination of a target organism. A person skilled in the art will know that one of the principles of immunobiology and vaccination is based on the fact that an immunoprotective reaction to a disease is produced by immunizing an organism with a vaccine, which is immunologically relevant with respect to the disease to be treated. According to the present invention, an antigen is preferably a self-antigen.

The term "immunogenicity" relates to the relative effectivity to induce an immune response that is preferably associated with therapeutic treatments, such as treatments against cancers. As used herein, the term "immunogenic" relates to the property of having immunogenicity. For example, the term "immunogenic modification" when used in the context of a peptide, polypeptide or protein relates to the effectivity of said peptide, polypeptide or protein to induce an immune response that is caused by and/or directed against said modification. Preferably, the non-modified peptide, polypeptide or protein does not induce an immune response, induces a different immune response or induces a different level, preferably a lower level, of immune response.

According to the invention, the term "immunogenicity" or "immunogenic" preferably relates to the relative effectivity to induce a biologically relevant immune response, in particular an immune response which is useful for vaccination. Thus, in one preferred embodiment, an amino acid modification or modified peptide is immunogenic if it induces an immune response against the target modification in a subject, which immune response may be beneficial for therapeutic or prophylactic purposes.

As used herein, the term "assessing the usefulness of a disease specific amino acid modification for immunotherapy" or "predicting whether a disease-specific amino acid modification is useful for immunotherapy" refers to a prediction whether the disease specific amino acid modification, in particular the antigen which comprises the disease specific amino acid modification or a fragment of the antigen comprising the disease specific amino acid modification such as a fragment of the antigen comprising one or more epitopes comprising the disease specific amino acid modification, in particular one or more T cell epitopes, will be useful for inducing an immune response or targeting an immune response. The term "disease specific amino acid modification which is predicted to be useful for immunotherapy" or similar terms refers to the fact that a disease specific amino acid modification, in particular the antigen which comprises the disease specific amino acid modification or a fragment of the antigen comprising the disease specific amino acid modification such as a fragment of the antigen comprising one or more epitopes comprising the disease specific amino acid modification, in particular one or more T cell epitopes, has been predicted to be useful for inducing an immune response or targeting an immune response. If a disease specific amino acid modification is predicted to be useful for immunotherapy, for example, the antigen which comprises the disease specific amino acid modification or a fragment of the antigen comprising the disease specific amino acid modification such as a fragment of the antigen comprising one or more epitopes comprising the disease specific amino acid modification, in particular one or more T cell epitopes, may be used for vaccination or designing a vaccine as described herein.

According to the invention, an epitope such as a T cell epitope may be present in a vaccine as a part of a larger entity such as a vaccine sequence and/or a polypeptide comprising more than one epitope. The presented peptide or epitope is produced following suitable processing. Also, epitopes may be modified at one or more residues that are not essential for binding to MHC or for TCR recognition. Such modified epitopes may be considered immunologically equivalent. Preferably an epitope when presented by MHC and recognized by a T cell receptor is able to induce in the presence of appropriate co-stimulatory signals, clonal expansion of the T cell carrying the T cell receptor specifically recognizing the peptide/MHC-complex. Preferably, an epitope comprises an amino acid sequence substantially corresponding to the amino acid sequence of a fragment of an antigen. Preferably, said fragment of an antigen is an MHC class I and/or class II presented peptide.

"Antigen processing" or "processing" refers to the degradation of a peptide, polypeptide or protein into procession products, which are fragments of said peptide, polypeptide or protein (e.g., the degradation of a polypeptide into peptides) and the association of one or more of these fragments (e.g., via binding) with MHC molecules for presentation by cells, preferably antigen presenting cells, to specific T cells.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcy receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

By "cell characterized by presentation of an antigen" or "cell presenting an antigen" or similar expressions is meant a cell such as a diseased cell, e.g. a cancer cell, or an antigen presenting cell presenting an antigen or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

"Target cell" shall mean a cell which is a target for an immune response such as a cellular immune response. Target cells include cells that present an antigen, i.e. a peptide fragment derived from an antigen, and include any undesirable cell such as a cancer cell. In preferred embodiments, the target cell is a cell expressing an antigen as described herein and preferably presenting said antigen with class I MHC.

The term "portion" refers to a fraction. With respect to a particular structure such as an amino acid sequence or protein the term "portion" thereof may designate a continuous or discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "effector cell", "immune effector cell" or "immunoreactive cell" in the context of the present invention relates to a cell which exerts effector functions during an immune reaction. An "immunoreactive cell" preferably is capable of binding an antigen or a cell characterized by presentation of an antigen or a peptide fragment thereof (e.g. a T cell epitope) and mediating an immune response. For example, such cells secrete cytokines and/or chemokines, secrete antibodies, recognize cancerous cells, and optionally eliminate cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, immunoreactive cells are T cells, preferably CD4$^+$ and/or CD8$^+$ T cells.

Preferably, an "immunoreactive cell" recognizes an antigen or a peptide fragment thereof with some degree of specificity, in particular if presented in the context of MHC molecules such as on the surface of antigen presenting cells or diseased cells such as cancer cells. Preferably, said recognition enables the cell that recognizes an antigen or a peptide fragment thereof to be responsive or reactive. If the cell is a helper T cell (CD4 T cell) bearing receptors that recognize an antigen or a peptide fragment thereof in the context of MHC class II molecules such responsiveness or reactivity may involve the release of cytokines and/or the activation of CD8$^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an antigen fragment and are responsive or reactive are also termed "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The first signal in activation of T cells is provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naïve responses, although B cells and macrophages can be important APCs.

According to the present invention, a molecule is capable of binding to a target if it has a significant affinity for said predetermined target and binds to said predetermined target in standard assays. "Affinity" or "binding affinity" is often measured by equilibrium dissociation constant ($K_D$). A molecule is not (substantially) capable of binding to a target if it has no significant affinity for said target and does not bind significantly to said target in standard assays.

Cytotoxic T lymphocytes may be generated in vivo by incorporation of an antigen or a peptide fragment thereof into antigen-presenting cells in viva. The antigen or a peptide fragment thereof may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Malay et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines such as IFNγ), or cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity. In particular, intracellular cytokine staining or ELISPOT can be used for detection of cytokines produced by both CD4+ and CD8+ T-cells, for example, by using methods as described herein.

Generally, in an ELISPOT assay, the surfaces of a membrane are coated with capture antibody that binds a specific epitope of the cytokine being assayed. As cells are activated, they release the cytokine, which is captured directly on the membrane surface by the immobilized antibody. The cytokine is thus "captured" in the area directly surrounding the secreting cell. Subsequent detection steps visualize the immobilized cytokine as an "immunospot", which is essentially the secretory footprint of the activated cell. The ELISPOT assay technique thus allows estimating the number and/or frequency of T cells that are producing a given cytokine (for example, IFNγ) in response to a specific antigenic stimulus. Spot counts may be expressed as median values obtained from replicates and may be compared to negative controls (e.g. unstimulated cells). A response may be defined as positive if a minimum number of spots per a certain number of cells is observed and/or the number of spots exceeds a certain level compared to the negative control. For example, a response may be defined as positive if there is a minimum of five spots per $1\times10^3$ cells, $1\times10^4$ cells, or $1\times10^5$ cells and/or if the spot count is more than 2×, 3×, 4×, 5× as high, or even higher, as the respective negative control.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or polypeptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4+ T cell) the recognition of an antigen or an antigen fragment in the context of MHC class II molecules by T cell receptors, the release of cytokines and/or the activation of CD8+ lymphocytes (CTLs) and/or B-cells, and in the case of CTL the recognition of an antigen or an antigen fragment in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

In general, according to the invention, disease specific amino acid modifications and fragments of peptides or polypeptides expressed in diseased cells which fragments comprise one or more disease specific amino acid modifications are assessed with respect to their usefulness in immunotherapy. One or more fragments with predicted usefulness for immunotherapy may be used for providing a vaccine comprising, for example, the peptide or polypeptide from which the one or more fragments are derived or one or more peptide fragments of the peptide or polypeptide, in particular one or more (potential) MHC binding peptides of the peptide or polypeptide. The vaccine may also comprise nucleic acid such as RNA encoding the peptide or polypeptide from which the one or more fragments are derived or one or more peptide fragments of the peptide or polypeptide, in particular one or more (potential) MHC binding peptides of the peptide or polypeptide.

According to the invention, the term "score" relates to a result, usually expressed numerically, of a test or assay including, e.g., assays to measure presentation of polypeptide fragments on MHC molecules or assays to measure T cell reactivity to polypeptide fragments on MHC molecules.

Terms such as "a better score" or "score better" relate to a better result or the best result of a test or an assay.

The levels of polypeptide presentation and T cell reactivity can be determined using any methods known in the art. Peptide presentation can be determined, for example, using well known prediction methods as well as experimental methods. For example, a number of biochemical assays have been developed in order to determine the MHC-peptide affinity. A classic method is a competition assay where a usually radioactively labeled reference peptide is bound to the MHC. T cell reactivity assays may also be used to determine MHC peptide binding. T cell reactivity can be assessed as described herein, for example by means of immunologic assays, including enzyme-linked immunosorbent assays (ELISPOT) or cytokine secretion assays (CSA).

According to the invention, disease specific amino acid modifications may be scored according to the predicted ability of peptide or polypeptide epitopes comprising at least one disease specific amino acid modification to (1) be presented in the context of MHC molecules of different classes and/or react with T cells restricted to different MHC classes, (2) react with T cells having different T cell receptors when presented in the context of the same MHC molecule, and/or (3) be presented in the context of different MHC molecules of the same class and/or react with different T cells restricted to the same MHC class when presented in the context of different MHC molecules of the same class.

In general, the more parameters (1) to (3) a disease specific amino acid modification or a peptide or polypeptide epitope comprising at least one disease specific amino acid modification fulfils the better the disease specific amino acid modification is scored.

Terms such as "predict", "predicting" or "prediction" relate to the determination of a likelihood, e.g., that a disease-specific amino acid modification within a polypeptide expressed in a diseased cell is useful for immunotherapy. A disease-specific amino acid modification within a polypeptide expressed in a diseased cell is identified as useful for immunotherapy if the same or different fragments of the polypeptide (these fragments comprise the disease specific amino acid modification) are presented in the context of MHC molecules of different classes, if the same or different fragments of the polypeptide are reactive with T cells restricted to different MHC classes, or both. Alternatively or additionally, a disease-specific amino acid modification within a polypeptide expressed in a diseased cell is identified as useful for immunotherapy if a fragment of the polypeptide comprising the disease specific amino acid modification when presented in the context of the same MHC molecule is reactive with T cells having different T cell receptors. Alternatively or additionally, a disease-specific amino acid modification within a polypeptide expressed in a diseased cell is identified as useful for immunotherapy if the same or different fragments of the polypeptide (these fragments comprise the disease specific amino acid modification) are presented in the context of different MHC molecules of the same class, if the same or different fragments of the polypeptide when presented in the context of different MHC molecules of the same class are reactive with different T cells restricted to the same MHC class, or both.

Presentation of a fragment of a peptide or polypeptide comprising a disease specific amino acid modification in the context of MHC molecules may be ascertained, for example, by using any peptide:MHC binding predictive tools and/or by determining binding of the fragment to MHC molecules experimentally.

Reactivity of a fragment of a peptide or polypeptide comprising a disease specific amino acid modification with T cells when presented in the context of MHC molecules may be ascertained experimentally, for example.

In one embodiment, an assessment is usually made against MHC molecules and/or T cells found in a patient having a disease specific amino acid modification. Accordingly, the present invention may also include determining the MHC and/or T cell repertoire of a patient.

The term "different fragments of the peptide or polypeptide comprising the disease specific amino acid modification" in one embodiment relates to peptides comprising or consisting of different fragments of a modified peptide or polypeptide, said different fragments comprising the same modification(s) present in the peptide or polypeptide but differing in length and/or position of the modification(s). If a peptide or polypeptide has a modification at position x, two or more fragments of said peptide or polypeptide each comprising a different sequence window of said peptide or polypeptide covering said position x are considered different fragments of the peptide or polypeptide comprising the disease specific amino acid modification.

The term "different amino acid modifications" relates to different amino acid modifications of either of the same and/or different peptides or polypeptides.

Preferably, according to the present invention, a "fragment of a peptide or polypeptide comprising a disease specific amino acid modification" has an appropriate length for MHC binding.

The amino acid modifications the usefulness for immunotherapy of which is to be assessed according to the present invention or which are to be selected and/or ranked for their usefulness in immunotherapy according to the invention preferably result from mutations in the nucleic acid of a cell such as a diseased cell, in particular a cancer or tumor cell of a patient. Such mutations may be identified by known sequencing techniques. Accordingly, the methods of the invention may be performed for a patient such as a cancer patient to provide a patient specific vaccine such as an anti-cancer vaccine.

In one embodiment, the mutations are cancer specific somatic mutations in a tumor specimen of a cancer patient which may be determined by identifying sequence differences between the genome, exome and/or transcriptome of a tumor specimen and the genome, exome and/or transcriptome of a non-tumorigenous specimen.

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood. In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

The invention may involve the determination of the cancer mutation signature of a patient. The term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient. Generally, the methods of the invention provides for the identification of a number of mutations which provides a sufficient number of modifications or modified peptides or polypeptides to be included in the methods of the invention.

Preferably, the mutations identified according to the present invention are non-synonymous mutations, preferably non-synonymous mutations of peptides or polypeptides expressed in a tumor or cancer cell.

In one embodiment, cancer specific somatic mutations or sequence differences are determined in the genome, preferably the entire genome, of a tumor specimen. Thus, the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. Thus, the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. Thus, the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual.

In one embodiment, normal genomic germline DNA is obtained from peripheral blood mononuclear cells (PBMCs)

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., *PLoS Gen.*, 4(8): 1-15, 2008).

The term "transcriptome" relates to the set of all RNA molecules, including mRNA, rRNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" refers to isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

Any suitable sequencing method can be used according to the invention for determining mutations, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: *The impact of next-generation sequencing on genomics. J. Genet Genomics* 38 (3), 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Connecticut), first described in Ronaghi et al. 1998: *A sequencing method based on real-time pyrophosphate"*. Science 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, California) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, California). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 platform of Dover Systems (Salem, New Hampshire) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, California) or in the HeliScope™ platform of Helicos Biosciences (Cambridge, Massachusetts). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Texas). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, Rhode Island), and the proprietary ligase-based DNA sequencing platform with DNA nanoball (DNB) technology called combinatorial probe-anchor ligation (cPAL™).

6) Electron microscopy based technologies for single-molecule sequencing, e.g. those developed by Light-Speed Genomics (Sunnyvale, California) and Halcyon Molecular (Redwood City, California)

7) Ion semiconductor sequencing which is based on the detection of hydrogen ions that are released during the polymerisation of DNA. For example, Ion Torrent Systems (San Francisco, California) uses a high-density array of micro-machined wells to perform this biochemical process in a massively parallel way. Each well holds a different DNA template. Beneath the wells is an ion-sensitive layer and beneath that a proprietary Ion sensor.

Preferably, DNA and RNA preparations serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients. Normal non-mutated genomic DNA or RNA can be extracted from normal, somatic tissue, however germline cells are preferred in the context of the present invention. Germline DNA or RNA may be extracted from peripheral blood mononuclear cells (PBMCs) in patients with non-hematological malignancies. Although nucleic acids extracted from FFPE tissues or freshly isolated single cells are highly fragmented, they are suitable for NGS applications.

Several targeted NGS methods for exome sequencing are described in the literature (for review see e.g. Teer and Mullikin 2010: *Human Mol Genet* 19 (2), R145-51), all of which can be used in conjunction with the present invention. Many of these methods (described e.g. as genome capture, genome partitioning, genome enrichment etc.) use hybridization techniques and include array-based (e.g. Hodges et al. 2007: *Nat. Genet.* 39, 1522-1527) and liquid-based (e.g. Choi et al. 2009: *Proc. Natl. Acad. Sci USA* 106, 19096-19101) hybridization approaches. Commercial kits for DNA sample preparation and subsequent exome capture are also available: for example, Illumina Inc. (San Diego, California) offers the TruSee DNA Sample Preparation Kit and the Exome Enrichment Kit TruSeq™ Exome Enrichment Kit.

In order to reduce the number of false positive findings in detecting cancer specific somatic mutations or sequence differences when comparing e.g. the sequence of a tumor sample to the sequence of a reference sample such as the sequence of a germ line sample it is preferred to determine the sequence in replicates of one or both of these sample types. Thus, it is preferred that the sequence of a reference sample such as the sequence of a germ line sample is determined twice, three times or more. Alternatively or additionally, the sequence of a tumor sample is determined twice, three times or more. It may also be possible to determine the sequence of a reference sample such as the sequence of a germ line sample and/or the sequence of a tumor sample more than once by determining at least once the sequence in genomic DNA and determining at least once the sequence in RNA of said reference sample and/or of said tumor sample. For example, by determining the variations between replicates of a reference sample such as a germ line sample the expected rate of false positive (FDR) somatic mutations as a statistical quantity can be estimated. Technical repeats of a sample should generate identical results and any detected mutation in this "same vs. same comparison" is a false positive. In particular, to determine the false discovery rate for somatic mutation detection in a tumor sample relative to a reference sample, a technical repeat of the reference sample can be used as a reference to estimate the number of false positives. Furthermore, various quality related metrics (e.g. coverage or SNP quality) may be combined into a single quality score using a machine learning approach. For a given somatic variation all other variations with an exceeding quality score may be counted, which enables a ranking of all variations in a dataset.

In the context of the present invention, the term "RNA" relates to a molecule which comprises at least one ribonucleotide residue and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, a 3'-UTR and optionally a poly(A) tail. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

in one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides, polypeptides or proteins, e.g. by transcription and/or translation. With respect to RNA, the term "expression" or "translation" relates in particular to the production of peptides, polypeptides or proteins. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into peptide, polypeptide or protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide, polypeptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional peptide, polypeptide or protein, with functional linkage of a regulatory sequence with the coding sequence, induction of the regulatory sequence leads to a transcription of the coding sequence, without causing a reading frame shift in the coding sequence or inability of the coding sequence to be translated into the desired peptide, polypeptide or protein.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Preferably, according to the invention, RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

The present invention provides methods for identifying amino acid modifications predicted as being useful in immunotherapy. The amino acid modifications are present in peptides or polypeptides expressed in diseased cells of a patient. The term "peptide or polypeptide expressed in diseased cells of a patient" does not necessarily mean that expression of the peptide or polypeptide has been tested experimentally. Rather, it is to mean that an open reading frame encoding the peptide or polypeptide is present within diseased cells of a patient and thus, there is a potential for the peptide or polypeptide of being expressed in diseased cells of a patient.

An amino acid modifications predicted as being useful in immunotherapy may be used for designing a vaccine. Specifically, the vaccine may comprise a peptide or polypeptide expressed by a diseased cell and comprising an amino acid modifications predicted as being useful in immunotherapy by the method of the present invention, or a nucleic acid such as RNA encoding said peptide or polypeptide. Alternatively or additionally, the vaccine may comprise a vaccine peptide or polypeptide comprising a fragment of said peptide or polypeptide expressed by a diseased cell, said fragment comprising an amino acid modification predicted as being useful in immunotherapy by the method of the present invention, or a nucleic acid such as RNA encoding said vaccine peptide or polypeptide.

If the methods of the invention indicate that a fragment of a peptide or polypeptide comprising a disease specific amino acid modification (1) is presented in the context of MHC molecules of different classes and/or when presented in the context of MHC molecules is reactive with T cells restricted to different MHC classes, (2) when presented in the context of the same MHC molecule is reactive with T cells having different T cell receptors and/or (3) is presented in the context of different MHC molecules of the same class and/or when presented in the context of different MHC molecules of the same class is reactive with different T cells restricted to the same MHC class, the vaccine peptide or polypeptide preferably comprises at least the sequence of the peptide or polypeptide covering said fragment or a longer sequence, i.e. a vaccine sequence.

If the methods of the invention indicate that different fragments of a peptide or polypeptide comprising a disease specific amino acid modification (1) are presented in the context of MHC molecules of different classes and/or when presented in the context of MHC molecules are reactive with T cells restricted to different MHC classes, and/or (2) are presented in the context of different MHC molecules of the same class and/or when presented in the context of different MHC molecules of the same class are reactive with different T cells restricted to the same MHC class, the vaccine peptide or polypeptide preferably comprises at least the sequence of the peptide or polypeptide covering said fragments or a longer sequence, i.e. a vaccine sequence.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "personalized cancer vaccine" or "individualized cancer vaccine" concerns a particular cancer patient and means that a cancer vaccine is adapted to the needs or special circumstances of an individual cancer patient.

In one embodiment, a vaccine provided according to the invention may comprise a peptide or polypeptide comprising one or more amino acid modifications or one or more modified peptides predicted as being useful in immunotherapy by the methods of the invention or a nucleic acid, preferably RNA, encoding said peptide or polypeptide.

The cancer vaccines provided according to the invention when administered to a patent preferably provide one or more T cell epitopes suitable for stimulating, priming and/or expanding T cells specific for diseased cells of the patient such as the patient's tumor. The T cells are preferably directed against cells expressing antigens from which the T cell epitopes are derived. The vaccines described herein are preferably capable of inducing or promoting a cellular response, preferably cytotoxic T cell activity, against a cancer disease characterized by presentation of one or more tumor-associated neo-antigens with class I MHC. A vaccine targeting cancer specific mutations will be specific for the patient's tumor.

A vaccine provided according to the invention relates to a vaccine which when administered to a patent preferably provides one or more T cell epitopes, such as 2 or more, 5 or more, 10 or more, 15 or more, 20 or more, 25 or more, 30 or more and preferably up to 60, up to 55, up to 50, up to 45, up to 40, up to 35 or up to 30 T cell epitopes, incorporating amino acid modifications or modified peptides predicted as being immunogenic by the methods of the invention. Such T cell epitopes are also termed "neo-epitopes" herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the T cell epitopes are derived and presenting the same epitopes on the surface of the tumor cells.

The methods of the invention may comprise the further step of determining the usability of the identified amino acid modifications or modified peptides for cancer vaccination. Thus further steps can involve one or more of the following: (i) assessing whether the modifications are located in known or predicted MHC presented epitopes, (ii) in vitro and/or in silico testing whether the modifications are located in MHC presented epitopes, e.g. testing whether the modifications are part of peptide sequences which are processed into and/or presented as MHC presented epitopes, and (iii) in vitro testing whether the envisaged modified epitopes, in particular when present in their natural sequence context, e.g. when flanked by amino acid sequences also flanking said epitopes in the naturally occurring peptide or polypeptide, and when expressed in antigen presenting cells are able to stimulate T cells such as T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

Modified peptides determined according to the invention may be ranked for their usability as epitopes for cancer vaccination. Thus, in one aspect, the invention comprises a manual or computer-based analytical process in which the identified modified peptides are analyzed and selected for their usability in the respective vaccine to be provided. In a preferred embodiment, said analytical process is a computational algorithm-based process. Preferably, said analytical process comprises determining and/or ranking epitopes according to a prediction of their capacity of being immunogenic.

The neo-epitopes identified according to the invention and provided by a vaccine of the invention are preferably present in the form of a polypeptide comprising said neo-epitopes such as a polyepitopic polypeptide or a nucleic acid, in particular RNA, encoding said polypeptide. Furthermore, the neo-epitopes may be present in the polypeptide in the form of a vaccine sequence, i.e. present in their natural sequence context, e.g. flanked by amino acid sequences also flanking said epitopes in the naturally occurring peptide or polypeptide. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the neo-epitopes and/or vaccine sequences are lined up in the polypeptide head-to-tail.

In one embodiment, the neo-epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous neo-epitopes like those generated from the junction suture between adjacent neo-epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang et al. (*J. Biol. Chem.*, 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 151(7), 3569-75, 1993). Schlessinger et al. (*Proteins*, 61(1), 115-26, 2005) had found that amino acids glycine and serine included in an amino acid sequence result in a more flexible protein that is more efficiently translated and processed by the proteasome, enabling better access to the encoded neo-epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d(GSG)_e$ wherein a, b, c, d and e is independently a number selected from 0, 1, 2, 3, 4, 5, 6, 7, 8, 9, 10, 11, 12, 13, 14, 15, 16, 17, 18, 19, or 20 and wherein a+b+c+d+e are different from 0 and preferably are 2 or more, 3 or more, 4 or more or 5 or more. In one embodiment, the linker comprises a sequence as described herein including the linker sequences described in the examples such as the sequence GGSGGGGSG.

In one particularly preferred embodiment, a polypeptide incorporating one or more neo-epitopes such as a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the neo-epitopes provided by the different multiepitopic polypeptides may be different or partially overlapping. Once present in cells of a patient such as antigen presenting cells the polypeptide according to the invention is processed to produce the neo-epitopes identified according to the invention. Administration of a vaccine provided according to the invention preferably provides MHC class I-presented epitopes that are capable of eliciting a CD8+ T cell response against cells expressing antigens from which the MHC presented epitopes are derived. Administration of a vaccine provided according to the invention may also provide MHC class II-presented epitopes that are capable of eliciting a CD4+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations but being expressed by cancer cells and preferably inducing an immune response against cancer cells, preferably a cancer specific immune response.

The vaccine provided according to the invention may be a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as neo-epitopes or vaccine sequences derived from different proteins or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The agents and compositions described herein can be used to treat a subject with a disease, e.g., a disease characterized by the presence of diseased cells expressing an antigen and presenting a fragment thereof. Particularly preferred diseases are cancer diseases. Agents and compositions described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "normal" refers to the healthy state or the conditions in a healthy subject or tissue, i.e., non-pathological conditions, wherein "healthy" preferably means non-cancerous.

The term "disease associated with an antigen" or "disease involving an antigen" refers to any disease which implicates an antigen, e.g. a disease which is characterized by the presence of an antigen or cells expressing an antigen. The disease involving an antigen can be a cancer disease or simply cancer. As mentioned above, the antigen may be a disease-associated antigen, such as a tumor-associated antigen.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

For purposes of the present invention, the terms "cancer" and "cancer disease" are used interchangeably with the terms "tumor" and "tumor disease".

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately I CTC/mL and a purity of 0.1% (Allard et al., 2004: Clin Cancer Res 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: Nature 450, 1235-1239). Another possibility for isolating CTCs is using the CellSearch™ Circulating Tumor Cell (CTC) Test from Veridex, LLC (Raritan, NJ) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "immunotherapy" relates to the treatment of a disease or condition by inducing, enhancing, or suppressing an immune response. Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination, or tumor immunization or tumor vaccination. The term "immunotherapy" also relates to the manipulation of immune responses such that inappropriate immune responses are modulated into more appropriate ones in the context of autoimmune diseases such as rheumatic arthritis, allergies, diabetes or multiple sclerosis.

The terms "immunization" or "vaccination" describe the process of administering an antigen to an individual with the purpose of inducing an immune response, for example, for therapeutic or prophylactic reasons.

The term "therapeutic treatment" or simply "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The term "prophylactic treatment" or "preventive treatment" relates to any treatment that is intended to prevent a disease from occurring in an individual. The terms "prophylactic treatment" or "preventive treatment" are used herein interchangeably.

The terms "protect", "prevent", "prophylactic", "preventive", or "protective" relate to the prevention and/or treatment of the occurrence and/or the propagation of a disease, e.g. tumor, in an individual. For example, a prophylactic administration of an immunotherapy, e.g. by administering a composition described herein, can protect the receiving individual from the development of a tumor. For example, a therapeutic administration of an immunotherapy, e.g. by administering a composition described herein, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans. Preferably, the term "patient" relates to a diseased individual.

The agents described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating, preventing, or reducing the severity of a disease or disorder by administration of said pharmaceutical composition to an individual. A pharmaceutical composition is also known in the art as a pharmaceutical formulation. The pharmaceutical composition can be administered locally or systemically.

The term "systemic administration" refers to the administration of a therapeutically effective agent such that the agent becomes widely distributed in the body of an individual in significant amounts and develops a biological effect. According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

In one particularly preferred embodiment, the composition according to the present invention is administered to muscle tissue, such as skeletal muscle. Intramuscular administration such as by intramuscular injection thus is the preferred route of administration.

Administration can be achieved in various ways. In one embodiment, the composition according to the present invention is administered by injection. In a preferred embodiment, injection is via a needle. Needle-free injection may be used as an alternative.

The pharmaceutical compositions of the present invention may comprise at least one adjuvant. The term "adjuvant" relates to compounds, which when administered in combination with an antigen or antigen peptide to an individual, prolong or enhance or accelerate an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The agents and compositions provided herein may be used alone or in combination with other therapeutic regimens such as surgery, irradiation, chemotherapy and/or bone marrow transplantation (autologous, syngeneic, allogeneic or unrelated).

The present invention is described in detail and is illustrated by the figures and examples, which are used only for illustration purposes and are not meant to be limiting. Owing to the description and the examples, further embodiments which are likewise included in the invention are accessible to the skilled worker.

FIGURES

FIG. 1. Exemplary cases for induction of a pure CD4+ or a dual CD4+/CD8+ T-cell response against a neo-epitope. a, Pre- and post-vaccination CD4+ and CD8+ T cell-enriched cultures of patient P19 stimulated with the patient's pentatope RNAs were read-out against autologous DCs loaded with OLPs covering a mutated neo-epitope in the ST5 (suppressor of tumorigenicity 5) protein. b-c, Pre- and post-vaccination CD4+ and CD8+ T cell enriched cultures of patient P19 stimulated with the patient-specific pentatope RNA were read-out in IFNγ-ELISpot against autologous DCs loaded with OLPs covering a mutated neo-epitope in the UTP6 (small subunit processome component) protein. c, CD4+ and CD8+ T cell cultures were quality controlled after stimulation for purity by flow cytometry.

Figure 2:
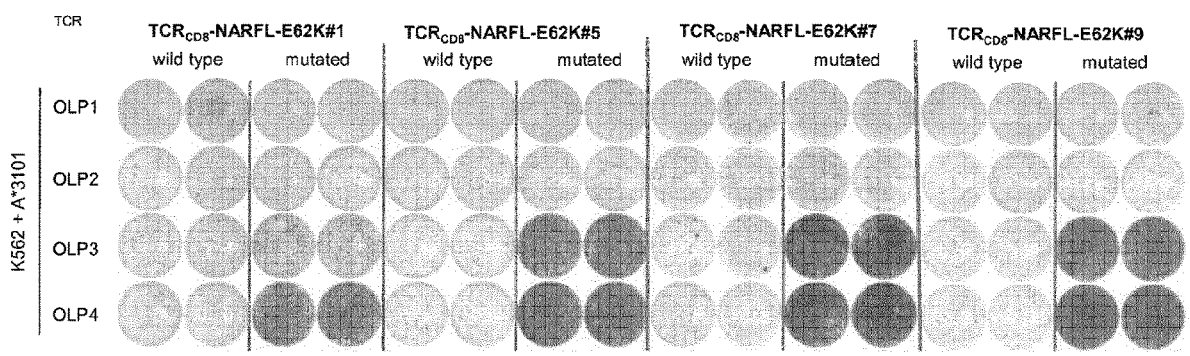

FIG. 2. Specificity of NARFL-E62K-specific TCRs cloned from CD8+ T cells of patient P01. CD8+ T cells transfected with TCRs #1, #5, #7 or #9-directed against a mutation in the NARFL (Nuclear Prelamin A Recognition Factor Like) protein were tested by IFNg-ELISpot for recognition of K562 cells transfected with HLA-A*3101 and pulsed with individual 15mer peptides covering either the mutated or the wild-type sequence.

Figure 3:
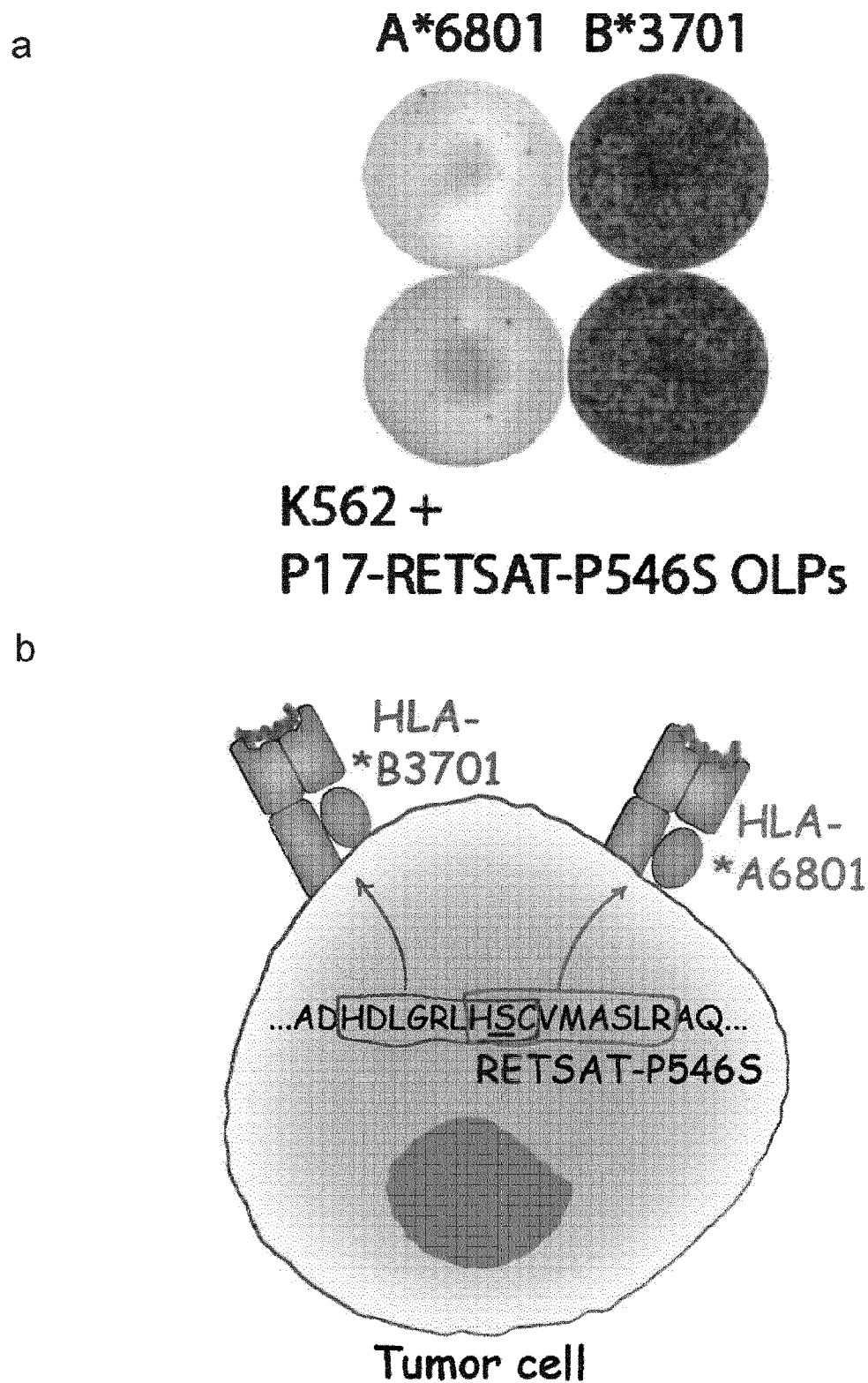

FIG. 3. Disease control in melanoma patients with high risk for relapse under neo-epitope RNA vaccination, a, RNAs encoding TCR-α/β chains of TCR #8 cloned from single TILs were transfected into healthy donor-derived CD8+ T cells and tested on K562 cells expressing two of the HLA class I molecules of the patient pulsed with RETSAT-P546S OLPs. b, Depiction of the underlying neo-epitope presentation on two HLA-alleles. Mutation is underscored (see also FIG. 4)

Figure 4:
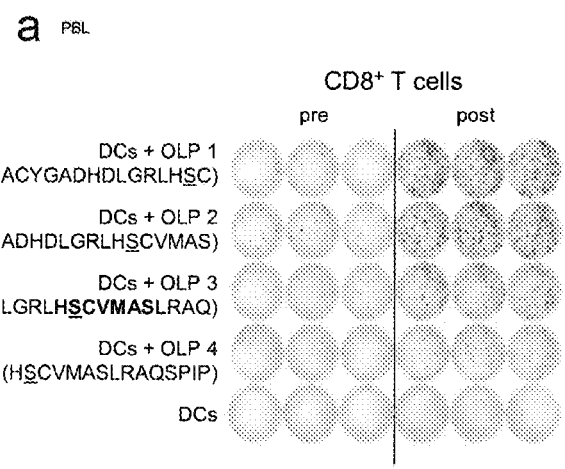
Figure 4:
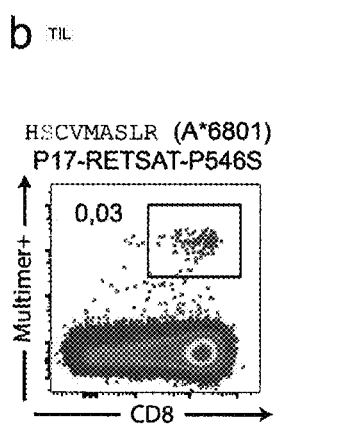
Figure 4:
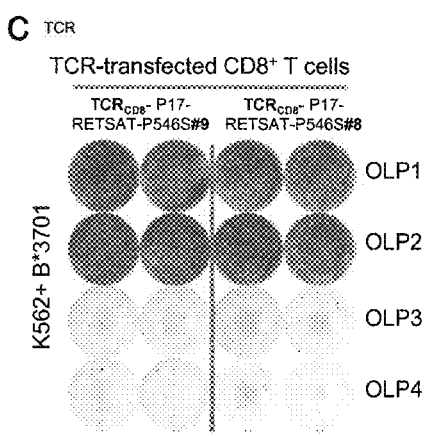

FIG. 4. Induction of CD8+ T-cell responses against two different HLA-restricted T cells epitopes generated by the same mutation. a, IFNγELISpot assay testing of post-vaccine CD8+ T cells of P17 on autologous DCs loaded with individual P17-RETSAT-P546S OLPs. b, Detection of CD8+ T cells recognizing HSCVMASLR, the best-predicted HLA A*6801-restricted minimal epitope within P17-RETSAT-P546 (encoded by OLP 3 and 4) in post-vaccination TILs from patient P17 by multimer staining. c, Specificity of two HLA B*3701-restricted RETSAT-P546S-TCRs obtained from TILs of patient P17 recognizing OLP 1 and 2.

Figure 5:
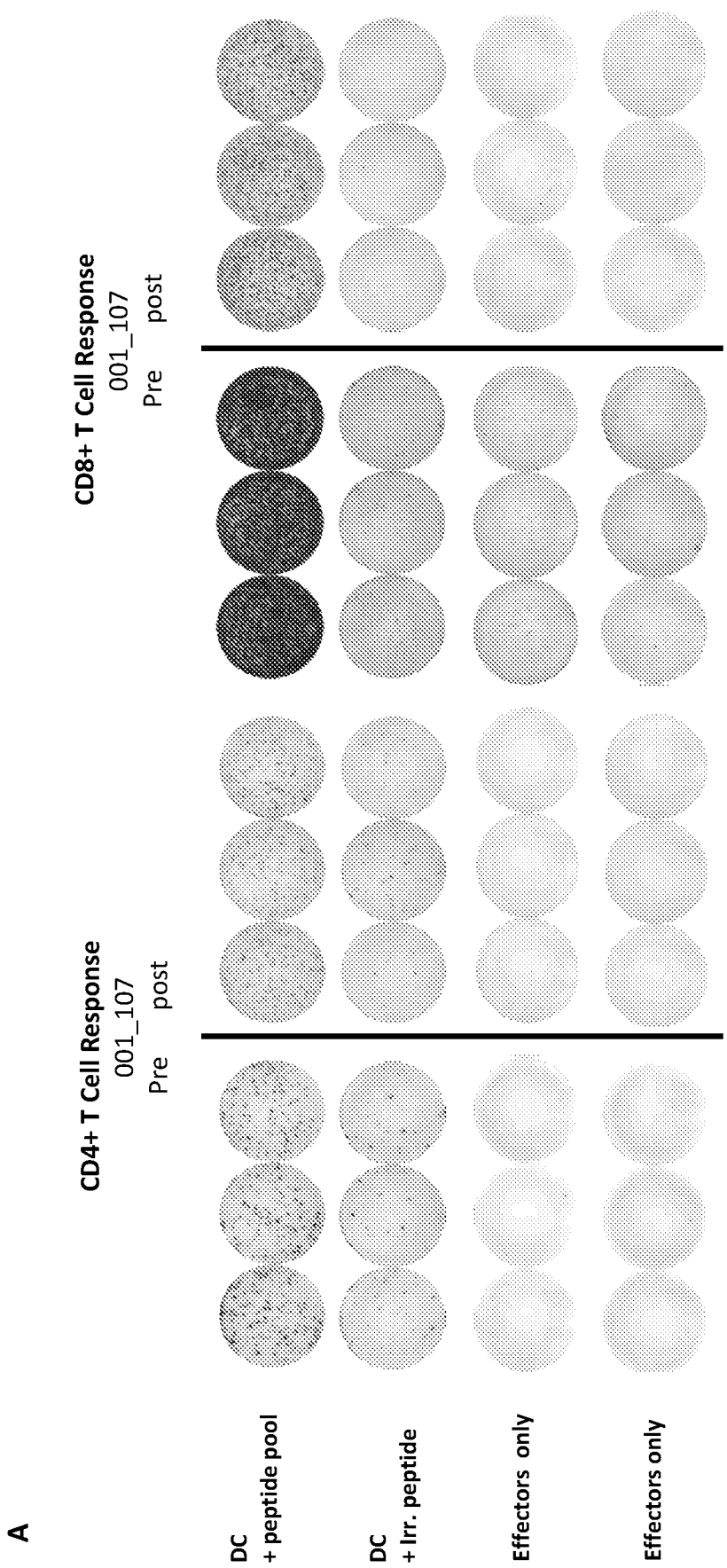
Figure 5:
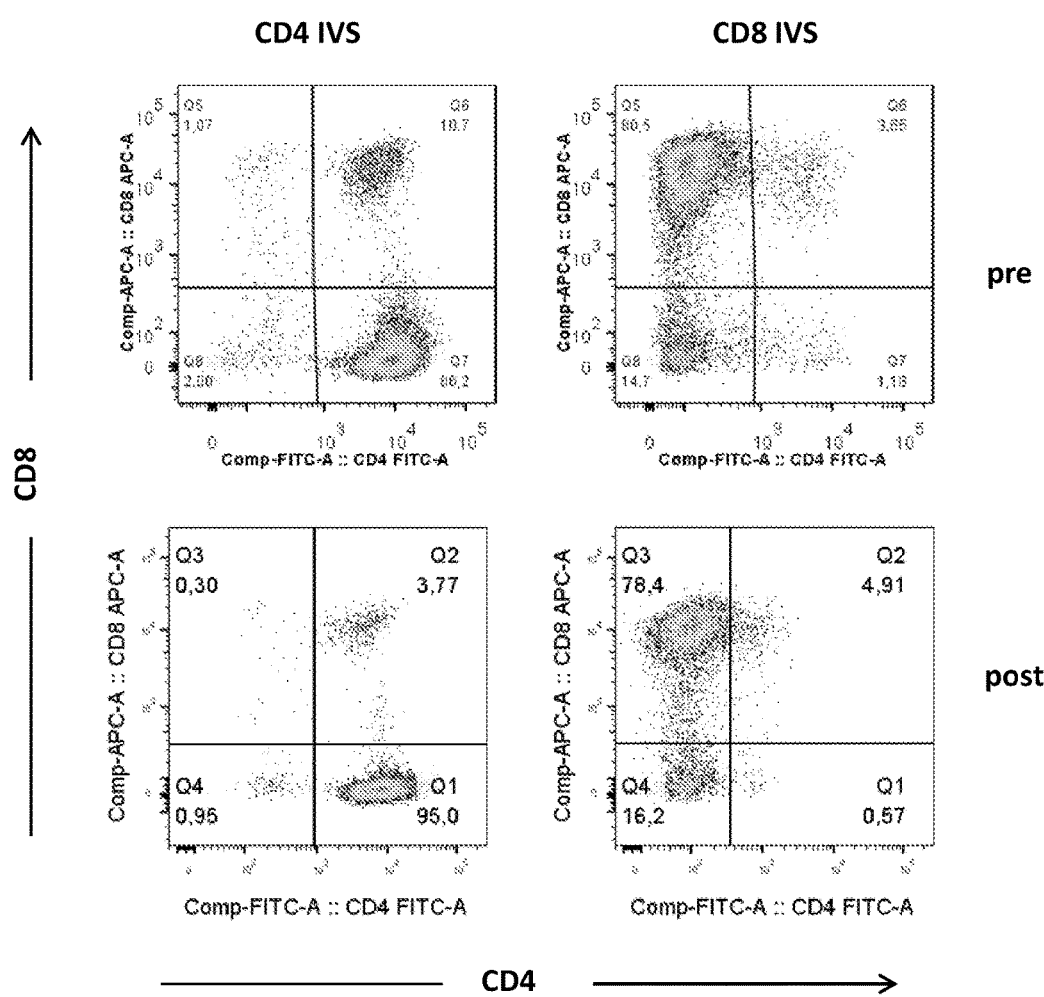
Figure 5:
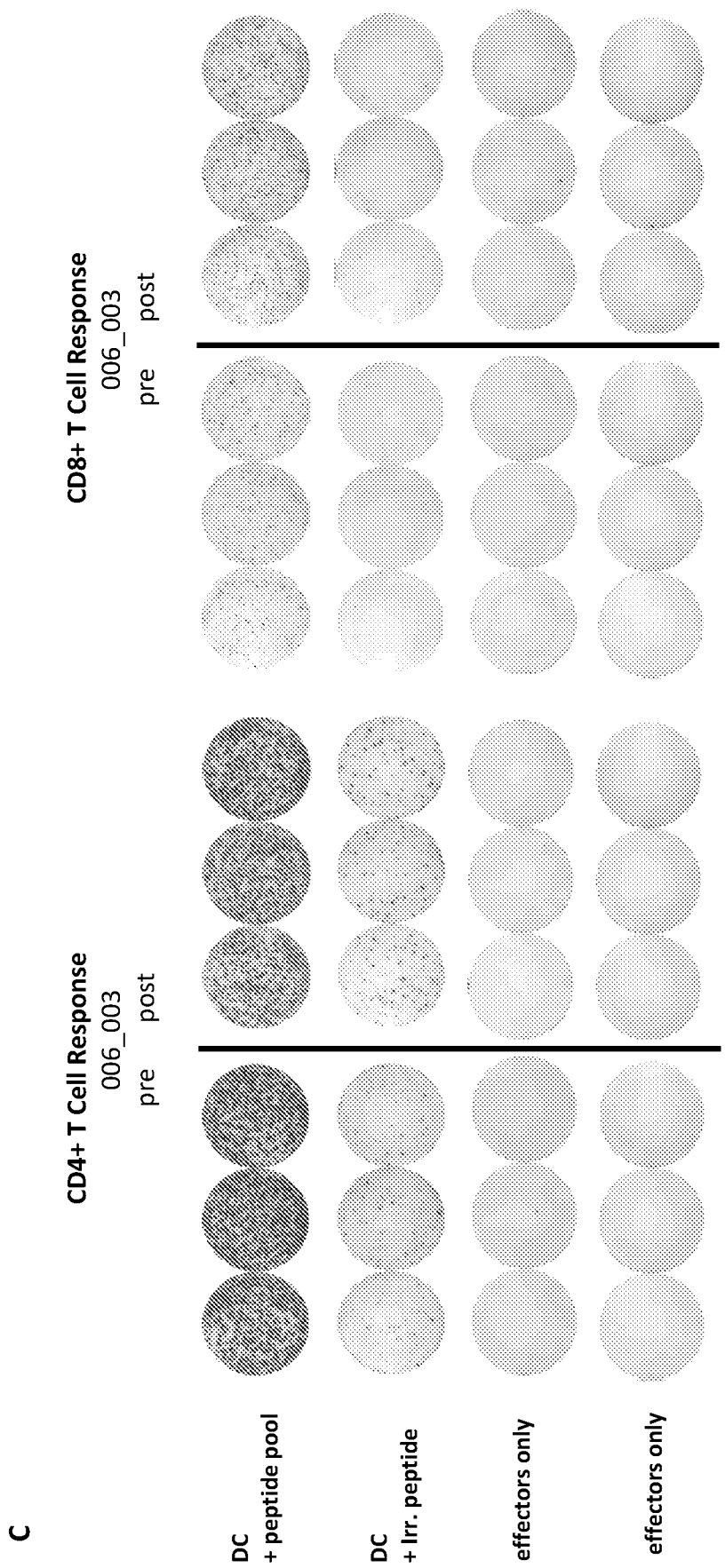
Figure 5:
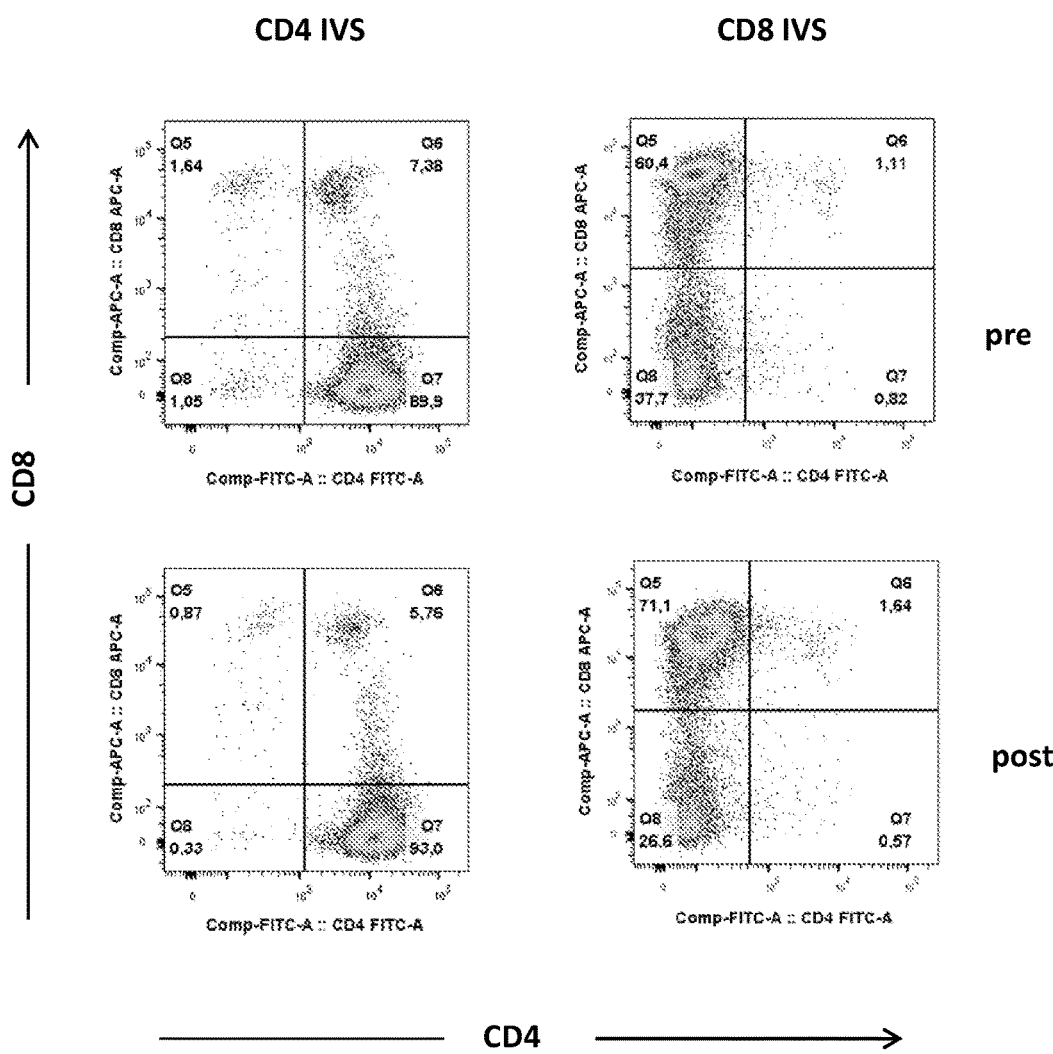

FIG. 5: Pre-existing immune responses mediated by both CD4+ and CD8+ T-cells against neo-epitopes A, CD4+ and CD8+ T-cell enriched cultures of patient P01 stimulated with a pool of OLPs and read-out in IFNγ-ELISpot against autologous DCs loaded with a pool of OLPs covering the target 001_107. Target 001_107 was not vaccinated. B, CD4+ and CD8+ T-cell cultures (IVS) were quality controlled after stimulation for purity by flow cytometry. C, CD4+ and CD8+ T-cell enriched cultures of patient P06 stimulated with a pool of OLPs and read-out in IFNγ-ELISpot against autologous DCs loaded with a pool of OLPs covering the target 006_003. Target 006_003 was not vaccinated. D, CD4+ and CD8+ T-cell cultures were quality controlled after stimulation for purity by flow cytometry.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Study Design

Main objectives of this multicenter phase I study (NCT02035956) were to assess safety of the vaccine and vaccine-induced antigen-specific immune responses.

The study was carried out in accordance with the Declaration of Helsinki and Good Clinical Practice Guidelines and with approval by the institutional review board or independent ethics committee of each participating site and the competent regulatory authorities. All patients provided written informed consent.

Eligible patients were ≥18 years, had malignant melanoma stage IIIA-C or IV (AJCC 2009 melanoma classification) in complete remission, partial remission or stable disease at any stage of treatment. Patients with metastases were eligible if they could be treated with an active compound until availability of their individualized vaccine. Patients had to have adequate haematological and end-organ function. Key exclusion criteria were clinically relevant autoimmune disease, HIV, HBV, HCV and acute EBV or CMV infections and brain metastases. Regular treatment was eight injections within 43 days; continued treatment was left to the investigators' discretion. The RNA pentatopes were diluted in 1.0 mg/mL Ringer's solution (Rotexmedica or BAG Healthcare) and injected into separate inguinal lymph nodes. 10 patients were administered 500 μg and three patients 1000 μg per treatment to explore two different dose ranges.

Key Study Assessments

Leukaphereses for immunogenicity testing were performed prior to the first (visit 12, referred to as 'pre-vaccination') and after the $8^{th}$ vaccine injection (visit 20; referred to as 'post-vaccination'). Imaging of thorax, abdomen, brain by CT scans and MRI were performed at baseline (visit 1), pre-vaccination (visit 12), day 90 (visit 21) and at end of continued treatment (visit 26) according to the local imaging guidelines and RECIST version 1.1 and the immune-related response criteria (irRC) guideline (Wolchok, J. D. et al. Clin. Cancer Res. 15, 7412-20 (2009)). Safety was characterized according to CTCAE v4.03 from grade 1 up to grade 5.

The data presented here is based on an exploratory interim analysis with a data cut-off date of November 2016.

Patient Material

Formalin-fixed and paraffin-embedded (FFPE) or fresh frozen tumor tissue was acquired at routine diagnostic resections and the tumor content was assessed in H&E-stained sections.

Fresh tumor samples were used for the preparation of tumor-infiltrating lymphocytes (TILs) and primary tumor cell lines.

TILs were grown from small pieces of fresh tumor tissue cultured in X-Vivo 15 medium (Lonza) with 2% human serum albumin (CSL-Behring) and 6000 U/mL IL-2 (Proleukin S, Novartis) for two weeks as previously published (Dudley, M. E., Wunderlich, J. R., Shelton, T. E., Even, J. & Rosenberg, S. A. J. Immunother. 26, 332-42). Thereafter, TILs were expanded for two weeks using irradiated, allogeneic PBMCs as feeder cells in the presence of 30 ng/mL anti-CD3 IgG2a (clone OKT3, eBiosciences) and 300 U/mL IL-2 (Proleukin S, Novartis).

For the generation of patient-derived melanoma cell lines, fresh tumor tissue fragments were cultured in RPM11640 medium (Life Technologies) supplemented with 15% FCS (Biochrome AG).

PBMCs obtained for immune monitoring or as starting material for the manufacturing process were isolated by Ficoll-Hypaque (Amersham Biosciences) density gradient centrifugation from buffy coats of healthy donors or from peripheral blood samples of melanoma patients. Immature DCs (DCs) were generated as described previously (Holtkamp, S. et al. Blood 108, 4009-17 (2006)).

Next Generation Sequencing

DNA was extracted from three ten µm-curls FFPE tumor tissue in triplicates using a modified version of Qiagen's QIAamp DNA FFPE Tissue kit. RNA extraction from FFPE tumor curls was done in duplicates using Qiagen's RNeasy FFPE kit. For DNA and RNA extractions from fresh frozen tumor samples or cells, Qiagen's DNeasy Blood and Tissue kit and RNeasy Mini Kit, respectively, were used.

Extracted nucleic acids were used for generation of various libraries. RNA-Seq libraries were prepared in duplicates from FFPE tumor or cell line RNA using Illumina's TruSeq RNA Sample Prep kit V2 and 1 µg total RNA as input. DNA exome capture libraries were constructed in duplicates from 1 to 3 µg of FFPE tumor DNA and matching PBMC DNA using Agilent's SureSelect XT V4 Human All Exon.

NGS libraries for whole genome sequencing (WGS) of MZ-GaBa-018 and matching PBMCs were prepared by fragmenting 100 ng of genomic DNA in a total volume of 15 µL using microTUBE-15 (Covaris Ltd) to an average fragment length of approximately 160 bp. The library was prepared with NEB's NEBNext® Ultra™ DNA Library Prep Kit for Illumina® using 25 ng of fragmented gDNA as input.

For Next Generation Sequencing (NGS) the libraries were diluted to 2 nM or ten nM and clustered at ten pM using the Illumina TruSeq PE Cluster kit v3-cBot-HS. Each exome capture library was sequenced separately in one lane, while the RNA library replicates were sequenced as 2-plexes in one lane. All libraries were sequenced paired-end 50 nt on an Illumina HiSeq 2500 platform using two of Illumina's TruSeq SBS Kit v3-HS 50 cycles. MZ-GaBa-018 cell line and matching PBMC WGS libraries were spread over 4 lanes each and sequenced paired-end 100 nt on the same platform using Illumina's TruSeq SBS Kit v3-HS 200 cycles.

Bioinformatics and Mutation Discovery

All mutanome-related data analysis steps for a single patient were coordinated by a software pipeline implemented in the Python programming language. For the DNA libraries, a minimum of $150 \times 10^6$ paired-end 50 nt reads and for the RNA libraries a minimum of $75 \times 10^6$ paired-end 50 nt reads were required.

For mutation detection, DNA reads were aligned to the reference genome hg19 with bwa (Li, H. & Durbin, R. Bioinformatics 25, 1754-1760 (2009)). Duplicate exomes from tumor and matched normal samples were analyzed for single nucleotide variants. Loci with putative homozygous genotypes in the normal samples were identified and filtered to retain high confidence calls for single nucleotide variants. Remaining sites were further inspected for a putative homozygous or heterozygous mutational event. Suspected sites were filtered to remove potential false positives. Replicates were incorporated by testing both the sum of replicates and replicates separately. The final list of single nucleotide variants was comprised of high confidence homozygous sites in the normal samples and high confidence heterozygous or homozygous mutational events in the tumor samples. Genomic coordinates of identified variants were compared with the UCSC known genes transcript coordinates in order to associate the variants with genes, transcripts, potential amino acid sequence changes and the RNA-Seq derived expression values.

For RNA-Seq, RNA reads were aligned to the hg19 reference genome and transcriptome using bowtie (Langmead, B., Trapnell, C., Pop, M. & Salzberg, S. L. Genome Biol. 10, R25 (2009)), and gene expression was determined by comparison with UCSC known genes transcript and exon coordinates, followed by normalization to RPKM units (Mortazavi, A. et al. Nat. Methods 5, 1-8 (2008)).

Neo-Epitope Prioritization and Selection

From the identified single nucleotide variants, up to 46 predicted variants were selected by an evolving procedure: a) Removal of non-sense variants and filtering by non-zero exon- and transcript expression; followed by sorting first by exon expression and then by HLA class I binding prediction score using a stable sorting algorithm and selecting up to 46 variants (P01-P04). b) Removal of non-sense variants and filtering by non-zero exon- and transcript expression and non-zero variant frequency in the RNA-Seq data; followed by sorting first by exon expression and then by HLA class I binding prediction score using a stable sorting algorithm and selecting up to 23 target peptide sequences; followed by sorting the remaining target peptide sequences first by HLA class I binding prediction score and then by exon expression using a stable sorting algorithm and selecting up to 23 additional target peptide sequences; both selection steps were not allowed to result in more than 46 selected variants (P05-P07, P09-P12) and c) Removal of non-sense variants and filtering by non-zero exon- and transcript expression and non-zero variant frequency in the RNA-Seq data; followed by sorting first by exon expression and then by HLA class II binding prediction score using a stable sorting algorithm and selecting up to 20 target peptide sequences with gene expression≥10 RPKM; followed by sorting the remaining target peptide sequences first by expression and then by HLA class I binding prediction score using a stable sorting algorithm and selecting up to 20 additional target peptide sequences; followed by sorting the remaining target peptide sequences first by HLA class I binding prediction score and then by exon expression using a stable sorting algorithm and filling up to 46 selected variants (P17, P19). The final selection of up to ten mutated target peptides per patient required the decision of a target selection board that evaluated the target peptides based on MHC I and MHC II binding predictions, gene expression and variant allele frequency.

HLA binding affinity was predicted via the IEDB recommended-mode of the IEDB T-cell prediction tools (Kim, Y. et al. Nucleic Acids Res. 40, W525-30 (2012)) (versions 2.5) using all variant-containing 8-11mers for HLA-A/B or 15-mers for HLA-DRB/DQB binding estimations. Out of all predictions for a single variant, the best consensus score was associated with the respective variants.

Based on this data, a short list of single nucleotide variants were selected for confirmation by Sanger sequencing.

Confirmatory Sanger Sequencing

For primer design, genomic sequences flanking the mutation sites were extracted from the reference genome and used as input for the primer3 software (Untergasser, A. et al. Nucleic Acids Res. 40, e115 (2012); Koressaar, T. & Remm, M. Bioinformatics 23, 1289-91 (2007)). The output primer pairs were aligned to the reference genome using blast (Kent, W. J. Genome Res. 12, 656-64 (2002)). Primer pairs with alignments to off-target loci were removed and the remaining optimal primer pair was returned for each input site.

Sanger sequencing was performed by amplifying each selected mutated locus from tumor tissue and PBMC DNA by PCR (15 min at 95° C. for the initial activation followed by 35 cycles of 30 s at 94° C. for denaturation, 30 s at 60° C. for annealing, 30 s at 72° C. for extension, and 6 min at 72° C. for the final extension). Each PCR product was quality controlled using a QIAxcel (Qiagen) device and purified via ExoI/AP treatment or MinElute PCR Purification Kit (Qiagen®). Sanger sequencing was performed by Eurofins/MWG Ebersberg, Germany.

Manufacturing of In Vitro Transcribed RNA

Manufacturing was performed according to GMP (good manufacturing practice) guidelines. Synthetic DNA fragments coding for five putative neo-epitopes were cloned into a starting vector, containing the sec- and MITD-domains (Kreiter, S. et al. J. Immunol. 180, 309-318 (2008)) for optimized routing to HLA class I and II pathways and backbone sequence elements for improved RNA stability and translational efficiency (Holtkamp, S. et al. Blood 108, 4009-17 (2006)). The DNA was linearized, spectrophotometrically quantified, and subjected to in vitro transcription with T7 RNA polymerase as previously described (Grudzien-Nogalska, E. et al. Methods Mol. Biol. 969, 55-72 (2013)) in the presence of 7.5 mM ATP, CTP, UTP, GTP and 3 mM beta-S-ACA(D1) cap analogue (Kuhn, A. N. et al. Gene Ther. 17, 961-971 (2010)) in a clean room environment. RNA was purified using magnetic particles (Berensmeier, S. Appl. Microbiol. Biotechnol. 73, 495-504 (2006)) and integrity was assessed by gel electrophoresis and microfluidic capillary electrophoresis (Experion, Biorad). Further analyses included determination of concentration, appearance, pH, osmolality, potency, endotoxin level and sterility.

In Vitro Stimulation of PBMCs

CD4$^+$ and CD8$^+$ T cells were isolated from cryopreserved PBMCs using microbeads (Miltenyi Biotec). T cells, CD4- or CD8-depleted PBMCs were left to rest overnight. CD4- or CD8-depleted PBMCs were electroporated with RNA encoding patient-specific mutated targets, eGFP, Influenza matrix protein 1 (Ml) or Tetanus p2/p16 sequences (positive control), left to rest for 3 h at 37° C. and irradiated at 15 Gy. CD4$^+$/CD8$^+$ T cells and electroporated and irradiated antigen presenting cells were then combined at an effector to target ratio of 2:1. After one day, fresh culture medium containing ten U/mL IL-2 (Proleukin S, Novartis) and five ng/mL IL-15 (Peprotech) was added. IL-2 was replenished seven days after setting up the cultures. After 11 days of stimulation, cells were analyzed via flow cytometry and used in ELISpot assays.

ELISpot

Multiscreen filter plates (Merck Millipore), pre-coated with antibodies specific for IFNγ (Mabtech) were washed with PBS and blocked with X-Vivo 15 (Lanza) containing 2% human serum albumin (CSL-Behring) for 1-5 hours. $0.5$-$3\times10^5$ effector cells/well were stimulated for 16-20 h (40 h for TILs) with either autologous DCs electroporated with RNA or loaded with peptides, melanoma cell lines or HLA class I or II transfected K562 cells. For analysis of ex vivo T-cell responses, cryopreserved PBMCs were subjected to ELISpot after a resting period of 2-5 hours at 37° C. All tests were performed in duplicate or triplicate and included assay positive controls (*Staphyloccocus* Enterotoxin B (Sigma Aldrich)) as well as cells from a reference donor with known reactivity. Spots were visualized with a biotin-conjugated anti-IFNγ antibody (Mabtech) followed by incubation with ExtrAvidin-Alkaline Phosphatase (Sigma-Aldrich) and BCIP/NBT substrate (Sigma-Aldrich). Plates were scanned using CTL's ImmunoSpot® Series S five Versa ELISpot Analyzer (S5Versa-02-9038) and analyzed by ImmunoCapture V6.3 software. Spot counts were summarized as median values for each triplicate. T-cell responses stimulated by mutated RNA or peptides were compared to control RNA (Luciferase) electroporated target cells or unloaded target cells, respectively. A response was defined as positive with a minimum of five spots per $1\times10^5$ cells in the ex vivo setting or 25 spots per five$\times10^4$ cells in the post-IVS setting as well as a spot count that was more than twice as high as the respective control.

Multimer Staining and Data Analysis

Mutation-specific CD8$^+$ T cells were identified using dextramers (Immudex) carrying 9 or ten amino acid long epitopes from immunogenic mutations. Cells were first stained with multimers after which staining of cell surface markers (CD2S CD28.8, CD197 150503, CD45RA H1100, CD3 UCHT1, CD16 3G8, CD14, MΦDP9, CD19 SJ25C1, CD27 L128, CD279 EH12, CD8 RPA-T8 all BD and CD4 OKT4 Biolegend) and live-dead staining (DAPI BD) was performed. The stained cells were then acquired on a BD LSR Fortessa SORP. Singlet, live, multimer-positive events were identified within CD3 (or CD8) positive, CD4/CD14/CD16/CD19 negative or CD3 (or CD8) positive/CD4 negative events. The specificity of HLA-A*0201 dextramers for patient-specific neo-epitopes is demonstrated by lack of staining of HLA-A*0201$^+$ blood donors.

Intracellular Cytokine Staining

Autologous DCs electroporated with RNA encoding single neo-epitopes were added at a 10:1 E:T ratio and cultured for about 16 hours at 37° C. in the presence of Brefeldin A and Monensin. Cells were stained for viability (fixable viability dye eFluor506, eBioscience), followed by staining for surface markers (CD8 SK1 BD, CD4 OKT4, Biolegend). After permeabilization, intracellular cytokine staining was performed (IL-2 MQI-17H12, IFNγ B27 all BD and TNF a Mab11 Biolegend) and the samples were acquired on a BD FACS Canto II (Becton Dickinson).

Single Cell Sorting

Sorting of single antigen-specific T cells was conducted after 11 days of antigen-specific expansion of PBMCs, purified CD8$^+$ or CD4$^+$ T cells or TILs. Prior to sorting, $2\times10^6$ expanded T cells were restimulated with $2\times10^5$ autologous DCs transfected with IVT RNA encoding the respective neo-antigen or a control antigen. After 16 to 20 h, cells were harvested and treated with fluorochrome-conjugated antibodies directed against CD14, CD19, CD3, CD8, CD4, CD137, CD134 (all from BD Biosciences) as well as IFNγ using the IFNγ secretion assay kit (Miltenyi Biotec). Sorting of single neo-antigen-specific T cells was conducted on a BD FACS Aria flow cytometer (BD Biosciences). One double-positive cell (IFNγ/CD8, CD137/CD8, IFNγ/CD4 or CD134/CD4) per well was harvested in a 96-well V-bottomplate (Greiner Bio-One) containing 3T3-L1 carrier cells, centrifuged and stored at −65° C. to −85° C.

Cloning of Neo-Epitope-Specific TCRs

Cloning of TCR genes from single T cells was performed as previously described (Simon, P. et al. Cancer Immunol. Res. 2, 1230-44 (2014)). In brief, total RNA extracted with the Micro RNeasy Kit (Qiagen) was used for template-switch cDNA synthesis with RevertAid H-Reverse Transcriptase (Thermo Fisher) followed by preamplification using PfuUltra Hotstart DNA Polymerase (Agilent). Aliquots of the resulting cDNAs were used for Vα-/Vβ gene-specific multiplex PCRs. Products were analyzed on a capillary electrophoresis system (Qiagen). Samples with bands at 430 to 470 bp were size fractionated on agarose gels and the bands excised and purified using a Gel Extraction Kit (Qiagen). Purified fragments were sequenced and the respective V(D)J junctions analyzed using the IMGT/V-Quest tool (Brochet, X., Lefranc, M.-P. & Giudicelli, V. Nucleic Acids Res. 36, W503-8 (2008)). DNAs of novel and productively rearranged corresponding TCR chains were NotI-digested and cloned into pST1 vectors containing the appropriate backbones for in vitro transcription of complete TCR-α/β chains (Simon, P. et al. Cancer Immunol. Res. 2, 1230-44 (2014)).

TCR-β/β deep sequencing was performed with total RNA from PBMCs using the TCR-Typer kit (BioNTech Diagnostics). The resulting DNA libraries were sequenced on an Illumina MiSeq sequencer using 2×300 bp paired-end chemistry. Sequencing data was analyzed with Typer Toolbox software. The number of total TCR reads per sample ranged from $1.1 \times 10^6$ to $1.5 \times 10^6$.

qRT-PCR

RNA and cDNA were generated with the ExpressArt FFPE Clear RNAready kit (AmpTec) and PrimeScript™ RT Reagent Kit with gDNA Eraser (Takara Bio Inc.), respectively. qRT-PCR was performed using the BioMark™ HD system (Fluidigm®) or the 96-Well Applied Biosystems 7300 Real-Time PCR System. Samples and assays were prepared and analyzed according to the "Fast Gene Expression Analysis" from FFPE derived RNA using Quantitative SYBR® Green Real-Time PCR or TaqMan® Gene Expression Assays on the BioMark' or "BioMark' HD System Fluidigm® Advanced Development Protocol 28". 96.96 Gene Expression Dynamic Array IFCs were loaded using the IFC Controller HX.

Immunohistochemistry

After deparaffinization of 3 to 4 µm FFPE sections, slides were subjected to antigen retrieval by boiling in ten mM citric acid supplemented with 0.05% Tween-20 (pH 6.0) at 120° C. for ten min, subsequently quenched (by 0.3% $H_2O_2$; 15 min) and blocked with ten % goat serum in PBS (30 min) at room temperature.

Slides were incubated overnight at 2 to eight ° C. with 0.2 µg/mL anti-human CD3 (F7.2.38; Dako), 0.2 µg/mL anti-human CD8 (C8/144B; Dako), 1 µg/mL anti-human FoxP3 (236A/E7; Abeam), 1:200 anti-PD-L1 (13684; Cell Signaling Technologies) or 1:2500 anti-Beta-2-microglobulin (D8P1H; Cell Signaling Technologies) in blocking buffer. Antibody binding was visualized with horseradish-peroxidase-labeled secondary antibodies (BrightVision HRP, Immunologic) together with a red substrate-chromogen solution (VectorRed; Vector Labs). Tumor cells were stained with 1 µg/mL of a Melan-A specific antibody (A103, Dako).

Sections were subsequently counter-stained with Mayer's haematoxylin (Carl Roth GmbH) and subjected to evaluation by a computer based analysis (Definiens Developer).

For analysis, slides were scanned (Axio.Scan; Zeiss) and manually pre-defined tumor, normal tissue and necrotic areas were quantified via computerized image analysis software (Developer, Definiens). The number of CD3, CD8 and FoxP3 TILs was determined in the areas classified as tumor tissue.

Cloning of HLA Antigens

HLA antigens were synthesized by a service provider (Eurofins Genomics) according to respective high-resolution HLA typing results. HLA-DQA sequences were amplified from donor-specific cDNA with 2.5 U Pfu polymerase using DQA1_s (PHO-GCC ACC ATG ATC CTA AAC AAA GCT CTG MTG C) and DQA1_as (TAT GCG ATC GCT CAC AAK GGC CCY TGG TGT CTG) primers. HLA antigens were cloned into appropriately digested IVT vectors (Simon, P. et al. Cancer Immunol. Res. 2, 1230-44 (2014)).

RNA Transfer into Cells

RNA was added to cells suspended in X-VIVO 15 medium (Lonza) in a precooled 4-mm gap sterile electroporation cuvette (Bio-Rad). Electroporation was performed with a BTX ECM 830 square wave electroporation system (T cells: 500 V/3 ms/1 pulse; iDC: 300 V/12 ms/1 pulse; bulk PBMCs: 400V/6 ms/I pulse; MZ-GaBa-018: 225 V/3 ms/2 pulses; K562: 200 V/eight ms/3 pulses).

Peptides

Synthetic 15-mer peptides with 11 amino acid overlaps covering the 27mer neo-antigen sequences (4 OLPs per neo-antigen) or control antigens (HIV-gag, TPTE), referred to as overlapping peptide pool (OLP), or eight to 1 liner epitopes were used. All synthetic peptides were purchased from JPT Peptide Technologies GmbH and dissolved in AquaDest. (Aqua B. Braun, BRAUN Melsungen) with ten % DMSO to a final concentration of 3 mM.

Flow Cytometric Analyses

Cell surface expression of transfected TCR genes was analyzed by flow cytometry using PE- or FITC-conjugated anti-TCR antibodies against the appropriate variable region family or the constant region of the TCR-β chain (Beckman Coulter) and FITC- or APC-labeled anti-CD8/−CD4$^+$ antibodies (BD Biosciences). HLA antigens of the antigen presenting cells used for evaluating the function of TCR-transfected T cells were detected by staining with FITC-labeled HLA class II-specific (Beckman Coulter) and PE-labeled HLA class I-specific antibodies (BD Biosciences). Flow cytometric analysis was performed on a BD FACSCante II analytical flow cytometer (BD Biosciences). Acquired data were analyzed using version ten of the FlowJo software (Tree Star).

Cytotoxicity Assay

A luciferase based cytotoxicity assay was performed as previously described (Omokoko, T. A. et al. J. Immunol. Res. 2016, U.S. Pat. No. 9,540,975 (2016)). $1 \times 10^4$ target cells transfected either with luciferase RNA alone or in combination with B2M RNA were co-cultured with mutation-specific effector T cells (either OKT3-activated TCR-transfected CD8$^+$ T cells or CD4$^+$/CD8$^+$ IVS T cells) for 19 to 25 hours. A reaction mixture containing D-Luciferin (BD Biosciences; final concentration 1.2 mg/mL) was added. One hour later, luminescence was measured using a Tecan Infinite M200 reader (Tecan). Cell killing was calculated by measuring the reduction of total luciferase activity. Viable cells were measured by the luciferase-mediated oxidation of luciferin. Specific killing was calculated according to the following equation:

$$\text{Specific killing in \%} = 100 - \left[\frac{(\text{sample} - \text{complete lysis})}{(\text{max viable cells} - \text{complete lysis})} \times 100\right]$$

Apoptosis Assay

For caspase 3/7 activation apoptosis assay (IncuCyte), $1 \times 10^4$ melanoma cells and $20 \times 10^4$ effector T cells were plated per well in 96-well Corning plates for 24 hours. Caspase 3/7 reagent was added at a 1:1000 dilution of a five mM stock solution (Essen Bioscience), each condition in triplicate. Cells were imaged at 10-fold magnification in an IncuCyte Zoom Live-content imaging system (Essen Bioscience) at 37° C., five % $CO_2$. Images were acquired every hour for 24 hours, four images/well. Data was analyzed using IncuCyte analysis software to detect and quantify green (apoptotic) cells/image. Averages of green object counts with SD at each time point were plotted using GraphPad Prism software.

Example 2: Clinical Feasibility and Favorable Safety of Personalized RNA Vaccination with Neo-Epitopes Previously we have described personalization-related procedures for design and production of RNA vaccines encoding multiple somatic mutations (henceforth 'neo-epitope RNA vaccine') starting from comprehensive mapping of tumor mutations to manufacturing and release of the individual vaccine composition (Kreiter, S. et al. Nature 520, 692-696 (2015); Vormehr, M. et al. J. Immunol. Res. 2015, 6 (2015); Kranz, L. M. et al. Nature 534, 396-401 (2016). These procedures were further developed to a standardized process that complies with regulatory guidelines.

Expressed non-synonymous mutations of stage III and IV melanoma patients were identified by exome and RNA sequencing of nucleic acids from routine frozen or formalin-fixed, paraffin-embedded (FFPE) tumor biopsies and from blood cells as a source for healthy tissue DNA. Two independent principles were applied to rank mutations. One used predicted high-affinity binding to the patient's HLA class II molecules combined with high expression levels of the mutation encoding RNA. The other was based on predicted HLA class I binding. Mutated allele frequencies and relative transcription values served as further differentiators to prioritize mutations with comparable predicted HLA binding affinity. Prioritized tumor-specific somatic mutations were confirmed by Sanger sequencing.

Ten mutations were selected per patient (for patient P09 only five) and engineered into two synthetic RNAs each encoding five 27mer peptides representing one of the mutations (pentatope RNAs). Highly pure RNA was produced according to a Good Manufacturing Practice (GMP) grade process with a success rate of 100%. The median raw manufacturing time for the RNA vaccine was 68 days (range 49 to 102 days). Due to the regulatory requirements for first-in-human use and the investigational stage, each manufactured personalized vaccine underwent an extensive analytical testing extending the total median time to 103 days (range 89 to 160 days) from selection of mutations until vaccine release.

Patients with NY-ESO-1 and/or Tyrosinase positive melanoma were offered an RNA vaccine encoding these two tumor-associated shared self-antigens (TAA) to bridge until the release of their neo-epitope RNA vaccine. Eight doses of the individual RNA vaccine were percutaneously injected into lymph nodes under ultrasound control. Thereafter, post-vaccination blood samples for immunogenicity testing were drawn. Neo-epitope vaccination was continued upon discretion of the investigator.

Twenty patients were screened to participate in the clinical trial, 16 of which were found eligible according to the inclusion and exclusion criteria, and enrolled into the study. Two patients withdrew their consent and one patient could not start the study treatment due to newly diagnosed, rapidly progressing brain metastases. Hence, thirteen patients in total received the neo-epitope RNA vaccine, in nine patients preceded by the bridging TAA RNA vaccine.

All patients successfully completed treatment receiving up to 20 neo-epitope RNA vaccine doses. The number of mutations detected per patient (range 69 to 1440) was in the expected range for melanoma (Lawrence, M. S. et al. Nature 499, 214-8 (2013); Vormehr, M. et al. Curr. Opin. Immunol. 39, 14-22 (2016)). Ten patients had the most common melanoma driver mutations in the BRAF or HRAS/NRAS genes (Hodis, E. et al. Cell 150, 251-263 (2012)). The mutation profiles were dominated by cytosine to thymine (CST) transitions typical of UV-induced melanoma (Pleasance, E. D. et al. Nature 463, 191-196 (2009)).

Overall, the treatment was well tolerated by all patients. Of the 18 reported serious adverse events (SAE), four SAEs in two patients were neo-epitope vaccine treatment-emergent but not related to the study drug. Neo-epitope vaccine treatment-emergent adverse events (AE) were mostly grade 1 or 2. There were no grade 4 or 5 AEs. Drug-related AEs did not cluster to any system organ class. Clinical safety and outcome data will be reported in detail elsewhere.

Example 3: Induction of Poly-Specific T-Cell Immunity by Neo-Epitope RNA Vaccination To gauge immunogenicity of each of the 125 neo-epitopes administered in this study individually, we analysed highly enriched CD4$^+$ and CD8$^+$ T cells from pre- and post-vaccination blood samples. Immunogenicity was read out by IFNγ ELISpot against autologous dendritic cells (DCs) transfected either with RNA encoding a single 27 amino acid (aa) sequence centering the mutation or DCs loaded with 15mer overlapping peptides (OLPs) covering the respective sequence. Both immunogenicity read-outs generated highly concordant results.

Overall, 60% of the neo-epitopes turned out to be immunogenic. Each vaccinated patient responded to at least three of the individual neo-epitopes. Against one third of the immunogenic neo-epitopes there were pre-existent T cells, which were further expanded upon vaccination. Responses against nearly 70% of the neo-epitopes were not detectable prior to vaccination and were induced de novo.

The majority of neo-epitopes were exclusively recognized by CD4⁺ and a smaller fraction by CD8⁺ T cells only. About one quarter of the immunogenic neo-epitopes was double-reactive with both CD4⁺ and CD8⁺ T cells. Cross-contamination of CD4⁺ and CD8⁺ T cells could be excluded experimentally (FIG. 1c). Detailed characterization of the responses by 15mer OLPs showed that the CD4⁺ and the CD8⁺ T cells recognized slightly different parts of the neo-epitope (FIG. 1a,b). Immunogenic neo-epitopes were evenly distributed across the five positions of the pentatope RNA supporting the suitability of the poly-neo-epitope format.

To evaluate whether neo-epitope induced T cells recognize the non-mutated counterpart we tested DCs pulsed with either RNA or OLPs representing wild type or mutated epitopes by ELISpot. For the vast majority of neo-epitope RNA vaccine-induced responses, reactivity against the respective wild type epitope was either not detected or was at a lower level. About one quarter of responses showed reactivity with the wild type epitope above background by ELISpot analyses. It is well conceivable that the 13 aa WT sequence stretches N- and C-terminal of the point mutation may be presented on HLA-class I and HLA-class 11 molecules resulting in wild type epitope reactive T cells. However, a strong expansion of autoreactive T cells is expected to be inhibited by central tolerance mechanisms. We therefore characterized T-cell responses against the vaccine targets (P04-C7-E258K, P09-MAN1A2-E323D, P05-FAM135-A479S) that showed a significant recognition of wild type RNA DCs in more detail. For P04-C7-E258K wild type epitope reactivity was not confirmed by testing DCs loaded with OLPs. For P09-MAN1A2-E323D we observed recognition of both mutated as well as wild type epitopes for peptides spanning aa 9-23 of the 27mer, whereas for peptides spanning aa 5-19 only the mutated version was recognized. This implies that cross reactive immune responses may contain T cells exclusively recognizing the mutated epitope, which may exert tumor control. In all cases we found that autologous DCs, despite of expressing the respective wild type gene endogenously, were not recognized by the respective T cells excluding a biologically significant recognition of the non-mutated gene products.

Example 4: Rapid and Efficient Expansion of Neo-Epitope-Specific T Cells with Central and Effector Memory Phenotypes by Vaccination About one fifth of the immunogenic neo-epitopes in this study elicited very high responses. These T cells were detectable by ex vivo testing of blood samples without prior in vitro stimulation. In patients vaccinated with neo-epitopes and with shared TAA, T-cell responses against neo-epitopes were stronger. To study T-cell recognition at a molecular level, we cloned neo-epitope-specific T-cell receptors (TCR) from post-vaccination T-cell cultures of selected patients. Single neo-epitope-specific CD4⁺ and CD8⁺ T cells were sorted by flow-cytometry and subjected to RT-PCR-based TCR sequencing (Simon, P. et al. Cancer Immunol. Res. 2, 1230-44 (2014)). Cloned TCR alpha and beta chains were in vitro transcribed into RNA and co-transfected into T cells to test for neo-antigen specificity and HLA restriction.

In patient P01 we identified four TCRs, all composed of different TCR alpha/beta clonotypes (Table 1).

TABLE 1

Neo-epitope specific TCR-alpha/beta chains cloned from single T cells of melanoma patients P01 and P02.

| Patient | Mutation | TCR name | TRA | TRB | HLA restriction | Recognized peptide | Recognition of wild-type |
|---------|----------|----------|-----|-----|-----------------|--------------------|--------------------------|
| P01 | NARFL-E62K | TCR$_{CD8}$-NARFL-E62K#1 | V22 J30 C | V5-6 D1 J2-1 C2 | A*3101 | KSQREFVRR | no |
| | | TCR$_{CD8}$- NARFE-E62K#5 | V14/DV4J43 C | V6-5 D1 J2-3 C2 | A*3101 | KSQREFVRR | no |
| | | TCR$_{CD8}$-NARFL-E62K#7 | V29/DV5 J48 C | V6-5 D1 J1-5 C1 | A*3101 | KSQREFVRR | no |
| | | TCR$_{CD8}$-NARFL-E62K#9 | V14/DV4 J45C | V13 D2 J2-3 C2 | A*3101 | KSQREFVRR | no |
| P02 | HPN-G71-R | TCR$_{CD4}$-P02-HPN-G71R#3 | V21 J20 C | V5-6 D2 J2-5 C2 | DRB1*0401 | OLP 1 + 2 | yes (OLP 2) |
| | | TCR$_{CD4}$-P02-HPN-G71R#5 | V8-3*02 J54C | V6-5 D1 J1-2 C1 | DRB1*0401 | OLP 1 + 2 | no |
| | PPFIA4-S709N | TCR$_{CD8}$-P02-PPFIA4-S709N#2 | V21 J10 C | V7-6 D1 J2-7 C2 | B*3906 | MRMNOGVCC. | no |
| | | TCR$_{CD8}$-P02-PPFIA4-S709N#9 | V25 J29 C | V7-6 D1 J2-7 C2 | B*3906 | MRMNQGVCC | no |

The TCR (V(D)J genes are indicated in IMGT nomenclature.

V: variable;

D: diversity;

J: joining;

C: constant.

OLP, overlapping peptides;

t.b.d., to be done;

NARFL, nuclear prelamin A recognition factor-like (NARFL), mRNA; HPN, Hepsin;

PPFIA4, protein tyrosine phosphatase, receptor type, f polypeptide (PTPRF), interacting protein (liprin), alpha 4.

All four TCRs recognized the immune-dominant NARFL-E62K neo-epitope derived from the nuclear prelamin A recognition factor-like gene on HLA A*3101 but not the non-mutated epitope (FIG. 2).

Patient P02 had two HLA B*3906-restricted TCRs recognizing PPFIA4-S709N, a neo-epitope derived from the liprin alpha 4 gene and two TCRs with HLA DRB1*0401-restricted recognition of the mutant hepsin HPN-G71R neo-epitope, which differed with regard to their wild type cross reactivity.

TCR-β sequences of these TCRs were tracked in TCR deep sequencing data generated from the patients' peripheral blood cells pre- (visits V1, V12) and post-vaccination (visit V20). The respective TCR beta clonotypes were not detectable pre-vaccination, but were highly abundant in post-vaccination blood samples.

Investigating neo-epitope responses of several patients by ex vivo MHC multimer analysis revealed fast expansion of circulating CD8$^+$ T cells within 2 to 4 weeks after starting neo-epitope vaccination up to high single-digit percentages. Neo-epitope specific CD8$^+$ T cells contained a weak PD-1 positive memory phenotype subpopulation. Some neo-epitope responses were dominated by central memory, others by effector memory T cells. Upon stimulation with neo-epitope loaded DCs, CD8$^+$ T cells exhibited a typical cytotoxic cytokine pattern with concomitant expression of IFNγ and TNFα.

Example 5: Disease Control in Melanoma Patients with High Risk for Relapse by Personalized Neo-Epitope RNA Vaccination Most of the 13 study patients had a recent history of recurrent disease and all were at high risk of relapse. Comparison of documented melanoma recurrences in all patients prior and after neo-epitope RNA vaccination revealed a highly significant reduction of longitudinal cumulative recurrent metastatic events (p<0.0001), translating into a remarkably long progression free survival in this high-risk patient population. Eight of the patients had no measurable lesions at start of neo-epitope vaccination. All 8 patients mounted strong immune responses against vaccine neo-epitopes and remained recurrence-free within the whole follow up period (range 12 to 23 months) until data cut-off. Kinetics and potency of the immune responses varied; many evolved within the first 3-4 weeks of vaccination. The other five patients experienced tumor progression after inclusion and received standard treatment before application of the vaccine. All five patients had measurable disease at the time their personalized vaccine became available. The course of their disease under neo-epitope vaccination evolved as follows:

Patient P02 had several measurable visceral and lymph node metastases at inclusion and was treated with a BRAF inhibitor, under which the disease progressed slowly. BRAF inhibitor treatment was continued when neo-epitope vaccinations was initiated. P02 mounted CD4+ T-cell responses against six of the ten vaccine neo-epitopes and experienced a mixed response with shrinkage of lymph node metastases, stable visceral metastasis, a progressing thoracic lesion and new measurable metastatic lesions. After radiotherapy and resection of progressing and new lesions, the patient declined further medical treatment and passed away 12 months after the last visit.

Neo-epitope vaccination of Patient P03 was postponed due to disease recurrence with several new hilar lymph node and kidney metastases immediately after inclusion. Local radiotherapy and anti-CTLA-4 treatment failed. The kidney metastasis continued to progress quickly and was resected. After this, neo-epitope RNA vaccination was started and resulted in T-cell responses against three neo-epitopes, two of which were recognized by CD8$^+$ T cells and one by CD4$^+$ and CD8$^+$ T cells. The hilar lymph node metastases progressing prior vaccination resolved completely within the subsequent 12 months as determined by magnetic resonance imaging (MRI). The patient completed treatment with a total of 18 vaccine injections and remained relapse free for 26 months without any further treatment.

Patient P17 was diagnosed with an axillar lymph node metastasis after inclusion into the study, which remained stable and was resected after four neo-epitope RNA vaccine injections and used to generate tumor infiltrating lymphocytes (TILs) and an autologous melanoma cell line (MZ-I-017). The patient continued vaccination for another 14 injections. Notably, reactive T cells against all ten neo-epitopes of the vaccine were detected in PBMCs of P17. Neo-epitope specific T cells were also detected within the tumor infiltrating lymphocytes. Reactivity was particularly high against mutated epitopes of guanylate binding protein (GBP1-P86F) and retinol saturase (RETSAT-P546S). Within the RETSAT-P546S neo-epitope, we identified an HLA-A*6801 restricted minimal epitope (HSCVMASLR) and verified the presence of CD8+ T cells against this epitope in the TILs by HLA-multimer staining.

We stimulated TILs with autologous RETSAT-P546S RNA-transfected DCs and cloned the respective TCRs. T cells transfected with the RETSAT-P546S-specific TCR #8 identified by single cell cloning efficiently killed the autologous melanoma cell line MZ-I-017, but not autologous APCs. This not only confirmed the expression, processing and presentation of the neo-epitope by tumor cells but also its effective recognition on tumor cells by vaccine-induced cytotoxic T cells. Surprisingly, further characterization of TCR #8 revealed HLA-B*3701 (rather than HLA-A*6801) restricted recognition of a neo-epitope, which differed from the originally determined minimal epitope (FIG. 3a,b, FIG. 4). This demonstrates that in the same patient a single mutation may simultaneously trigger CD8$^+$ T cell-responses against different peptide/HLA complexes (FIG. 3b).

Patient P07 had a series of recurrences and progressive skin and visceral metastases at start of neo-epitope RNA vaccination. P07 developed a strong T-cell response against six neo-antigens, five of which were measurable ex vivo. As continued disease progression was documented in the first imaging, neo-epitope vaccination was discontinued. P07 was enrolled into a compassionate anti-PD-1 (pembrolizumab) program. The patient experienced rapid regression of all melanoma lesions, 80% size reduction of target lesions within two months and eventually complete response under continued PD-1 blockade. Vaccine-induced T cells persisted under anti-PD-1 treatment at high frequencies for up to 9 months after end of vaccination.

Example 6: Pre-Existing Immune Responses Mediated by Both CD4+ and CD8+ T-Cells Against Neo-Epitopes Patient Material PBMCs obtained for immunogenicity testing were isolated by Ficoll-Hypaque (Amersham Biosciences) density gradient centrifugation from peripheral blood samples or leukaphereses of melanoma patients. Excess material from NCT02035956 was used for large scale immunogenicity testing. Study design is described on page 80.

Neo-Epitope Selection

The process next generation sequencing is described in detail on page 81. For large scale immunogenicity testing up to one hundred neo-epitopes were selected using an unbiased approach to cover several features such as binding predictions and target expression levels.

In Vitro Stimulation of CD4 and CD8 T Cells

On day zero monocytes were isolated from cryopreserved PBMCs using microbeads (Miltenyi Biotech) and differentiated to fast dendritic cells (fDCs) by adding a cytokine cocktail containing IL-4/GM-CSF and IL-6/IL-1β/TNFα/PGE2. Two days later CD4+ and CD8+ T-cells were isolated from cryopreserved PBMCs using microbeads (Miltenyi Biotech). For in vitro stimulation, CD4+ T-cells and overlapping peptide (OLP) pool loaded fDCs were combined at an effector to target ratio of 10:1 whereas CD8+ T-cells and OLP pool loaded CD4-depleted PBMCs were combined at an effector to target ratio of 1:10. After one day, fresh medium containing 10 U/mL IL-2 (Proleukin S, Novartis) and 5 ng/mL IL-15 (Peprotech) was added. IL-2 was replenished seven days after setting up the cultures. After 11 days of in vitro culture, cells were analyzed via flow cytometry and used as effector cells in IFNγ ELISpot assays.

IFNγ ELIspot

Immature dendritic cells (iDCs) were used as targets for the IFNγ ELIspot assay. Monocytes were isolated from cryopreserved PBMCs using microbeads (Milteniy Biotech) and differentiated to immature dendritic cells (iDCs) in the presence of IL-4 and GM-CSF.

Multiscreen filter plates (Merck Millipore), pre-coated with antibodies specific for IFNγ (Mabtech) were blocked with X-VIVO 15 (Lonza) containing 2% human serum albumin (CSL Behring) for 1-5 hours. For CD4+ T-cells $0.5 \times 10^5$ effector cells/well were re-stimulated with OLP loaded autologous iDCs at an effector to target ratio of 10:1 for 18-20 hours. For CD8+ T cells $1 \times 10^5$ effector cells/well were re-stimulated with OLP loaded autologous iDCs at an effector to target ratio of 10:1 for 18-20 hours. All tests were performed in triplicates and included assay positive controls (*Staphylococcus* Enterotoxin B (Sigma Aldrich)). Control OLP pool loaded iDCs and effectors only were used as negative controls. Spots were visualized with a biotin-conjugated anti-IFNγ antibody (Mabtech) followed by incubation with Extra-Avidin-Alkaline Phosphatase (Sigma-Aldrich) and BCIP/NBT substrate (Sigma-Aldrich). Plates were scanned using CTL's ImmunoSpot® S6Core ELISpot Analyzer and analyzed by ImmunoCapture™ v6.6 software. T-cell responses stimulated by mutated peptides were compared to control peptides (irrelevant peptide pool). A response was defined as positive when the mean spot count was at least two-fold higher in comparison to the respective controls.

Peptides

For in vitro stimulation, synthetic 15-mer peptides (crude products) with an 11 amino acid overlap covering the 27-mer neo-antigen sequences were used (referred to as overlapping peptidey (OLP)). All synthetic peptides were purchased and pre-pooled by PT Peptide Technologies GmbH and dissolved in DMSO (AppliChem) to a stock concentration of 5 mg/mL per OLP. For in vitro stimulation a final concentration of 2.5 µg/mL per OLP was used, for ELISpot Readout 3.5 mg/mL. Pools of different neo-antigens (4 OLPs per neo-antigen) were used for in-vitro stimulation as well as for ELISpot readout using a matrix approach.

Flow Cytometric Analyses

Purity of CD4 and CD8 T cell cultures was assessed by flow cytometry (CD25 PE, CD56 PE CY7, CD8 APC, eFluor780 FVD, CD3 BV42, CD4 FITC). Flow cytometric analysis was performed on a BD FACSVerse™ (BD Biosciences). Acquired data were analyzed using a version ten of the FlowJo software (Tree Star).

Results

Thus far seven patients were analyzed and in total 26 reactivities which are mediated by both CD4+ and CD8+ T-cells were detected.

The invention claimed is:

1. A method of making a cancer vaccine, the method comprising steps of:
   for at least one cancer-specific amino acid modification within a peptide or polypeptide expressed in a cancer cell, determining whether the same or different fragments of the peptide or polypeptide, each of which fragment(s) comprises the same cancer-specific amino acid modification, meet selection criteria in that the same or different fragments:
   (I) are presented by MHC molecules of different classes, and/or
   (II) when presented by MHC molecules, are reactive with T cells restricted to different MHC classes;
   selecting the cancer-specific amino acid modification if the same or different fragments meet the selection criteria; and
   producing a vaccine that comprises (a) the peptide or polypeptide comprising the selected cancer-specific amino acid modification or a fragment thereof that meets the selection criteria; or (b) a nucleic acid encoding the peptide, polypeptide, or fragment of (a).

2. The method of claim 1, wherein the MHC molecules of different classes are MHC class I molecules and MHC class II molecules and/or the T cells restricted to different MHC classes are CD4+ and CD8+ T cells.

3. A method of making a cancer vaccine, the method comprising steps of:
   for at least one cancer-specific amino acid modification within a peptide or polypeptide expressed in a cancer cell, determining whether the same or different fragments of the peptide or polypeptide, each of which fragment(s) comprises the same cancer-specific amino acid modification, meet selection criteria in that the same or different fragments:
   (I) when presented by the same MHC molecule, are reactive with T cells having different T cell receptors;
   selecting the cancer-specific amino acid modification if the same or different fragments meet the selection criteria; and
   producing a vaccine that comprises (a) the peptide or polypeptide comprising the selected cancer-specific amino acid modification or a fragment thereof that meets the selection criteria; or
   (b) a nucleic acid encoding the peptide, polypeptide, or fragment of (a).

4. The method of claim 3, wherein the different T cell receptors are of different clonotypes.

5. A method of making a cancer vaccine, the method comprising steps of:
   for at least one cancer-specific amino acid modification within a peptide or polypeptide expressed in a cancer cell, determining whether the same or different fragments of the peptide or polypeptide, each of which fragment(s) comprises the same cancer specific amino acid modification, meet selection criteria in that the same or different fragments:
   (I) are presented by different MHC molecules of the same class, and/or
   (II) when presented by different MHC molecules of the same class, are reactive with different T cells restricted to the same MHC class;
   selecting the cancer-specific amino acid modification if the same or different fragments meet the selection criteria; and
   producing a vaccine that comprises (a) the peptide or polypeptide comprising the selected cancer-specific amino acid modification or a fragment thereof that meets the selection criteria; or (b) a nucleic acid encoding the peptide, polypeptide, or fragment of (a).

6. The method of claim 5, wherein the different MHC molecules of the same class are different MHC class I molecules and/or the different T cells restricted to the same MHC class are different CD8+ T cells.

7. A method for making a cancer vaccine, the method comprising steps of:
for at least one cancer-specific amino acid modification within a peptide or polypeptide expressed in a cancer cell, determining whether the same or different fragments of the peptide or polypeptide, each of which fragment(s) comprises the same cancer-specific amino acid modification, meet at least two sets of selection criteria (A), (B), and (C), in that the same or different fragments:
according to the selection criteria (A),
(I) are presented by MHC molecules of different classes, and/or
(II) when presented by MHC molecules, are reactive with T cells restricted to different MHC classes;
according to the selection criteria (B),
(I) when presented by the same MHC molecule, are reactive with T cells having different T cell receptors, and/or
according to the selection criteria (C),
(I) are presented by different MHC molecules of the same class, and/or
(II) when presented by different MHC molecules of the same class, are reactive with different T cells restricted to the same MHC class;
selecting the cancer-specific amino acid modification if the same or different fragments meet at least two sets of the selection criteria (A), (B), and (C); and
producing a vaccine that comprises (a) the peptide or polypeptide comprising the selected cancer-specific amino acid modification or a fragment thereof that meets at least two sets of the selection criteria (A), (B), and (C); or (b) a nucleic acid encoding the peptide, polypeptide, or fragment of (a).

8. The method of claim 7, wherein the MHC molecules of different classes are MHC class I molecules and MHC class II molecules and/or the T cells restricted to different MHC classes are CD4+ and CD8+ T cells.

9. The method of claim 7, comprising steps of:
for the at least one cancer-specific amino acid modification, determining whether the same or different fragments of the peptide or polypeptide, each of which fragment(s) comprises the same cancer-specific amino acid modification, meet all three sets of the selection criteria (A), (B), and (C);
selecting the cancer-specific amino acid modification if the same or different fragments meet all three sets of the selection criteria (A), (B), and (C); and
producing a vaccine that comprises (a) the peptide or polypeptide comprising the selected cancer-specific amino acid modification or a fragment thereof that meets all three sets of the selection criteria (A), (B), and (C); or (b) a nucleic acid encoding the peptide, polypeptide, or fragment of (a).

10. The method of claim 7 or 9, wherein the different T cell receptors are of different clonotypes.

11. The method of claim 7 or 9, wherein the different MHC molecules of the same class are different MHC class I molecules and/or the different T cells restricted to the same MHC class are different CD8+ T cells.

12. A method of making a cancer vaccine, the method comprising steps of:
(i) identifying a plurality of cancer-specific amino acid modifications within peptides and/or polypeptides expressed in cancer cells;
(ii) determining, for each cancer-specific amino acid modification in the plurality, whether the same or different fragments of the corresponding peptide or polypeptide, each of which fragment(s) comprises the same cancer-specific amino acid modification, meet the selection criteria in that the same or different fragments:
(I) are presented by MHC molecules of different classes; and/or
(II) when presented by MHC molecules, are reactive with T cells restricted to different MHC classes;
(iii) ranking the level of MHC presentation and/or T cell reactivity for each of the cancer-specific amino acid modifications in the plurality based on the determination of (ii);
(iv) selecting at least one of the cancer-specific amino acid modifications if the same or different fragments comprising the cancer-specific amino acid modification meet the selection criteria and if the cancer-specific amino acid modification has a ranking that is higher than that of at least one of the other cancer-specific amino acid modifications in the plurality; and
(v) producing a vaccine that comprises (a) a peptide or polypeptide comprising the selected cancer-specific amino acid modification, or a fragment thereof; or (b) a nucleic acid encoding the peptide.

13. The method of claim 12, wherein the MHC molecules of different classes are MHC class I molecules and MHC class II molecules and/or the T cells restricted to different MHC classes are CD4+ and CD8+ T cells.

14. A method of making a cancer vaccine, the method comprising steps of:
(i) identifying a plurality of cancer-specific amino acid modifications within peptides and/or polypeptides expressed in cancer cells;
(ii) determining, for each cancer-specific amino acid modification in the plurality, whether the same or different fragments of the corresponding peptide or polypeptide, each of which fragment(s) comprises the same cancer specific amino acid modification, meet selection criteria in that the same or different fragments, when presented by the same MHC molecule, are reactive with T cells having different T cell receptors;
(iii) ranking the level of MHC presentation and/or T cell reactivity for each of the cancer-specific amino acid modifications in the plurality based on the determination of (ii);
(iv) selecting at least one of the cancer-specific amino acid modifications if the same or different fragments comprising the cancer-specific amino acid modification meet the selection criteria and if the cancer-specific amino acid modification has a ranking that is higher than that of at least one of the other cancer-specific amino acid modifications in the plurality; and
(v) producing a vaccine that comprises (a) a peptide or polypeptide comprising the selected cancer-specific amino acid modification, or a fragment thereof; or (b) a nucleic acid encoding the peptide, polypeptide, or fragment of (a).

15. The method of claim 14, wherein the different T cell receptors are of different clonotypes.

16. A method of making a cancer vaccine, the method comprising:
(i) identifying a plurality of cancer-specific amino acid modifications within peptides and/or polypeptides expressed in cancer cells;
(ii) determining, for each cancer-specific amino acid modification in the plurality, whether the same or different fragments of the corresponding peptide or polypeptide, each of which fragment(s) comprises the same cancer-specific amino acid modification, meet selection criteria in that the same or different fragments:
(I) are presented by different MHC molecules of the same class; and/or
(II) when presented by different MHC molecules of the same class, are reactive with different T cells restricted to the same MHC class;
(iii) ranking the level of MHC presentation and/or T cell reactivity for each of the cancer-specific amino acid modifications in the plurality based on the determination of (ii);
(iv) selecting at least one of the cancer-specific amino acid modifications if the same or different fragments comprising the cancer-specific amino acid modification meet the selection criteria and if the cancer-specific amino acid modification has a ranking that is higher than that of at least one of the other cancer-specific amino acid modifications in the plurality; and
(v) producing a vaccine that comprises (a) a peptide or polypeptide comprising the selected cancer-specific amino acid modification, or a fragment thereof; or (b) a nucleic acid encoding the peptide, polypeptide, or fragment of (a).

17. The method of claim 16, wherein the different MHC molecules of the same class are different MHC class I molecules and/or the different T cells restricted to the same MHC class are different CD8+ T cells.

18. A method of making a cancer vaccine, the method comprising:
(i) identifying a plurality of cancer specific amino acid modifications within peptides and/or polypeptides expressed in cancer cells;
(ii) determining, for each cancer-specific amino acid modification in the plurality, whether the same or different fragments of the corresponding peptide or polypeptide, each of which fragment(s) comprises the same cancer-specific amino acid modification, meet at least two sets of selection criteria (A), (B), and (C), in that the same or different fragments:
according to the selection criteria (A),
(I) are presented by MHC molecules of different classes and/or
(II) when presented by MHC molecules, are reactive with T cells restricted to different MHC classes,
according to the selection criteria (B),
(I) when presented by the same MHC molecule, are reactive with T cells having different T cell receptors, and/or
according to the selection criteria (C),
(I) are presented by different MHC molecules of the same class, and/or
(II) when presented by different MHC molecules of the same class, are reactive with different T cells restricted to the same MHC class,
(iii) ranking the level of MHC presentation and/or T cell reactivity for each of the cancer-specific amino acid modifications in the plurality based on the determination of (ii);
(iv) selecting at least one of the cancer-specific amino acid modifications if the same or different fragments comprising the cancer-specific amino acid modification meet at least two sets of the selection criteria (A), (B), and (C), and if the cancer-specific amino acid modification has a ranking that is higher than that of at least one of the other cancer-specific amino acid modifications in the plurality; and
(v) producing a vaccine that comprises (a) a peptide or polypeptide comprising the selected cancer-specific amino acid modification, or a fragment thereof; or (b) a nucleic acid encoding the peptide, polypeptide, or fragment of (a).

19. The method of claim 18, wherein the MHC molecules of different classes are MHC class I molecules and MHC class II molecules and/or the T cells restricted to different MHC classes are CD4+ and CD8+ T cells.

20. The method of claim 18, comprising steps of:
(ii) determining, for each cancer-specific amino acid modification in the plurality, whether the same or different fragments of the corresponding peptide or polypeptide, each of which fragment(s) comprises the same cancer-specific amino acid modification, meet all three sets of the selection criteria (A), (B), and (C), and
(iii) ranking the level of MHC presentation and/or T cell reactivity for each of the cancer-specific amino acid modifications in the plurality based on the determination of (ii);
(iv) selecting at least one of the cancer-specific amino acid modifications if the same or different fragments comprising the cancer-specific amino acid modification meet all three sets of the selection criteria (A), (B), and (C), and if the cancer-specific amino acid modification has a ranking that is higher than that of at least one of the other cancer-specific amino acid modifications in the plurality; and
(v) producing a vaccine that comprises (a) a peptide or polypeptide comprising the selected cancer-specific amino acid modification, or a fragment thereof; or (b) a nucleic acid encoding the peptide, polypeptide, or fragment of (a).

21. The method of claim 18 or 20, wherein the different T cell receptors are of different clonotypes.

22. The method of claim 18 or 20, wherein the different MHC molecules of the same class are different MHC class I molecules and/or the different T cells restricted to the same MHC class are different CD8+ T cells.

23. The method of any one of claims 12, 14, 16, 18, and 20, wherein the different amino acid modifications determined in step (ii) are present in the same and/or in different peptides or polypeptides.

24. The method of any one of claims 12, 14, 16, 18, and 20, wherein the step of ranking comprises assigning a score to each of the cancer-specific amino acid modifications based on the determination of (ii) and comparing the scores obtained for each of the amino acid modifications determined in (ii).

25. The method of any one of claims 1, 3, 5, 7, 9, 12, 14, 16, 18, and 20, wherein the cancer-specific amino acid modification(s) is (are) cancer-specific somatic mutation(s).

26. The method of any one of claims 1, 3, 5, 7, 9, 12, 14, 16, 18, and 20, wherein the fragment(s) comprising the cancer-specific amino acid modification is a MHC binding peptide or a potential MHC binding peptide or can be processed to provide a MHC binding peptide or a potential MHC binding peptide.

\* \* \* \* \*

SEQUENCE LISTING

```
<160> NUMBER OF SEQ ID NOS: 23

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
      preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
      is independently a number selected from 0, 1, 2, 3, 4, 5, 6, 7, 8,
```

```
      9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
      is independently a number selected from 0, 1, 2, 3, 4, 5, 6, 7, 8,
      9, 10, 11, 12, 13, 14, 15, 16, 17, 18, 19, or 20

<400> SEQUENCE: 1

Gly Gly Ser Gly Ser Ser Gly Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5

<210> SEQ ID NO 3
<211> LENGTH: 9
<212> TYPE: PRT
<213> ORGANISM: Homo sapiens

<400> SEQUENCE: 3

Lys Ser Gln Arg Glu Phe Val Arg Arg
1               5

<210> SEQ ID NO 4
<211> LENGTH: 9
<212> TYPE: PRT
<213> ORGANISM: Homo sapiens

<400> SEQUENCE: 4

Met Arg Met Asn Gln Gly Val Cys Cys
1               5

<210> SEQ ID NO 5
<211> LENGTH: 14
<212> TYPE: PRT
<213> ORGANISM: Homo sapiens

<400> SEQUENCE: 5

Lys Phe Gly Gln Gly Leu Glu Asp Gln Leu Ala Thr Lys Ser
1               5                   10

<210> SEQ ID NO 6
<211> LENGTH: 15
<212> TYPE: PRT
<213> ORGANISM: Homo sapiens

<400> SEQUENCE: 6

Gly Gln Gly Leu Glu Asp Gln Leu Ala Gln Thr Lys Ser Leu Ser
1               5                   10                  15

<210> SEQ ID NO 7
<211> LENGTH: 15
```

```
<212> TYPE: PRT
<213> ORGANISM: Homo sapiens

<400> SEQUENCE: 7

Gly Leu Glu Asp Gln Leu Ala Gln Thr Lys Ser Leu Ser Leu Asp
1               5                   10                  15

<210> SEQ ID NO 8
<211> LENGTH: 15
<212> TYPE: PRT
<213> ORGANISM: Homo sapiens

<400> SEQUENCE: 8

Glu Asp Gln Leu Ala Gln Thr Lys Ser Leu Ser Leu Asp Asp Cys
1               5                   10                  15

<210> SEQ ID NO 9
<211> LENGTH: 15
<212> TYPE: PRT
<213> ORGANISM: Homo sapiens

<400> SEQUENCE: 9

Thr Arg Leu Ser Lys Val Phe Ser Ala Met Leu Ala Ile Tyr Ser
1               5                   10                  15

<210> SEQ ID NO 10
<211> LENGTH: 15
<212> TYPE: PRT
<213> ORGANISM: Homo sapiens

<400> SEQUENCE: 10

Lys Val Phe Ser Ala Met Leu Ala Ile Tyr Ser Asn Lys Pro Ala
1               5                   10                  15

<210> SEQ ID NO 11
<211> LENGTH: 15
<212> TYPE: PRT
<213> ORGANISM: Homo sapiens

<400> SEQUENCE: 11

Ala Met Leu Ala Ile Tyr Ser Asn Lys Pro Ala Leu Trp Ile Met
1               5                   10                  15

<210> SEQ ID NO 12
<211> LENGTH: 15
<212> TYPE: PRT
<213> ORGANISM: Homo sapiens

<400> SEQUENCE: 12

Ile Tyr Ser Asn Lys Pro Ala Leu Trp Ile Met Ala Ala Lys Trp
1               5                   10                  15

<210> SEQ ID NO 13
<211> LENGTH: 19
<212> TYPE: PRT
<213> ORGANISM: Homo sapiens

<400> SEQUENCE: 13

Ala Asp His Asp Leu Gly Arg Leu His Ser Cys Val Met Ala Ser Leu
1               5                   10                  15

Arg Ala Gln

<210> SEQ ID NO 14
<211> LENGTH: 9
```

```
<212> TYPE: PRT
<213> ORGANISM: Homo sapiens

<400> SEQUENCE: 14

His Asp Leu Gly Arg Leu His Ser Cys
1               5

<210> SEQ ID NO 15
<211> LENGTH: 9
<212> TYPE: PRT
<213> ORGANISM: Homo sapiens

<400> SEQUENCE: 15

His Ser Cys Val Met Ala Ser Leu Arg
1               5

<210> SEQ ID NO 16
<211> LENGTH: 15
<212> TYPE: PRT
<213> ORGANISM: Homo sapiens

<400> SEQUENCE: 16

Ala Cys Tyr Gly Ala Asp His Asp Leu Gly Arg Leu His Ser Cys
1               5                   10                  15

<210> SEQ ID NO 17
<211> LENGTH: 15
<212> TYPE: PRT
<213> ORGANISM: Homo sapiens

<400> SEQUENCE: 17

Ala Asp His Asp Leu Gly Arg Leu His Ser Cys Val Met Ala Ser
1               5                   10                  15

<210> SEQ ID NO 18
<211> LENGTH: 15
<212> TYPE: PRT
<213> ORGANISM: Homo sapiens

<400> SEQUENCE: 18

Leu Gly Arg Leu His Ser Cys Val Met Ala Ser Leu Arg Ala Gln
1               5                   10                  15

<210> SEQ ID NO 19
<211> LENGTH: 15
<212> TYPE: PRT
<213> ORGANISM: Homo sapiens

<400> SEQUENCE: 19

His Ser Cys Val Met Ala Ser Leu Arg Ala Gln Ser Pro Ile Pro
1               5                   10                  15

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide

<400> SEQUENCE: 20
gccaccatga tcctaaacaa agctctgmtg c                              31

<210> SEQ ID NO 21
<211> LENGTH: 33
<212> TYPE: DNA
```

```
<213> ORGANISM: Artificial Sequence
<220> FEATURE:
<223> OTHER INFORMATION: Oligonucleotide

<400> SEQUENCE: 21
tatgcgatcg ctcacaakgg cccytggtgt ctg                                    33

<210> SEQ ID NO 22
<211> LENGTH: 27
<212> TYPE: PRT
<213> ORGANISM: Homo sapiens

<400> SEQUENCE: 22

Cys Ser Pro Gly Phe Phe Lys Phe Glu Ala Ser Glu Ser Leu Cys Leu
1               5                   10                  15

Glu Cys Pro Glu His Thr Leu Pro Ser Pro Glu
            20                  25

<210> SEQ ID NO 23
<211> LENGTH: 18
<212> TYPE: PRT
<213> ORGANISM: Homo sapiens

<400> SEQUENCE: 23

Met Pro Arg Ser Glu Ser Tyr Cys Phe Pro Gly Val Thr Leu Ala Ser
1               5                   10                  15

Thr Pro
```